US012807982B2

(12) United States Patent
Sukovich et al.

(10) Patent No.: US 12,807,982 B2
(45) Date of Patent: Nov. 24, 2026

(54) METHODS, COMPOSITIONS, AND SYSTEMS FOR ENHANCING SPATIAL ANALYSIS OF ANALYTES IN A BIOLOGICAL SAMPLE

(71) Applicant: 10x Genomics, Inc., Pleasanton, CA (US)

(72) Inventors: David Sukovich, Oakland, CA (US); Hardeep Pal Singh, Pleasanton, CA (US); Lauren Gutgesell, Pleasanton, CA (US); Ace George Santiago, Pleasanton, CA (US); Benton Veire, Pleasanton, CA (US); Anuj Patel, Pleasanton, CA (US)

(73) Assignee: 10x Genomics, Inc.

( * ) Notice: Subject to any disclaimer, the term of this patent is extended or adjusted under 35 U.S.C. 154(b) by 294 days.

(21) Appl. No.: 18/399,109

(22) Filed: Dec. 28, 2023

(65) Prior Publication Data

US 2024/0218427 A1 Jul. 4, 2024

Related U.S. Application Data

(60) Provisional application No. 63/436,003, filed on Dec. 29, 2022.

(51) Int. Cl.
*C12Q 1/6823* (2018.01)
*G01N 33/58* (2006.01)
*G01N 33/68* (2006.01)

(52) U.S. Cl.
CPC ........... *C12Q 1/6823* (2013.01); *G01N 33/58* (2013.01); *G01N 33/6857* (2013.01); *G01N 2458/10* (2013.01)

(58) Field of Classification Search
CPC ........ C12Q 1/68; C12Q 1/686; C12Q 1/6823; G01N 33/6857
See application file for complete search history.

(56) References Cited

U.S. PATENT DOCUMENTS 4,683,195 A 7/1987 Mullis
4,683,202 A 7/1987 Mullis
4,800,159 A 1/1989 Mullis
4,883,867 A 11/1989 Lee
4,965,188 A 10/1990 Mullis
4,988,617 A 1/1991 Landegren et al.
5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,494,810 A 2/1996 Barany et al.
5,503,980 A 4/1996 Cantor
5,512,439 A 4/1996 Hornes
5,512,462 A 4/1996 Cheng
5,559,032 A 9/1996 Porneroy
5,582,977 A 12/1996 Yue
5,599,675 A 2/1997 Brenner
5,641,658 A 6/1997 Adams
5,648,245 A 7/1997 Fire et al.
5,658,751 A 8/1997 Yue
5,695,940 A 12/1997 Drmanac et al.
5,716,825 A 2/1998 Hancock et al.
5,750,341 A 5/1998 Macevicz
5,763,175 A 6/1998 Brenner
5,830,711 A 11/1998 Barany et al.
5,837,832 A 11/1998 Chee et al.
5,854,033 A 12/1998 Lizardi
5,863,753 A 1/1999 Haugland
5,871,921 A 2/1999 Landegren et al.
5,912,148 A 6/1999 Eggerding
5,925,545 A 7/1999 Reznikoff et al.
5,928,906 A 7/1999 Koester et al.
5,958,775 A 9/1999 Wickstrrom
5,962,271 A 10/1999 Chenchik et al.
5,962,272 A 10/1999 Chenchik et al.
5,965,443 A 10/1999 Reznikoff et al.
6,013,440 A 1/2000 Lipshutz
6,027,889 A 2/2000 Barany et al.
6,054,274 A 4/2000 Sampson et al.
6,060,240 A 5/2000 Kamb et al.
6,083,761 A 7/2000 Kedar et al.
6,130,073 A 10/2000 Eggerding
(Continued)

FOREIGN PATENT DOCUMENTS

AU 2003200718 10/2006
CA 3054046 3/2020
(Continued)

OTHER PUBLICATIONS

Saarenpaa et al., "Spatial metatranscriptomics resolves host-bacteria-fungi interactomes," Nature Biotechnology, Nov. 20, 2023, 42:1384-1393, 19 pages.
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.
10xGenomics.com, [online], "Visium Spatial Gene Expression Reagent Kits—User Guide," Sep. 2023, retrieved on Mar. 29, 2024, retrieved from URL<https://cdn.10xgenomics.com/image/upload/v1695417753/support-documents/CG000239_VisiumSpatialGeneExpression_UserGuide_RevG.pdf>, 70 pages.
(Continued)

*Primary Examiner* — Young J Kim
(74) *Attorney, Agent, or Firm* — Fish & Richardson P.C.

(57) ABSTRACT

Provided herein are methods for spatial analysis of proteins and/or nucleic acids by capturing a capture handle sequence and/or a connected probe to a capture domain of a capture probe on a spatial array. In some instances, a reagent medium including a monovalent or divalent salt, ethylene carbonate, and/or glycerol is used in the disclosed methods.

20 Claims, 23 Drawing Sheets

(56) References Cited

U.S. PATENT DOCUMENTS 6,143,496 A 11/2000 Brown
6,153,389 A 11/2000 Haarer
6,159,736 A 12/2000 Reznikoff et al.
6,165,714 A 12/2000 Lane et al.
6,210,891 B1 4/2001 Nyren
6,210,894 B1 4/2001 Brennan
6,214,587 B1 4/2001 Dattagupta
6,251,639 B1 6/2001 Kurn
6,258,568 B1 7/2001 Nyren
6,266,459 B1 7/2001 Walt
6,268,148 B1 7/2001 Barany et al.
6,274,320 B1 8/2001 Rothberg
6,291,180 B1 9/2001 Chu
6,291,187 B1 9/2001 Kingsmore et al.
6,300,063 B1 10/2001 Lipshutz et al.
6,309,824 B1 10/2001 Drmanac
6,323,009 B1 11/2001 Lasken et al.
6,344,316 B1 2/2002 Lockhart
6,344,329 B1 2/2002 Lizardi et al.
6,355,431 B1 3/2002 Chee
6,368,801 B1 4/2002 Faruqi
6,401,267 B1 6/2002 Drmanac
6,404,907 B1 6/2002 Gilchrist
6,432,360 B1 8/2002 Church et al.
6,503,713 B1 1/2003 Rana
6,506,561 B1 1/2003 Cheval et al.
6,534,266 B1 3/2003 Singer
6,544,732 B1 4/2003 Chee
6,544,790 B1 4/2003 Sabatini
6,573,043 B1 6/2003 Cohen et al.
6,579,695 B1 6/2003 Lambalot
6,620,584 B1 9/2003 Chee
6,632,641 B1 10/2003 Brennan
6,673,620 B1 1/2004 Loeffler
6,699,710 B1 3/2004 Kononen
6,737,236 B1 5/2004 Pieken et al.
6,770,441 B2 8/2004 Dickinson
6,773,886 B2 8/2004 Kaufman
6,787,308 B2 9/2004 Balasubramanian
6,797,470 B2 9/2004 Barany et al.
6,800,453 B2 10/2004 Labaer
6,812,005 B2 11/2004 Fan et al.
6,828,100 B1 12/2004 Ronaghi
6,833,246 B2 12/2004 Balasubramanian
6,852,487 B1 2/2005 Barany et al.
6,859,570 B2 2/2005 Walt
6,864,052 B1 3/2005 Drmanac
6,867,028 B2 3/2005 Janulaitis
6,872,816 B1 3/2005 Hall et al.
6,875,572 B2 4/2005 Prudent et al.
6,890,741 B2 5/2005 Fan et al.
6,897,023 B2 5/2005 Fu
6,913,881 B1 7/2005 Aizenstein et al.
6,942,968 B1 9/2005 Dickinson et al.
7,011,944 B2 3/2006 Prudent et al.
7,057,026 B2 6/2006 Barnes
7,083,980 B2 8/2006 Reznikoff et al.
7,098,041 B2 8/2006 Kaylor et al.
7,115,400 B1 10/2006 Adessi
7,118,883 B2 10/2006 Inoue
7,166,431 B2 1/2007 Chee et al.
7,192,735 B2 3/2007 Lambalot
7,211,414 B2 5/2007 Hardin
7,255,994 B2 8/2007 Lao
7,258,976 B2 8/2007 Mitsuhashi
7,282,328 B2 10/2007 Kong et al.
7,297,518 B2 11/2007 Quake
7,329,492 B2 2/2008 Hardin
7,358,047 B2 4/2008 Hafner et al.
7,361,488 B2 4/2008 Fan et al.
7,378,242 B2 5/2008 Hurt
7,393,665 B2 7/2008 Brenner
7,405,281 B2 7/2008 Xu
7,407,757 B2 8/2008 Brenner
7,473,767 B2 1/2009 Dimitrov
7,499,806 B2 3/2009 Kermani et al.
7,537,897 B2 5/2009 Brenner
7,563,576 B2 7/2009 Chee
7,579,153 B2 8/2009 Brenner
7,582,420 B2 9/2009 Oliphant et al.
7,601,498 B2 10/2009 Mao
7,608,434 B2 10/2009 Reznikoff et al.
7,611,869 B2 11/2009 Fan
7,635,566 B2 12/2009 Brenner
7,666,612 B2 2/2010 Johnsson
7,674,752 B2 3/2010 He
7,700,286 B2 4/2010 Stroun et al.
7,709,198 B2 5/2010 Luo et al.
7,759,062 B2 7/2010 Allawi et al.
7,776,547 B2 8/2010 Roth
7,776,567 B2 8/2010 Mao
7,803,943 B2 9/2010 Mao
7,888,009 B2 2/2011 Barany et al.
7,892,747 B2 2/2011 Barany et al.
7,910,304 B2 3/2011 Drmanac
7,914,981 B2 3/2011 Barany et al.
7,919,308 B2 4/2011 Paul
7,955,794 B2 6/2011 Shen et al.
7,960,119 B2 6/2011 Chee
7,985,565 B2 7/2011 Mayer et al.
8,003,354 B2 8/2011 Shen et al.
8,074,802 B2 12/2011 Webb et al.
8,076,063 B2 12/2011 Fan
8,092,784 B2 1/2012 Mao
8,148,068 B2 4/2012 Brenner
8,206,917 B2 6/2012 Chee
8,207,093 B2 6/2012 Szostak
8,268,554 B2 9/2012 Schallmeiner
8,288,103 B2 10/2012 Oliphant
8,288,122 B2 10/2012 O'Leary et al.
8,383,338 B2 2/2013 Kitzman
8,431,691 B2 4/2013 McKernan et al.
8,460,865 B2 6/2013 Chee
8,481,257 B2 7/2013 Van Eijk
8,481,258 B2 7/2013 Church et al.
8,481,292 B2 7/2013 Casbor
8,481,698 B2 7/2013 Lieberman et al.
8,507,204 B2 8/2013 Pierce et al.
8,519,115 B2 8/2013 Webster et al.
8,551,710 B2 10/2013 Bernitz et al.
8,568,979 B2 10/2013 Stuelpnagel et al.
8,586,310 B2 11/2013 Mitra
8,597,891 B2 12/2013 Barany et al.
8,603,743 B2 12/2013 Liu et al.
8,604,182 B2 12/2013 Luo et al.
8,614,073 B2 12/2013 Van Eijk
8,624,016 B2 1/2014 Barany et al.
8,685,889 B2 4/2014 Van Eijk
8,741,564 B2 6/2014 Seligmann
8,741,606 B2 6/2014 Casbon
8,771,950 B2 7/2014 Church et al.
8,785,353 B2 7/2014 Van Eijk
8,790,873 B2 7/2014 Namsaraev et al.
8,809,238 B2 8/2014 Livak et al.
8,815,512 B2 8/2014 Van Eijk
8,835,358 B2 9/2014 Fodor
8,865,410 B2 10/2014 Shendure
8,906,626 B2 12/2014 Oliphant et al.
8,911,945 B2 12/2014 Van Eijk
8,925,175 B2 1/2015 Aldred et al.
8,936,912 B2 1/2015 Mitra
8,951,726 B2 2/2015 Luo et al.
8,951,728 B2 2/2015 Rasmussen
8,951,781 B2 2/2015 Reed
8,986,926 B2 3/2015 Ferree et al.
9,005,891 B2 4/2015 Sinicropi et al.
9,005,935 B2 4/2015 Belyaev
9,023,768 B2 5/2015 Van Eijk
9,062,348 B1 6/2015 Van Eijk
9,080,210 B2 7/2015 Van Eijk
9,194,001 B2 11/2015 Brenner
9,201,063 B2 12/2015 Sood et al.
9,273,349 B2 3/2016 Nguyen et al.
9,290,808 B2 3/2016 Fodor

(56) References Cited

U.S. PATENT DOCUMENTS

| | | | |
|---|---|---|---|
| 9,290,809 | B2 | 3/2016 | Fodor |
| 9,328,383 | B2 | 5/2016 | Van Eijk |
| 9,330,295 | B2 | 5/2016 | Dunn |
| 9,334,536 | B2 | 5/2016 | Van Eijk |
| 9,371,563 | B2 | 6/2016 | Geiss et al. |
| 9,371,598 | B2 | 6/2016 | Chee |
| 9,376,716 | B2 | 6/2016 | Van Eijk |
| 9,376,717 | B2 | 6/2016 | Gao et al. |
| 9,376,719 | B2 | 6/2016 | Eijk |
| 9,416,409 | B2 | 8/2016 | Hayden |
| 9,447,459 | B2 | 9/2016 | Van Eijk |
| 9,453,256 | B2 | 9/2016 | Van Eijk |
| 9,493,820 | B2 | 11/2016 | Van Eijk |
| 9,506,061 | B2 | 11/2016 | Brown et al. |
| 9,512,422 | B2 | 12/2016 | Barnard et al. |
| 9,557,330 | B2 | 1/2017 | Siciliano et al. |
| 9,574,230 | B2 | 2/2017 | Van Eijk |
| 9,582,877 | B2 | 2/2017 | Fu |
| 9,593,365 | B2 | 3/2017 | Frisen et al. |
| 9,598,728 | B2 | 3/2017 | Barany et al. |
| 9,624,538 | B2 | 4/2017 | Church et al. |
| 9,644,204 | B2 | 5/2017 | Hindson et al. |
| 9,657,335 | B2 | 5/2017 | Van Eijk |
| 9,670,542 | B2 | 6/2017 | Van Eijk |
| 9,694,361 | B2 | 7/2017 | Bharadwaj |
| 9,702,004 | B2 | 7/2017 | Van Eijk |
| 9,714,446 | B2 | 7/2017 | Webster et al. |
| 9,714,937 | B2 | 7/2017 | Dunaway |
| 9,727,810 | B2 | 8/2017 | Fodor et al. |
| 9,745,627 | B2 | 8/2017 | Van Eijk |
| 9,777,324 | B2 | 10/2017 | Van Eijk |
| 9,783,841 | B2 | 10/2017 | Nolan et al. |
| 9,790,476 | B2 | 10/2017 | Gloeckner et al. |
| 9,816,134 | B2 | 11/2017 | Namsaraev |
| 9,834,814 | B2 | 12/2017 | Peter et al. |
| 9,850,536 | B2 | 12/2017 | Oliphant et al. |
| 9,856,521 | B2 | 1/2018 | Stevens et al. |
| 9,868,979 | B2 | 1/2018 | Chee et al. |
| 9,879,313 | B2 | 1/2018 | Chee et al. |
| 9,896,721 | B2 | 2/2018 | Van Eijk |
| 9,898,576 | B2 | 2/2018 | Van Eijk |
| 9,898,577 | B2 | 2/2018 | Van Eijk |
| 9,902,991 | B2 | 2/2018 | Sinicropi et al. |
| 9,909,167 | B2 | 3/2018 | Samusik et al. |
| 9,938,566 | B2 | 4/2018 | Shepard et al. |
| 9,957,550 | B2 | 5/2018 | Yeakley et al. |
| 10,002,316 | B2 | 6/2018 | Fodor et al. |
| 10,023,907 | B2 | 7/2018 | Van Eijk |
| 10,030,261 | B2 | 7/2018 | Frisen et al. |
| 10,035,992 | B2 | 7/2018 | Gloeckner et al. |
| 10,041,949 | B2 | 8/2018 | Bendall et al. |
| 10,059,989 | B2 | 8/2018 | Giresi et al. |
| 10,059,990 | B2 | 8/2018 | Boyden et al. |
| 10,095,832 | B2 | 10/2018 | Van Eijk |
| 10,101,336 | B2 | 10/2018 | Bergo |
| 10,144,966 | B2 | 12/2018 | Cantor |
| 10,208,982 | B2 | 2/2019 | Bannish et al. |
| 10,227,639 | B2 | 3/2019 | Levner et al. |
| 10,273,541 | B2 | 4/2019 | Hindson et al. |
| 10,308,982 | B2 | 6/2019 | Chee |
| 10,317,321 | B2 | 6/2019 | Tillberg et al. |
| 10,357,771 | B2 | 7/2019 | Bharadwaj |
| 10,364,457 | B2 | 7/2019 | Wassie et al. |
| 10,370,698 | B2 | 8/2019 | Nolan et al. |
| 10,415,080 | B2 | 9/2019 | Dunaway et al. |
| 10,465,235 | B2 | 11/2019 | Gullberg et al. |
| 10,472,669 | B2 | 11/2019 | Chee |
| 10,480,022 | B2 | 11/2019 | Chee |
| 10,480,029 | B2 | 11/2019 | Bent et al. |
| 10,494,662 | B2 | 12/2019 | Church et al. |
| 10,494,667 | B2 | 12/2019 | Chee |
| 10,495,554 | B2 | 12/2019 | Deisseroth et al. |
| 10,501,777 | B2 | 12/2019 | Beechem et al. |
| 10,501,791 | B2 | 12/2019 | Church et al. |
| 10,510,435 | B2 | 12/2019 | Cai et al. |
| 10,544,403 | B2 | 1/2020 | Gloeckner et al. |
| 10,550,429 | B2 | 2/2020 | Harada et al. |
| 10,590,244 | B2 | 3/2020 | Delaney et al. |
| 10,633,648 | B2 | 4/2020 | Seelig et al. |
| 10,640,816 | B2 | 5/2020 | Beechem et al. |
| 10,640,826 | B2 | 5/2020 | Church et al. |
| 10,662,466 | B2 | 5/2020 | Berry et al. |
| 10,662,468 | B2 | 5/2020 | Chee |
| 10,669,569 | B2 | 6/2020 | Gullberg et al. |
| 10,724,078 | B2 | 7/2020 | Van Driel et al. |
| 10,725,027 | B2 | 7/2020 | Bell |
| 10,774,372 | B2 | 9/2020 | Chee et al. |
| 10,774,374 | B2 | 9/2020 | Frisen et al. |
| 10,787,701 | B2 | 9/2020 | Chee |
| 10,815,519 | B2 | 10/2020 | Husain et al. |
| 10,829,803 | B2 | 11/2020 | Terbrueggen et al. |
| 10,844,426 | B2 | 11/2020 | Daugharthy et al. |
| 10,858,698 | B2 | 12/2020 | Church et al. |
| 10,858,702 | B2 | 12/2020 | Lucero et al. |
| 10,913,975 | B2 | 2/2021 | So et al. |
| 10,914,730 | B2 | 2/2021 | Chee et al. |
| 10,927,403 | B2 | 2/2021 | Chee et al. |
| 10,961,566 | B2 | 3/2021 | Chee |
| 10,995,361 | B2 | 5/2021 | Chen et al. |
| 11,001,879 | B1 | 5/2021 | Chee |
| 11,008,607 | B2 | 5/2021 | Chee |
| 11,008,608 | B2 | 5/2021 | Samusik et al. |
| 11,046,996 | B1 | 6/2021 | Chee et al. |
| 11,067,567 | B2 | 7/2021 | Chee |
| 11,104,936 | B2 | 8/2021 | Zhang et al. |
| 11,118,216 | B2 | 9/2021 | Koshinsky et al. |
| 11,156,603 | B2 | 10/2021 | Chee |
| 11,162,132 | B2 | 11/2021 | Frisen et al. |
| 11,168,350 | B2 | 11/2021 | Nolan et al. |
| 11,208,684 | B2 | 12/2021 | Chee |
| 11,214,796 | B2 | 1/2022 | Shirai et al. |
| 11,286,515 | B2 | 3/2022 | Chee et al. |
| 11,293,917 | B2 | 4/2022 | Chee |
| 11,299,774 | B2 | 4/2022 | Frisen et al. |
| 11,313,856 | B2 | 4/2022 | Chee |
| 11,332,790 | B2 | 5/2022 | Chell et al. |
| 11,352,659 | B2 | 6/2022 | Frisen et al. |
| 11,352,667 | B2 | 6/2022 | Hauling et al. |
| 11,359,228 | B2 | 6/2022 | Chee et al. |
| 11,365,442 | B2 | 6/2022 | Chee |
| 11,371,086 | B2 | 6/2022 | Chee |
| 11,384,386 | B2 | 7/2022 | Chee |
| 11,390,912 | B2 | 7/2022 | Frisen et al. |
| 11,401,545 | B2 | 8/2022 | Chee |
| 11,407,992 | B2 | 8/2022 | Dadhwal |
| 11,408,029 | B2 | 8/2022 | Katiraee et al. |
| 11,434,524 | B2 | 9/2022 | Ramachandran Iyer et al. |
| 11,447,807 | B2 | 9/2022 | Church et al. |
| 11,459,607 | B1 | 10/2022 | Terry et al. |
| 11,479,809 | B2 | 10/2022 | Frisen et al. |
| 11,479,810 | B1 | 10/2022 | Chee |
| 11,492,612 | B1 | 11/2022 | Dadhwal |
| 11,501,440 | B2 | 11/2022 | Weisenfeld et al. |
| 11,505,828 | B2 | 11/2022 | Chell et al. |
| 11,512,308 | B2 | 11/2022 | Gallant et al. |
| 11,519,022 | B2 | 12/2022 | Chee |
| 11,519,033 | B2 | 12/2022 | Schnall-Levin et al. |
| 11,530,438 | B2 | 12/2022 | Persson et al. |
| 11,535,887 | B2 | 12/2022 | Gallant et al. |
| 11,542,543 | B2 | 1/2023 | Chee |
| 11,549,138 | B2 | 1/2023 | Chee |
| 11,560,587 | B2 | 1/2023 | Chee |
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,649,485 | B2 | 5/2023 | Yin et al. |

(56) References Cited

U.S. PATENT DOCUMENTS

| | | | |
|---|---|---|---|
| 11,661,626 B2 | 5/2023 | Katiraee et al. | |
| 11,680,260 B2 | 6/2023 | Kim et al. | |
| 11,692,218 B2 | 7/2023 | Engblom et al. | |
| 11,702,693 B2 | 7/2023 | Bharadwaj | |
| 11,702,698 B2 | 7/2023 | Stoeckius | |
| 11,713,480 B2 | 8/2023 | Lee | |
| 11,732,292 B2 | 8/2023 | Chee | |
| 11,732,299 B2 | 8/2023 | Ramachandran Iyer | |
| 11,732,300 B2 | 8/2023 | Bava | |
| 11,733,238 B2 | 8/2023 | Chee | |
| 11,739,372 B2 | 8/2023 | Frisen et al. | |
| 11,739,381 B2 | 8/2023 | Chew et al. | |
| 11,753,673 B2 | 9/2023 | Chew et al. | |
| 11,753,674 B2 | 9/2023 | Chee et al. | |
| 11,753,675 B2 | 9/2023 | Ramachandran Iyer | |
| 11,761,030 B2 | 9/2023 | Chee | |
| 11,761,038 B1 | 9/2023 | Stoeckius | |
| 11,767,550 B2 | 9/2023 | Chee | |
| 11,768,175 B1 | 9/2023 | Kim et al. | |
| 11,773,433 B2 | 10/2023 | Gallant et al. | |
| 11,781,130 B2 | 10/2023 | Dadhwal | |
| 11,788,122 B2 | 10/2023 | Frisen et al. | |
| 11,795,498 B2 | 10/2023 | Frisen et al. | |
| 11,795,507 B2 | 10/2023 | Chell et al. | |
| 11,808,769 B2 | 11/2023 | Uytingco et al. | |
| 11,821,024 B2 | 11/2023 | Chee et al. | |
| 11,821,035 B1 | 11/2023 | Bent et al. | |
| 11,827,935 B1 | 11/2023 | Ramachandran Iyer et al. | |
| 11,835,462 B2 | 12/2023 | Bava | |
| 11,840,687 B2 | 12/2023 | Gallant et al. | |
| 11,840,724 B2 | 12/2023 | Chew et al. | |
| 11,845,979 B2 | 12/2023 | Engblom et al. | |
| 11,859,178 B2 | 1/2024 | Gallant et al. | |
| 11,866,767 B2 | 1/2024 | Uytingco et al. | |
| 11,866,770 B2 | 1/2024 | Chee | |
| 11,873,482 B2 | 1/2024 | Kim et al. | |
| 11,891,654 B2 | 2/2024 | Alvarado Martinez et al. | |
| 11,898,205 B2 | 2/2024 | Bava | |
| 11,926,822 B1 | 3/2024 | Gohil et al. | |
| 11,926,863 B1 | 3/2024 | Boutet | |
| 11,926,867 B2 | 3/2024 | Yin et al. | |
| 11,933,957 B1 | 3/2024 | Tentori et al. | |
| 11,952,627 B2 | 4/2024 | Stoeckius | |
| 11,959,076 B2 | 4/2024 | Kim et al. | |
| 11,959,130 B2 | 4/2024 | Galonska et al. | |
| 11,965,213 B2 | 4/2024 | Williams | |
| 11,970,739 B2 | 4/2024 | Chew et al. | |
| 11,981,958 B1 | 5/2024 | Galonska | |
| 11,981,960 B1 | 5/2024 | Lin et al. | |
| 11,981,965 B2 | 5/2024 | Chell et al. | |
| RE50,065 E | 7/2024 | Frisen et al. | |
| 12,024,741 B2 | 7/2024 | Tentori et al. | |
| 12,031,177 B1 | 7/2024 | Tentori et al. | |
| 12,060,604 B2 | 8/2024 | Katiraee et al. | |
| 12,071,655 B2 | 8/2024 | Sukovich et al. | |
| 12,076,701 B2 | 9/2024 | Bava | |
| 12,098,417 B2 | 9/2024 | Engblom et al. | |
| 12,098,985 B2 | 9/2024 | Cox et al. | |
| 12,110,541 B2 | 10/2024 | Bava | |
| 12,117,439 B2 | 10/2024 | Delaney et al. | |
| 12,128,403 B2 | 10/2024 | Kim et al. | |
| 12,129,516 B2 | 10/2024 | Tentori et al. | |
| 12,157,124 B2 | 12/2024 | Cox et al. | |
| 12,180,543 B2 | 12/2024 | Uytingco et al. | |
| 12,195,790 B2 | 1/2025 | Sukovich et al. | |
| 12,203,134 B2 | 1/2025 | Nagendran et al. | |
| 12,209,280 B1 | 1/2025 | Mignardi et al. | |
| 12,223,751 B2 | 2/2025 | Li et al. | |
| 12,228,544 B2 | 2/2025 | Kim et al. | |
| 12,234,505 B2 | 2/2025 | Chee | |
| 12,241,060 B2 | 3/2025 | Kim et al. | |
| 12,241,890 B2 | 3/2025 | Delaney et al. | |
| 12,249,085 B2 | 3/2025 | Tentori et al. | |
| 12,265,079 B1 | 4/2025 | Bent | |
| 12,270,077 B2 | 4/2025 | Schnall-Levin et al. | |
| 12,275,988 B2 | 4/2025 | Galonska et al. | |
| 12,281,357 B1 | 4/2025 | Tentori et al. | |
| 12,286,673 B2 | 4/2025 | Bava | |
| 12,287,264 B2 | 4/2025 | Cox et al. | |
| 12,297,486 B2 | 5/2025 | Patterson et al. | |
| 12,297,487 B2 | 5/2025 | Chee | |
| 12,297,488 B2 | 5/2025 | Chee | |
| 12,344,892 B2 | 7/2025 | Schnall-Levin et al. | |
| 12,365,935 B2 | 7/2025 | Chew et al. | |
| 12,365,942 B2 | 7/2025 | Stoeckius | |
| 12,371,688 B2 | 7/2025 | Kim et al. | |
| 12,378,607 B2 | 8/2025 | Schnall-Levin et al. | |
| 12,385,083 B2 | 8/2025 | Shah | |
| 12,391,979 B2 | 8/2025 | Chee | |
| 12,391,980 B2 | 8/2025 | Chee | |
| 12,399,123 B1 | 8/2025 | Shah et al. | |
| 12,404,544 B2 | 9/2025 | Tentori et al. | |
| 12,405,264 B2 | 9/2025 | Stoeckius | |
| 12,416,603 B2 | 9/2025 | Tentori et al. | |
| 12,435,363 B1 | 10/2025 | Gallant et al. | |
| 12,442,045 B2 | 10/2025 | Williams | |
| 12,497,654 B2 | 12/2025 | Ramachandran Iyer et al. | |
| 12,508,590 B2 | 12/2025 | Kim et al. | |
| D1,108,656 S | 1/2026 | Alimsijah et al. | |
| 12,529,094 B2 | 1/2026 | Bent et al. | |
| 12,545,949 B2 | 2/2026 | Bent et al. | |
| 12,553,805 B2 | 2/2026 | Shahjamali | |
| 12,553,898 B1 | 2/2026 | Uytingco et al. | |
| 12,566,113 B2 | 3/2026 | Delaney et al. | |
| 12,566,114 B2 | 3/2026 | Cox et al. | |
| 12,571,029 B1 | 3/2026 | Galonska et al. | |
| 12,668,835 B1 | 6/2026 | Tentori et al. | |
| 12,692,492 B2 | 7/2026 | Gallant et al. | |
| 2001/0055764 A1 | 12/2001 | Empendocles et al. | |
| 2002/0040275 A1 | 4/2002 | Cravatt | |
| 2002/0051986 A1 | 5/2002 | Baez et al. | |
| 2002/0055100 A1 | 5/2002 | Kawashima | |
| 2002/0058250 A1 | 5/2002 | Firth | |
| 2002/0086441 A1 | 7/2002 | Baranov et al. | |
| 2002/0146745 A1 | 10/2002 | Natan et al. | |
| 2002/0150909 A1 | 10/2002 | Stuelpnagel | |
| 2002/0164611 A1 | 11/2002 | Bamdad | |
| 2003/0017451 A1 | 1/2003 | Wang et al. | |
| 2003/0022207 A1 | 1/2003 | Balasubramanian | |
| 2003/0040035 A1 | 2/2003 | Slamon | |
| 2003/0064398 A1 | 4/2003 | Barnes | |
| 2003/0092624 A1 | 5/2003 | Wang et al. | |
| 2003/0138879 A1 | 7/2003 | Lambalot | |
| 2003/0148335 A1 | 8/2003 | Shen et al. | |
| 2003/0162216 A1 | 8/2003 | Gold | |
| 2003/0165948 A1 | 9/2003 | Alsmadi et al. | |
| 2003/0175844 A1 | 9/2003 | Nadler et al. | |
| 2003/0211489 A1 | 11/2003 | Shen et al. | |
| 2003/0215936 A1 | 11/2003 | Kallioniemi et al. | |
| 2003/0224419 A1 | 12/2003 | Corcoran | |
| 2003/0231983 A1 | 12/2003 | Schleifer | |
| 2003/0232348 A1 | 12/2003 | Jones et al. | |
| 2003/0232382 A1 | 12/2003 | Brennan | |
| 2003/0235854 A1 | 12/2003 | Chan et al. | |
| 2004/0009487 A1 | 1/2004 | Kadushin et al. | |
| 2004/0033499 A1 | 2/2004 | Ilsley et al. | |
| 2004/0067492 A1 | 4/2004 | Peng et al. | |
| 2004/0082058 A1 | 4/2004 | Schleifer et al. | |
| 2004/0082059 A1 | 4/2004 | Webb et al. | |
| 2004/0096853 A1 | 5/2004 | Mayer | |
| 2004/0101835 A1 | 5/2004 | Willis et al. | |
| 2004/0106110 A1 | 6/2004 | Balasubramanian | |
| 2004/0112442 A1 | 6/2004 | Maerkl | |
| 2004/0235103 A1 | 11/2004 | Reznikoff et al. | |
| 2004/0241660 A1 | 12/2004 | Wojtowicz et al. | |
| 2004/0248287 A1 | 12/2004 | Hu et al. | |
| 2004/0248325 A1 | 12/2004 | Bukusoglu et al. | |
| 2004/0259105 A1 | 12/2004 | Fan et al. | |
| 2005/0003431 A1 | 1/2005 | Wucherpfennig | |
| 2005/0014203 A1 | 1/2005 | Darfler et al. | |
| 2005/0037393 A1 | 2/2005 | Gunderson et al. | |
| 2005/0048498 A1 | 3/2005 | Woudenberg et al. | |
| 2005/0048580 A1 | 3/2005 | Labaer | |
| 2005/0064460 A1 | 3/2005 | Holliger et al. | |

(56) References Cited

U.S. PATENT DOCUMENTS

| | | | |
|---|---|---|---|
| 2005/0095627 | A1 | 5/2005 | Kolman et al. |
| 2005/0100900 | A1 | 5/2005 | Kawashima et al. |
| 2005/0106617 | A1 | 5/2005 | Besemer et al. |
| 2005/0116161 | A1 | 6/2005 | Hafeman et al. |
| 2005/0130173 | A1 | 6/2005 | Leamon et al. |
| 2005/0136414 | A1 | 6/2005 | Gunderson et al. |
| 2005/0164292 | A1 | 7/2005 | Farooqui |
| 2005/0170373 | A1 | 8/2005 | Monforte |
| 2005/0179746 | A1 | 8/2005 | Roux et al. |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0239119 | A1 | 10/2005 | Tsukada et al. |
| 2005/0260653 | A1 | 11/2005 | LaBaer |
| 2005/0266417 | A1 | 12/2005 | Barany et al. |
| 2006/0041385 | A1 | 2/2006 | Bauer et al. |
| 2006/0046313 | A1 | 3/2006 | Roth |
| 2006/0084078 | A1 | 4/2006 | Zhao |
| 2006/0105352 | A1 | 5/2006 | Qiao et al. |
| 2006/0154286 | A1 | 7/2006 | Kong et al. |
| 2006/0164490 | A1 | 7/2006 | Kim et al. |
| 2006/0188901 | A1 | 8/2006 | Barnes et al. |
| 2006/0199183 | A1 | 9/2006 | Valat et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0275782 | A1 | 12/2006 | Gunderson et al. |
| 2006/0281109 | A1 | 12/2006 | Barr Ost et al. |
| 2007/0020640 | A1 | 1/2007 | McCloskey et al. |
| 2007/0020669 | A1 | 1/2007 | Ericsson |
| 2007/0026430 | A1 | 2/2007 | Andersen et al. |
| 2007/0054288 | A1 | 3/2007 | Su et al. |
| 2007/0087360 | A1 | 4/2007 | Boyd |
| 2007/0099208 | A1 | 5/2007 | Drmanac et al. |
| 2007/0116612 | A1 | 5/2007 | Williamson |
| 2007/0128071 | A1 | 6/2007 | Shea et al. |
| 2007/0128624 | A1 | 6/2007 | Gormley et al. |
| 2007/0128656 | A1 | 6/2007 | Agrawal |
| 2007/0134723 | A1 | 6/2007 | Kozlov et al. |
| 2007/0161020 | A1 | 7/2007 | Luo et al. |
| 2007/0166705 | A1 | 7/2007 | Milton et al. |
| 2007/0172873 | A1 | 7/2007 | Brenner et al. |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0003586 | A1 | 1/2008 | Hyde et al. |
| 2008/0009420 | A1 | 1/2008 | Schroth et al. |
| 2008/0108082 | A1 | 5/2008 | Rank et al. |
| 2008/0108804 | A1 | 5/2008 | Hayashizaki et al. |
| 2008/0132429 | A1 | 6/2008 | Perov et al. |
| 2008/0145616 | A1 | 6/2008 | Gharib et al. |
| 2008/0160580 | A1 | 7/2008 | Adessi et al. |
| 2008/0218838 | A1 | 9/2008 | Rey-Mermet |
| 2008/0220434 | A1 | 9/2008 | Thomas |
| 2008/0261204 | A1 | 10/2008 | Lexow |
| 2008/0286795 | A1 | 11/2008 | Kawashima et al. |
| 2008/0293046 | A1 | 11/2008 | Allawi et al. |
| 2009/0005252 | A1 | 1/2009 | Drmanac et al. |
| 2009/0006002 | A1 | 1/2009 | Honisch et al. |
| 2009/0018024 | A1 | 1/2009 | Church et al. |
| 2009/0026082 | A1 | 1/2009 | Rothberg et al. |
| 2009/0036323 | A1 | 2/2009 | van Eijk et al. |
| 2009/0068667 | A1 | 3/2009 | Meisner et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0170713 | A1 | 7/2009 | van Eijk et al. |
| 2009/0202998 | A1 | 8/2009 | Schlumpberger et al. |
| 2009/0233802 | A1 | 9/2009 | Bignell et al. |
| 2009/0253581 | A1 | 10/2009 | van Eijk et al. |
| 2009/0270273 | A1 | 10/2009 | Burns et al. |
| 2009/0283407 | A1 | 11/2009 | Shah et al. |
| 2009/0286249 | A1 | 11/2009 | Becker et al. |
| 2009/0291854 | A1 | 11/2009 | Weisinger-Mayr et al. |
| 2009/0312193 | A1 | 12/2009 | Kim et al. |
| 2009/0321262 | A1 | 12/2009 | Adachi et al. |
| 2010/0031757 | A1 | 2/2010 | Hoyer |
| 2010/0035249 | A1 | 2/2010 | Hayashizaki et al. |
| 2010/0047790 | A1 | 2/2010 | Southern et al. |
| 2010/0069263 | A1 | 3/2010 | Shendure et al. |
| 2010/0105052 | A1 | 4/2010 | Drmanac et al. |
| 2010/0120043 | A1 | 5/2010 | Sood et al. |
| 2010/0120097 | A1 | 5/2010 | Matz et al. |
| 2010/0120098 | A1 | 5/2010 | Grunenwald et al. |
| 2010/0129874 | A1 | 5/2010 | Mitra et al. |
| 2010/0145037 | A1 | 6/2010 | Brive et al. |
| 2010/0173384 | A1 | 7/2010 | Johnsson et al. |
| 2010/0184618 | A1 | 7/2010 | Namsaraev et al. |
| 2010/0210475 | A1 | 8/2010 | Lee et al. |
| 2010/0227329 | A1 | 9/2010 | Cuppens |
| 2010/0273219 | A1 | 10/2010 | May et al. |
| 2010/0282617 | A1 | 11/2010 | Rothberg et al. |
| 2011/0028685 | A1 | 2/2011 | Purkayastha et al. |
| 2011/0031123 | A1 | 2/2011 | Schulze et al. |
| 2011/0033854 | A1 | 2/2011 | Drmanac et al. |
| 2011/0045462 | A1 | 2/2011 | Fu et al. |
| 2011/0059436 | A1 | 3/2011 | Hardin et al. |
| 2011/0111409 | A1 | 5/2011 | Sinicropi et al. |
| 2011/0152111 | A1 | 6/2011 | Fan et al. |
| 2011/0237449 | A1 | 9/2011 | McMaster et al. |
| 2011/0245101 | A1 | 10/2011 | Chee et al. |
| 2011/0245111 | A1 | 10/2011 | Chee |
| 2011/0269631 | A1 | 11/2011 | Fu et al. |
| 2011/0287435 | A1 | 11/2011 | Grunenwald et al. |
| 2012/0004140 | A1 | 1/2012 | Staker |
| 2012/0021930 | A1 | 1/2012 | Schoen et al. |
| 2012/0046175 | A1 | 2/2012 | Rodesch et al. |
| 2012/0046178 | A1 | 2/2012 | Van Den Boom et al. |
| 2012/0065081 | A1 | 3/2012 | Chee |
| 2012/0135871 | A1 | 5/2012 | van Eijk et al. |
| 2012/0177543 | A1 | 7/2012 | Battrell |
| 2012/0202698 | A1 | 8/2012 | van Eijk et al. |
| 2012/0202704 | A1 | 8/2012 | Fan et al. |
| 2012/0220479 | A1 | 8/2012 | Ericsson et al. |
| 2012/0245053 | A1 | 9/2012 | Shirai et al. |
| 2012/0252702 | A1 | 10/2012 | Muratani et al. |
| 2012/0258871 | A1 | 10/2012 | Kozlov et al. |
| 2012/0289414 | A1 | 11/2012 | Mitra et al. |
| 2012/0301925 | A1 | 11/2012 | Belyaev |
| 2013/0005594 | A1 | 1/2013 | Terbrueggen et al. |
| 2013/0005600 | A1 | 1/2013 | Olek |
| 2013/0023433 | A1 | 1/2013 | Luo et al. |
| 2013/0035239 | A1 | 2/2013 | Kong et al. |
| 2013/0040842 | A1 | 2/2013 | Lim et al. |
| 2013/0052331 | A1 | 2/2013 | Kram et al. |
| 2013/0053273 | A1 | 2/2013 | Juncker et al. |
| 2013/0065768 | A1 | 3/2013 | Zheng et al. |
| 2013/0079232 | A1 | 3/2013 | Kain et al. |
| 2013/0096033 | A1 | 4/2013 | Routenberg |
| 2013/0171621 | A1 | 7/2013 | Luo et al. |
| 2013/0244884 | A1 | 9/2013 | Jacobson et al. |
| 2013/0252847 | A1 | 9/2013 | McKenna et al. |
| 2013/0261019 | A1 | 10/2013 | Lin et al. |
| 2013/0302801 | A1 | 11/2013 | Asbury et al. |
| 2013/0338042 | A1 | 12/2013 | Shen et al. |
| 2014/0011707 | A1 | 1/2014 | Ye et al. |
| 2014/0066318 | A1 | 3/2014 | Frisen et al. |
| 2014/0121118 | A1 | 5/2014 | Warner |
| 2014/0270435 | A1 | 9/2014 | Dunn |
| 2014/0274731 | A1 | 9/2014 | Raymond et al. |
| 2014/0323330 | A1 | 10/2014 | Glezer et al. |
| 2014/0342921 | A1 | 11/2014 | Weiner |
| 2014/0378350 | A1 | 12/2014 | Hindson et al. |
| 2015/0017635 | A1 | 1/2015 | Myllykangas et al. |
| 2015/0148239 | A1 | 5/2015 | Jon |
| 2015/0219618 | A1 | 8/2015 | Krishnan et al. |
| 2015/0253225 | A1 | 9/2015 | Ng et al. |
| 2015/0292988 | A1 | 10/2015 | Bharadwaj et al. |
| 2015/0344942 | A1 | 12/2015 | Frisen et al. |

(56) References Cited

U.S. PATENT DOCUMENTS

2016/0003718 A1 1/2016 Ikushima et al.
2016/0019337 A1 1/2016 Roberts et al.
2016/0024576 A1 1/2016 Chee
2016/0033496 A1 2/2016 Chou et al.
2016/0041159 A1 2/2016 Labaer et al.
2016/0060687 A1 3/2016 Zhu et al.
2016/0108458 A1 4/2016 Frei et al.
2016/0122817 A1 5/2016 Jarosz et al.
2016/0138091 A1 5/2016 Chee et al.
2016/0145677 A1 5/2016 Chee et al.
2016/0157838 A1 6/2016 Tatnell et al.
2016/0194692 A1 7/2016 Gore et al.
2016/0201125 A1 7/2016 Samuels et al.
2016/0253584 A1 9/2016 Fodor et al.
2016/0289740 A1 10/2016 Fu et al.
2016/0298180 A1 10/2016 Chee
2016/0299165 A1 10/2016 Zhou
2016/0305856 A1 10/2016 Boyden et al.
2016/0312276 A1 10/2016 Fu et al.
2016/0333403 A1 11/2016 Chee
2016/0376642 A1 12/2016 Landegren et al.
2017/0009278 A1 1/2017 Söderberg et al.
2017/0016053 A1 1/2017 Beechem et al.
2017/0058339 A1 3/2017 Chee
2017/0058340 A1 3/2017 Chee
2017/0058345 A1 3/2017 Chee
2017/0088881 A1 3/2017 Chee
2017/0159109 A1 6/2017 Zheng et al.
2017/0166962 A1 6/2017 van Eijk et al.
2017/0220733 A1 8/2017 Zhuang et al.
2017/0233722 A1 8/2017 Seelig et al.
2017/0275669 A1 9/2017 Weissleder et al.
2017/0283860 A1 10/2017 Kool et al.
2017/0335297 A1 11/2017 Ha et al.
2017/0335410 A1 11/2017 Driscoll et al.
2017/0342405 A1 11/2017 Fu et al.
2017/0349940 A1 12/2017 Morin et al.
2018/0057873 A1 3/2018 Zhou et al.
2018/0080019 A1 3/2018 Blainey et al.
2018/0088112 A1 3/2018 Fan et al.
2018/0094316 A1 4/2018 Oliphant et al.
2018/0095067 A1 4/2018 Huff et al.
2018/0104694 A1 4/2018 Huff et al.
2018/0104964 A1 4/2018 Uemura et al.
2018/0112261 A1 4/2018 Van Driel et al.
2018/0127817 A1 5/2018 Borchert et al.
2018/0163265 A1 6/2018 Zhang et al.
2018/0179591 A1 6/2018 van Eijk
2018/0201925 A1 7/2018 Steemers et al.
2018/0201980 A1 7/2018 Chee et al.
2018/0208967 A1 7/2018 Larman et al.
2018/0216161 A1 8/2018 Chen et al.
2018/0216162 A1 8/2018 Belhocine et al.
2018/0217094 A1 8/2018 Herr et al.
2018/0237864 A1 8/2018 Imler et al.
2018/0245142 A1 8/2018 So et al.
2018/0247017 A1 8/2018 van Eijk et al.
2018/0291427 A1 10/2018 Edelman
2018/0291439 A1 10/2018 van Eijk et al.
2018/0305681 A1 10/2018 Jovanovich et al.
2018/0312822 A1 11/2018 Lee et al.
2018/0320226 A1 11/2018 Church et al.
2018/0334670 A1 11/2018 Bharadwaj et al.
2019/0032128 A1 1/2019 Chen et al.
2019/0055594 A1 2/2019 Samusik et al.
2019/0064173 A1 2/2019 Bharadwaj et al.
2019/0071656 A1 3/2019 Chang et al.
2019/0085383 A1 3/2019 Church et al.
2019/0119735 A1 4/2019 Deisseroth et al.
2019/0135774 A1 5/2019 Orbai
2019/0145982 A1 5/2019 Chee et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0201891 A1 7/2019 Pallas et al.
2019/0203275 A1 7/2019 Frisen et al.
2019/0218276 A1 7/2019 Regev et al.
2019/0218608 A1 7/2019 Daugharthy et al.
2019/0233878 A1 8/2019 Delaney et al.
2019/0233880 A1 8/2019 Mir
2019/0249226 A1 8/2019 Bent et al.
2019/0249248 A1 8/2019 Beechem et al.
2019/0262831 A1 8/2019 West et al.
2019/0264268 A1 8/2019 Frisen et al.
2019/0271028 A1 9/2019 Khafizov et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0330617 A1 10/2019 Church et al.
2019/0338353 A1 11/2019 Belgrader et al.
2019/0352708 A1 11/2019 Gaige et al.
2019/0360034 A1 11/2019 Zhou et al.
2019/0360043 A1 11/2019 Pham et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0010891 A1 1/2020 Beechem et al.
2020/0024641 A1 1/2020 Nolan et al.
2020/0040376 A1 2/2020 Russel et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0080136 A1 3/2020 Zhang et al.
2020/0109443 A1 4/2020 Chee
2020/0123597 A1 4/2020 Daniel
2020/0131570 A1 4/2020 Berti et al.
2020/0140920 A1 5/2020 Pierce et al.
2020/0173985 A1 6/2020 Dong et al.
2020/0199565 A1 6/2020 Chen et al.
2020/0199572 A1 6/2020 Kuersten et al.
2020/0224244 A1 7/2020 Nilsson et al.
2020/0239874 A1 7/2020 Mikkelsen
2020/0239946 A1 7/2020 Dewal
2020/0256867 A1 8/2020 Hennek et al.
2020/0277663 A1 9/2020 Iyer
2020/0277664 A1 9/2020 Frenz
2020/0283852 A1 9/2020 Oliphant et al.
2020/0299757 A1 9/2020 Chee et al.
2020/0325531 A1 10/2020 Chee
2020/0362398 A1 11/2020 Kishi et al.
2020/0363408 A1 11/2020 Chou et al.
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0017587 A1 1/2021 Cai et al.
2021/0095331 A1 4/2021 Fan et al.
2021/0115504 A1 4/2021 Cai et al.
2021/0123040 A1 4/2021 Macosko et al.
2021/0130881 A1 5/2021 Cox
2021/0140982 A1 5/2021 Uytingco et al.
2021/0150707 A1 5/2021 Weisenfeld et al.
2021/0155982 A1 5/2021 Yin et al.
2021/0158522 A1 5/2021 Weisenfeld et al.
2021/0172007 A1 6/2021 Chee et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee

(56) References Cited

U.S. PATENT DOCUMENTS

2021/0214785 A1 7/2021 Stoeckius
2021/0222235 A1 7/2021 Chee
2021/0222241 A1 7/2021 Bharadwaj
2021/0222242 A1 7/2021 Ramachandran Iyer
2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0246492 A1 8/2021 Song et al.
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee
2021/0277460 A1 9/2021 Bava
2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0317524 A1 10/2021 Lucero et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0064630 A1 3/2022 Bent et al.
2022/0081728 A1 3/2022 Williams
2022/0090058 A1 3/2022 Frisen et al.
2022/0090175 A1 3/2022 Uytingco et al.
2022/0098576 A1 3/2022 Dadhwal
2022/0098661 A1 3/2022 Chew et al.
2022/0106632 A1 4/2022 Galonska et al.
2022/0106633 A1 4/2022 Engblom et al.
2022/0112486 A1 4/2022 Ramachandran Iyer et al.
2022/0112545 A1 4/2022 Chee
2022/0119869 A1 4/2022 Ramachandran Iyer et al.
2022/0127659 A1 4/2022 Frisen et al.
2022/0127666 A1 4/2022 Katiraee et al.
2022/0127672 A1 4/2022 Stoeckius
2022/0145361 A1 5/2022 Frenz et al.
2022/0154255 A1 5/2022 Chee et al.
2022/0170083 A1 6/2022 Khaled et al.
2022/0195422 A1 6/2022 Gallant et al.
2022/0195505 A1 6/2022 Frisen et al.
2022/0196644 A1 6/2022 Chee
2022/0213526 A1 7/2022 Frisen et al.
2022/0220544 A1 7/2022 Ach et al.
2022/0241780 A1 8/2022 Tentori et al.
2022/0267844 A1 8/2022 Ramachandran Iyer et al.
2022/0282329 A1 9/2022 Chell et al.
2022/0290217 A1 9/2022 Frenz et al.
2022/0290219 A1 9/2022 Chee
2022/0298560 A1 9/2022 Frisen et al.
2022/0325325 A1 10/2022 Chee et al.
2022/0326251 A1 10/2022 Uytingco et al.
2022/0333171 A1 10/2022 Chee
2022/0333191 A1 10/2022 Mikkelsen et al.
2022/0333192 A1 10/2022 Uytingco
2022/0333195 A1 10/2022 Schnall-Levin et al.
2022/0334031 A1 10/2022 Delaney et al.
2022/0348905 A1 11/2022 Dadhwal
2022/0348992 A1 11/2022 Stoeckius et al.
2022/0356464 A1 11/2022 Kim et al.
2022/0364163 A1 11/2022 Stahl et al.
2022/0389491 A1 12/2022 Chee
2022/0389503 A1 12/2022 Mikkelsen et al.
2022/0389504 A1 12/2022 Chew et al.
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0017773 A1 1/2023 Kim et al.
2023/0031305 A1 2/2023 Hernandez Neuta et al.
2023/0033960 A1 2/2023 Gallant et al.
2023/0034039 A1 2/2023 Shahjamali
2023/0034216 A1 2/2023 Bava
2023/0040363 A1 2/2023 Chee
2023/0042088 A1 2/2023 Chee
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0107023 A1 4/2023 Chee
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0151412 A1 5/2023 Chee
2023/0159994 A1 5/2023 Chee
2023/0159995 A1 5/2023 Iyer et al.
2023/0160008 A1 5/2023 Chell et al.
2023/0175045 A1 6/2023 Katsori et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0212655 A1 7/2023 Chee
2023/0212656 A1 7/2023 Chow et al.
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0267625 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304072 A1 9/2023 Gohil et al.
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323436 A1 10/2023 Chee
2023/0323447 A1 10/2023 Schnall-Levin et al.
2023/0323453 A1 10/2023 Stoeckius
2023/0332138 A1 10/2023 Kim et al.
2023/0332211 A1 10/2023 Chee

(56) References Cited

U.S. PATENT DOCUMENTS

2023/0332212 A1 10/2023 Chew et al.
2023/0332227 A1 10/2023 Ramachandran Iyer
2023/0332247 A1 10/2023 Singh et al.
2023/0351619 A1 11/2023 Tentori et al.
2023/0358733 A1 11/2023 Chee
2023/0366008 A1 11/2023 Chew et al.
2023/0383285 A1 11/2023 Kim et al.
2023/0383344 A1 11/2023 Stoeckius
2023/0392204 A1 12/2023 Chell et al.
2023/0393071 A1 12/2023 Bava
2023/0407404 A1 12/2023 Baumgartner et al.
2023/0416807 A1 12/2023 Chee
2023/0416808 A1 12/2023 Sukovich et al.
2023/0416850 A1 12/2023 Singh et al.
2024/0002931 A1 1/2024 Bava
2024/0011081 A1 1/2024 Chee
2024/0011090 A1 1/2024 Chew et al.
2024/0018572 A1 1/2024 Mignardi
2024/0018575 A1 1/2024 Gallant et al.
2024/0018589 A1 1/2024 Schnall-Levin et al.
2024/0026445 A1 1/2024 Ramachandran Iyer et al.
2024/0033743 A1 2/2024 Tentori et al.
2024/0035937 A1 2/2024 Cox et al.
2024/0043908 A1 2/2024 Chew et al.
2024/0043925 A1 2/2024 Bent et al.
2024/0052343 A1 2/2024 Gallant et al.
2024/0053351 A1 2/2024 Uytingco et al.
2024/0060115 A1 2/2024 Chee et al.
2024/0067953 A1 2/2024 Mikkelsen et al.
2024/0068016 A1 2/2024 Frisen et al.
2024/0068017 A1 2/2024 Lundeberg et al.
2024/0076723 A1 3/2024 Mignardi
2024/0080346 A1 3/2024 Engblom et al.
2024/0084365 A1 3/2024 Frisen et al.
2024/0084366 A1 3/2024 Chee
2024/0084383 A1 3/2024 Ramachandran Iyer et al.
2024/0093274 A1 3/2024 Frisen et al.
2024/0093290 A1 3/2024 Stahl et al.
2024/0110228 A1 4/2024 Uytingco et al.
2024/0124933 A1 4/2024 Chell et al.
2024/0125772 A1 4/2024 Delaney et al.
2024/0141327 A1 5/2024 Kim et al.
2024/0158838 A1 5/2024 Alvarado Martinez et al.
2024/0175080 A1 5/2024 Galonska et al.
2024/0182968 A1 6/2024 Bava
2024/0191286 A1 6/2024 Boutet et al.
2024/0200121 A1 6/2024 Boutet
2024/0209425 A1 6/2024 Yin et al.
2024/0218432 A1 7/2024 Mielinis
2024/0219701 A1 7/2024 Tentori et al.
2024/0253036 A1 8/2024 Kim et al.
2024/0263218 A1 8/2024 Katiraee et al.
2024/0271190 A1 8/2024 Stoeckius et al.
2024/0271195 A1 8/2024 Mikhaiel et al.
2024/0279712 A1 8/2024 Fan et al.
2024/0279747 A1 8/2024 Williams
2024/0287600 A1 8/2024 Iyer et al.
2024/0294971 A1 9/2024 Galonska
2024/0294974 A1 9/2024 Galonska et al.
2024/0294975 A1 9/2024 Lin et al.
2024/0301488 A1 9/2024 Stoeckius
2024/0301489 A1 9/2024 Chew et al.
2024/0360494 A1 10/2024 Costa et al.
2024/0368711 A1 11/2024 Giacomello et al.
2024/0377297 A1 11/2024 Cox et al.
2024/0385088 A1 11/2024 Kim et al.
2024/0392349 A1 11/2024 Frisen et al.
2024/0392351 A1 11/2024 Chee
2024/0392352 A1 11/2024 Stahl et al.
2024/0392353 A1 11/2024 Engblom et al.
2024/0401109 A1 12/2024 Kim et al.
2024/0401117 A1 12/2024 Bava
2024/0401118 A1 12/2024 Tentori et al.
2024/0404301 A1 12/2024 Li et al.
2024/0408593 A1 12/2024 Kim et al.
2024/0416315 A1 12/2024 Bava
2024/0417783 A1 12/2024 Chew et al.
2024/0417784 A1 12/2024 Sukovich et al.
2025/0002980 A1 1/2025 Tentori et al.
2025/0002982 A1 1/2025 Stoeckius et al.
2025/0003956 A1 1/2025 Delaney et al.
2025/0019689 A1 1/2025 Galonska et al.
2025/0019749 A1 1/2025 Katiraee et al.
2025/0066762 A1 2/2025 Man et al.
2025/0066770 A1 2/2025 Costa
2025/0073719 A1 3/2025 Cox et al.
2025/0075261 A1 3/2025 Kim
2025/0101501 A1 3/2025 Chee
2025/0101502 A1 3/2025 Chee
2025/0101504 A1 3/2025 Nagendran et al.
2025/0122564 A1 4/2025 Mignardi et al.
2025/0122565 A1 4/2025 Schnall-Levin et al.
2025/0129412 A1 4/2025 Uytingco et al.
2025/0129421 A1 4/2025 Schnall-Levin et al.
2025/0137043 A1 5/2025 Tentori
2025/0145984 A1 5/2025 Ma et al.
2025/0146057 A1 5/2025 Schnall-Levin et al.
2025/0146058 A1 5/2025 Tentori
2025/0146071 A1 5/2025 Schnall-Levin et al.
2025/0146072 A1 5/2025 Schnall-Levin et al.
2025/0154565 A1 5/2025 Chee
2025/0154566 A1 5/2025 Chee
2025/0154567 A1 5/2025 Chee
2025/0154568 A1 5/2025 Frisen et al.
2025/0154569 A1 5/2025 Stoeckius et al.
2025/0154571 A1 5/2025 Ramachandran Iyer et al.
2025/0154588 A1 5/2025 Ramachandran Iyer et al.
2025/0155446 A1 5/2025 Uytingco et al.
2025/0163501 A1 5/2025 Singh et al.
2025/0163509 A1 5/2025 Daugharthy et al.
2025/0171833 A1 5/2025 Frisen et al.
2025/0171848 A1 5/2025 Chell et al.
2025/0179475 A1 6/2025 Borgstrom et al.
2025/0182305 A1 6/2025 Tentori et al.
2025/0182503 A1 6/2025 Li et al.
2025/0188526 A1 6/2025 Sukovich et al.
2025/0189483 A1 6/2025 Kim et al.
2025/0197847 A1 6/2025 Kim et al.
2025/0197938 A1 6/2025 Bjorninen
2025/0207125 A1 6/2025 Gupta et al.
2025/0207182 A1 6/2025 Chee
2025/0207183 A1 6/2025 Chee
2025/0207195 A1 6/2025 Chell et al.
2025/0208115 A1 6/2025 Bent
2025/0215482 A1 7/2025 Mignardi et al.
2025/0215484 A1 7/2025 Ramachandran Iyer et al.
2025/0216300 A1 7/2025 Delaney et al.
2025/0216303 A1 7/2025 Cox et al.
2025/0223633 A1 7/2025 Frenz et al.
2025/0230487 A1 7/2025 Chee et al.
2025/0230498 A1 7/2025 Katiraee
2025/0250621 A1 8/2025 Galonska et al.
2025/0250632 A1 8/2025 Mignardi et al.
2025/0257393 A1 8/2025 Katiraee et al.
2025/0263791 A1 8/2025 Bava
2025/0264411 A1 8/2025 Bava
2025/0283154 A1 9/2025 Iyer et al.
2025/0283157 A1 9/2025 Uytingco et al.
2025/0297308 A1 9/2025 Tentori
2025/0313890 A1 10/2025 Lundeberg et al.
2025/0313892 A1 10/2025 Stoeckius
2025/0340932 A1 11/2025 Chee
2025/0340933 A1 11/2025 Giacomello et al.
2025/0354931 A1 11/2025 Shah et al.
2025/0369037 A1 12/2025 Gupta
2025/0376676 A1 12/2025 Kim et al.
2025/0376719 A1 12/2025 Shah
2025/0382665 A1 12/2025 Frenz et al.
2026/0002202 A1 1/2026 Schnall-Levin et al.
2026/0009784 A1 1/2026 Stoeckius
2026/0015653 A1 1/2026 Chew et al.
2026/0022419 A1 1/2026 Bent et al.
2026/0035740 A1 2/2026 Chee
2026/0049349 A1 2/2026 Gallant et al.

(56) References Cited

U.S. PATENT DOCUMENTS

| | | | |
|---|---|---|---|
| 2026/0055443 | A1 | 2/2026 | Tentori et al. |
| 2026/0071262 | A1 | 3/2026 | Yin et al. |
| 2026/0103754 | A1 | 4/2026 | Schnall-Levin et al. |
| 2026/0117286 | A1 | 4/2026 | Katiraee et al. |
| 2026/0117289 | A1 | 4/2026 | Kim |
| 2026/0117298 | A1 | 4/2026 | Doddridge |
| 2026/0117302 | A1 | 4/2026 | Chell et al. |
| 2026/0124615 | A1 | 5/2026 | Kim et al. |
| 2026/0132449 | A1 | 5/2026 | Galonska et al. |
| 2026/0132451 | A1 | 5/2026 | Ramachandran Iyer et al. |
| 2026/0146280 | A1 | 5/2026 | Kuhnemund et al. |
| 2026/0176690 | A1 | 6/2026 | Schnall-Levin et al. |
| 2026/0177299 | A1 | 6/2026 | Schroeder et al. |
| 2026/0185146 | A1 | 7/2026 | Tentori et al. |
| 2026/0185147 | A1 | 7/2026 | Tentori et al. |
| 2026/0201453 | A1 | 7/2026 | Schnall-Levin et al. |
| 2026/0209833 | A1 | 7/2026 | Katiraee |
| 2026/0242851 | A1 | 8/2026 | Mikhaiel et al. |

FOREIGN PATENT DOCUMENTS

| | | |
|---|---|---|
| CN | 1273609 | 11/2000 |
| CN | 1537953 | 10/2004 |
| CN | 1680604 | 10/2005 |
| CN | 1749752 | 3/2006 |
| CN | 1898398 | 1/2007 |
| CN | 1981188 | 6/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 0961110 | 12/1999 |
| EP | 0901631 | 8/2004 |
| EP | 1712623 | 10/2006 |
| EP | 1782737 | 5/2007 |
| EP | 1878502 | 1/2008 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013983 | 5/2016 |
| EP | 3013984 | 5/2016 |
| EP | 2350648 | 7/2017 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2004/087323 | 10/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/056861 | 6/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2008/157801 | 12/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/019964 | 2/2011 |
| WO | WO 2011/062933 | 5/2011 |
| WO | WO 2011/068088 | 6/2011 |
| WO | WO 2011/102903 | 8/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/192292 | 12/2013 |
| WO | WO 2014/044724 | 3/2014 |
| WO | WO 2014/060483 | 4/2014 |
| WO | WO 2014/066179 | 5/2014 |
| WO | WO 2014/071361 | 5/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/200767 | 12/2014 |
| WO | WO 2014/210223 | 12/2014 |
| WO | WO 2014/210353 | 12/2014 |
| WO | WO 2015/031691 | 3/2015 |
| WO | WO 2015/057319 | 4/2015 |
| WO | WO 2015/069374 | 5/2015 |
| WO | WO 2015/094861 | 6/2015 |
| WO | WO 2015/122967 | 8/2015 |
| WO | WO 2015/161173 | 10/2015 |
| WO | WO 2016/057552 | 4/2016 |
| WO | WO 2016/077763 | 5/2016 |

(56) References Cited

FOREIGN PATENT DOCUMENTS

WO WO 2016/100196 6/2016
WO WO 2016/138496 9/2016
WO WO 2016/138500 9/2016
WO WO 2016/162309 10/2016
WO WO 2016/166128 10/2016
WO WO 2016/168825 10/2016
WO WO 2016/172362 10/2016
WO WO 2017/019456 2/2017
WO WO 2017/019481 2/2017
WO WO 2017/027367 2/2017
WO WO 2017/044993 3/2017
WO WO 2017/048871 3/2017
WO WO 2017/075293 5/2017
WO WO 2017/112957 6/2017
WO WO 2017/096158 7/2017
WO WO 2017/143155 8/2017
WO WO 2017/144338 8/2017
WO WO 2017/156336 9/2017
WO WO 2017/184984 10/2017
WO WO 2017/192633 11/2017
WO WO 2018/023068 2/2018
WO WO 2018/026873 2/2018
WO WO 2018/045181 3/2018
WO WO 2018/064640 4/2018
WO WO 2018/085599 5/2018
WO WO 2018/089550 5/2018
WO WO 2018/089910 5/2018
WO WO 2018/091676 5/2018
WO WO 2018/136397 7/2018
WO WO 2018/136856 7/2018
WO WO 2018/144582 8/2018
WO WO 2018/148471 8/2018
WO WO 2018/148700 8/2018
WO WO 2018/175779 9/2018
WO WO 2018/209398 11/2018
WO WO 2018/217862 11/2018
WO WO 2019/012005 1/2019
WO WO 2019/023214 1/2019
WO WO 2019/032760 2/2019
WO WO 2019/068880 4/2019
WO WO 2019/089836 5/2019
WO WO 2019/089851 5/2019
WO WO 2019/113457 6/2019
WO WO 2019/126313 6/2019
WO WO 2019/140201 7/2019
WO WO 2019/140334 7/2019
WO WO 2019/165318 8/2019
WO WO 2019/213254 11/2019
WO WO 2019/213294 11/2019
WO WO 2019/222523 11/2019
WO WO 2019/241290 12/2019
WO WO 2020/028194 2/2020
WO WO 2020/041148 2/2020
WO WO 2020/047002 3/2020
WO WO 2020/047004 3/2020
WO WO 2020/047010 3/2020
WO WO 2020/053655 3/2020
WO WO 2020/056381 3/2020
WO WO 2020/076979 4/2020
WO WO 2020/099640 5/2020
WO WO 2020/112604 6/2020
WO WO 2020/117914 6/2020
WO WO 2020/123301 6/2020
WO WO 2020/123305 6/2020
WO WO 2020/123309 6/2020
WO WO 2020/123311 6/2020
WO WO 2020/123316 6/2020
WO WO 2020/123317 6/2020
WO WO 2020/123318 6/2020
WO WO 2020/123319 6/2020
WO WO 2020/123320 7/2020
WO WO 2020/160044 8/2020
WO WO 2020/167862 8/2020
WO WO 2020/176788 9/2020
WO WO 2020/176882 9/2020
WO WO 2020/190509 9/2020
WO WO-2020176788 A1 * 9/2020 ........... C12Q 1/6841
WO WO 2020/198071 10/2020
WO WO 2020/206285 10/2020
WO WO 2020/240025 12/2020
WO WO 2020/243579 12/2020
WO WO 2020/254519 12/2020
WO WO 2021/016379 1/2021
WO WO 2021/041974 3/2021
WO WO 2021/067246 4/2021
WO WO 2021/067514 4/2021
WO WO 2021/091611 5/2021
WO WO 2021/092433 5/2021
WO WO 2021/097255 5/2021
WO WO 2021/102003 5/2021
WO WO 2021/102005 5/2021
WO WO 2021/102039 5/2021
WO WO 2021/116715 6/2021
WO WO 2021/119320 6/2021
WO WO 2021/133842 7/2021
WO WO 2021/133845 7/2021
WO WO 2021/133849 7/2021
WO WO 2021/142233 7/2021
WO WO 2021/168261 8/2021
WO WO 2021/168278 8/2021
WO WO 2021/207610 10/2021
WO WO 2021/216708 10/2021
WO WO 2021/225900 11/2021
WO WO 2021/236625 11/2021
WO WO 2021/236929 11/2021
WO WO 2021/237056 11/2021
WO WO 2021/237087 11/2021
WO WO 2021/242834 12/2021
WO WO 2021/247543 12/2021
WO WO 2021/247568 12/2021
WO WO 2021/247593 12/2021
WO WO 2021/252499 12/2021
WO WO 2021/252576 12/2021
WO WO 2021/252591 12/2021
WO WO 2021/252747 12/2021
WO WO 2021/263111 12/2021
WO WO 2022/025965 2/2022
WO WO 2022/032195 2/2022
WO WO 2022/060798 3/2022
WO WO 2022/060953 3/2022
WO WO 2022/061150 3/2022
WO WO 2022/061152 3/2022
WO WO 2022/087273 4/2022
WO WO 2022/099037 5/2022
WO WO 2022/103712 5/2022
WO WO 2022/109181 5/2022
WO WO 2022/132645 6/2022
WO WO 2022/140028 6/2022
WO WO 2022/147005 7/2022
WO WO 2022/147296 7/2022
WO WO 2022/164615 8/2022
WO WO 2022/178267 8/2022
WO WO 2022/198068 9/2022
WO WO 2022/212269 10/2022
WO WO 2022/221425 10/2022
WO WO 2022/226057 10/2022
WO WO 2022/236054 11/2022
WO WO 2022/243303 11/2022
WO WO 2022/226372 12/2022
WO WO 2022/256503 12/2022
WO WO 2022/271820 12/2022
WO WO 2023/287765 1/2023
WO WO 2023/018799 2/2023
WO WO 2023/034489 3/2023
WO WO 2023/034739 3/2023
WO WO 2023/043897 3/2023
WO WO 2023/044071 3/2023
WO WO 2023/076345 5/2023
WO WO 2023/086880 5/2023
WO WO 2023/102118 6/2023
WO WO 2023/122033 6/2023
WO WO 2023/130019 7/2023
WO WO 2023/147355 8/2023
WO WO 2023/150098 8/2023

(56) References Cited

FOREIGN PATENT DOCUMENTS

| | | |
|---|---|---|
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

Asp et al., "A spatiotemporal organ-wide gene expression and cell atlas of the developing human heart," Cell, Dec. 12, 2019, 179(7):1647-1660.

Kim et al., "Replication of DNA Microarrays Prepared by In Situ Oligonucleotide Polymerization and Mechanical Transfer," Anal Chem., 2007, 79:7267-7274.

Kuhn et al., "A novel, high-performance random array platform for quantitative gene expression profiling," Genome Res, 2004, 14:2347-2356.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

U.S. Appl. No. 16/876,709, filed May 18, 2020, Schnall-Levin et al.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrNOCH17rEkOUXwd19It/e54d99fb08a8f1500aba503 005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec 28, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal G.T Mismatches in DNA," Biochemistry, 1996, 36(34):10581-10594.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Andresen et al., "Helicase-dependent amplification: use in OnChip amplification and potential for point-of-care diagnostics," Expert Rev Mol Diagn., Oct. 2009, 9(7):645-650.

Appella, "Non-natural nucleic acids for synthetic biology," Current Opinion in Chemical Biology, Dec 2009, 13(5-6): 687-696.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al., "2D-PCR: a method of mapping DNA in tissue sections," Lab Chip, 2009, 9(24):3526-34.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Asp et al., "Spatially Resolved Transcriptomes-Next Generation Tools for Tissue Exploration," Bioessays, Oct. 2020, 42(10):e1900221, 16 pages.

Assets.ctassets.net [online], "Technical Note—Visium Spatial Gene Expression Imaging Guidelines," CG000241 Rev A, 2019, retrieved on Jul. 29, 2022, retrieved from URL <https://assets.ctfassets.net/an68im79xiti/76JHgFQo6aLq8UPvfLOu2c/fc39e46f86bf75676d3f7da6dc721fad/CG000241_VisiumImagingGuidelinesTN_Rev_A.pdf>, 8 pages.

(56) References Cited

OTHER PUBLICATIONS

Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Bell, "A simple way to treat PCR products prior to sequencing using ExoSAP-IT," Biotechniques, 2008, 44(6):834, 1 page.
Belton et al., "Hi-C: A comprehensive technique to capture the conformation of genomes," Methods, Nov. 2012, 58(3):268-276, 16 pages.
Bentley et al., "Accurate whole human genome sequencing using reversible terminator chemistry," Nature, 2008, 456(7218):53-59.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Borm et al., "Scalable in situ single-cell profiling by electrophoretic capture of mRNA," bioRxiv, Jan. 2022, 32 pages.
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec 2013, 10(12): 1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Caliari et al., "A practical guide to hydrogels for cell culture," Nat Methods., Apr. 2016, 13(5):405-14.
Cardona et al., "TrakEM2 0.9a User Manual," Sep. 8, 2011, retrieved on Jul. 29, 2022, retrieved from URL <https://www.ini.uzh.ch/~acardona/trakem2_manual.html>, 38 pages.
Carter et al., "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.

(56) References Cited

OTHER PUBLICATIONS

Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc, 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Ertsey et al., "Coverslip Mounted-Immersion Cycled in Situ RT-PCR for the Localization of mRNA in Tissue Sections," Biotechniques, 1998, 24(1):92-100.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Falconnet et al., "Rapid, Sensitive and Real-Time Multiplexing Platform for the Analysis of Protein and Nucleic-Acid Biomarkers," Anal. Chem., Jan. 7, 2015, 87:1582-1589.
Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Protein detection using proximity-dependent DNA ligation assays," Nature Biotech., 20: 473-77, 2002.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Gamper et al., "Gene expression profile of bladder tissue of patients with ulcerative interstitial cystitis," BMC Genomics, Apr. 28, 2009, 10(199):1-17.
Ganguli et al., "Pixelated spatial gene expression analysis from tissue," Nat Commun., Jan. 2018, 9(1):202, 9 pages.

(56) References Cited

OTHER PUBLICATIONS

Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Github.com [online], "ST Spot Detector Usage Guide: A Guide to Using the Spatial Transcriptomics Spot Detector 2.0," Jun. 2018, retrieved on Jul. 29, 2022, retrieved from URL <https://github.com/SpatialTranscriptomicsResearch/st_spot_detector/wiki/ST-Spot-Detector-Usage-Guide, 6 pages.
Glass et al., "SIMPLE: a sequential immunoperoxidase labeling and erasing method," J. Histochem. Cytochem., Oct. 2009, 57(10):899-905.
Gloor, "Gene targeting in *Drosophila,*" Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadrup et al., "Parallel detection of antigen-specific T-cell responses by multidimensional encoding of MHC multimers," Nat. Methods., Jul. 2009, 6(7), 520-526.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hobro et al., "An evaluation of fixation methods: Spatial and compositional cellular changes observed by Raman imaging," Vibrational Spectroscopy, Jul. 2017, 91:31-45.
Hoffman et al., "Formaldehyde crosslinking: a tool for the study of chromatin complexes," J Biol Chem., Oct. 2015, 290(44):26404-11.
Howell et al., "iFRET: An Improved Fluorescence System for DNA-Melting Analysis," Genome Research, 2002, 12:1401-1407.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hua et al., "Multi-level transcriptome sequencing identifies COL1A1 as a candidate marker in human heart failure progression," BMC Med., Jan. 2020, 18(1):2, 16 pages.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from

(56) References Cited

OTHER PUBLICATIONS

URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Kap et al., "Histological assessment of PAXgene tissue fixation and stabilization reagents," PLoS One, 2011, 6:e27704, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells," Apr. 2019, 10(1):1930, 10 pages.

Ke et al., "In situ sequencing for RNA analysis in preserved tissue and cells," Nat Methods., Sep. 2013, Supplementary Materials, 29 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of Mycobacterium avium: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Korbel et al., "Paired-end mapping reveals extensive structural variation in the human genome," Science, 2007, 318(5849):420-426.

Kozlov et al., "A highly scalable peptide-based assay system for proteomics," PLoS ONE, 2012, 7(6):e37441, 10 pages.

Kozlov et al., "A method for rapid protease substrate evaluation and optimization," Comb Chem High Throughput Screen, 2006, 9(6):481-87.

Kristensen et al., "High-Throughput Methods for Detection of Genetic Variation," BioTechniques, Feb. 2001, 30(2):318-332.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.

Kumar et al., "Template-directed oligonucleotide strand ligation, covalent intramolecular DNA circularization and catenation using click chemistry," J Am Chem Soc, May 2007, 129(21):6859-64.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmocogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lahiani et al., "Enabling Histopathological Annotations on Immunofluorescent Images through Virtualization of Hematoxylin and Eosin," J Pathol Inform., Feb. 2018, 9:1, 8 pages.

Lampe et al., "A purified mariner transposase is sufficient to mediate transposition in vitro," EMBO J., Oct. 1996, 15(19):5470-9.

Lamture et al., "Direct detection of nucleic acid hybridization on the surface of a charge coupled device," Nucleic Acid Res., Jun. 1994, 22(11):2121-5.

Landegren et al., "A Ligase-Mediated Gene Detection Technique," Science, 1988, 241(4869):1077-1080.

Landegren et al., "Reading bits of genetic information: methods for single-nucleotide polymorphism analysis," Genome Res., Aug. 1998, 8(8):769-76.

Langdale et al., "A rapid method of gene detection using DNA bound to Sephacryl," Gene, 1985, 36(3):201-210.

Larman et al., "Sensitive, multiplex and direct quantification of RNA sequences using a modified RASL assay," Nucleic Acids Research, 2014, 42(14):9146-9157.

Lee et al., "Fluorescent in situ sequencing (FISSEQ) of RNA for gene expression profiling in intact cells and tissues," Nature Protocols, 2015, 10(3):442-458.

Lee et al., "Improving the efficiency of genomic loci capture using oligonucleotide arrays for high throughput resequencing," BMC Genomics, Dec. 2009, 10:646, 12 pages.

Leriche et al., "Cleavable linkers in chemical biology," Bioorganic & Medicinal Chemistry, 2012, 20:571-582.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lin et al., "Highly multiplexed imaging of single cells using a high-throughput cyclic immunofluorescence method," Nat Commun., Sep. 2015, 6:8390, 7 pages.

Linnarsson, "Recent advances in DNA sequencing methods—general principles of sample preparation," Experimental Cell Research, 2010, 316(8):1339-1343.

Liu et al., "High-Spatial-Resolution Multi-Omics Atlas Sequencing of Mouse Embryos via Deterministic Barcoding in Tissue," BioRxiv, 2019, 55 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Lizardi et al., "Mutation detection and single-molecule counting using isothermal rolling-circle amplification," Nat. Genet., 1998, 19(3):225-232.

Lou et al., "A review of room temperature storage of biospecimen tissue and nucleic acids for anatomic pathology laboratories and biorepositories," Clin Biochem., Mar. 2014, 47(4-5):267-73.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

(56) References Cited

OTHER PUBLICATIONS

Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Mamedov et al., "Preparing unbiased T-cell receptor and antibody cDNA libraries for the deep next generation sequencing profiling," Frontiers in Immunol., Dec. 23, 2013, 4(456):1-10.
Maniatis et al., "Spatiotemporal Dynamics of Molecular Pathology in Amyotrophic Lateral Sclerosis," bioRxiv, Science, 2018, 364(6435), 54 pages.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mccloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec 1, 2001, 29(23):e118, 9 pages.
Nam et al., "Nanoparticle-Based Bio-Bar Codes for the Ultrasensitive Detection of Proteins," Science, Sep. 26, 2003, 301(5641):1884-1886.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 Rna Ligase 2," Journal of Biological Chemistry, Jul. 2004, 279(30):31337-31347.
Navarro et al., "ST viewer: a tool for analysis and visualization of spatial transcriptomics datasets: Supplementary Information," Bioinformatics, Mar. 2019, 1058-1060.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to ligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak, "Entering the Postgenome Era," Science, 1995, 270(5235):368-71.
Ohtsubo et al., "Bacterial insertion sequences," Curr Top Microbiol Immunol., 1996, 204:1-26.
Oksuz et al., "Systematic evaluation of chromosome conformation capture assays," Nature Methods, Sep. 2021, 18:1046-1055.
Olivier, "The Invader assay for SNP genotyping," Mutat. Res., Jun. 2005, 573(1-2):103-110.

(56) References Cited

OTHER PUBLICATIONS

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gene," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc, Jan. 2014, 9(1):171-81.
Picelli et al., "Tn5 transposase and tagmentation procedures for massively scaled sequencing projects," Genome Res., Dec. 2014, 24(12):2033-40.
Piepenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Redmond et al., "Single-cell TCRseq: paired recovery of entire T-cell alpha and beta chain transcripts in T-cell receptors from single-cell RNAseq," Genome Med, 2016, 8:80, 12 pages.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rohland et al., "Partial uracil-DNA-glycosylase treatment for screening of ancient DNA," Phil. Trans. R. Soc. B, Jan. 19, 2015, 370(1660): Jun. 24, 2013, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schmidl et al., "ChIPmentation: fast, robust, low-input ChIP-seq for histones and transcription factors," Nature Methods, Oct. 2015, 12:963-965.
Schouten et al., "Relative quantification of 40 nucleic acid sequences by multiplex ligation-dependent probe amplification," Nucleic Acids Res., Jun. 2002, 30(12): e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.

(56) References Cited

OTHER PUBLICATIONS

Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Su et al., "Restriction enzyme selection dictates detection range sensitivity in chromatin conformation capture-based variant-to-gene mapping approaches," bioRxiv, Dec 15, 2020, 22 pages.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein- protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilbrey-Clark et al., "Cell Atlas technologies and insights into tissue architecture," Biochemical Journal, Apr. 2020, 477(8):1427-1442.
Wilson et al., "New transposon delivery plasmids for insertional mutagenesis in Bacillus anthracis," J Microbiol Methods, Dec 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc, 2008, 130(37):12456-64.
Wong et al., "ST Spot Detector: a web-based application for automatic spot and tissue detection for Spatial Transcriptomics image datasets," Bioinformatics, Jan. 2018, 34(11):1966-1968.
Worthington et al., "Cloning of random oligonucleotides to create single-insert plasmid libraries," Anal Biochem, 2001, 294(2):169-175.

(56) References Cited

OTHER PUBLICATIONS

Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Baysoy et al., "The technological landscape and applications of single-cell multi-omics," Nature Reviews Molecular Cell Biology, Jun. 6, 2023, 24(10):695-713.
Kishi et al., "Light-Seq: light-directed in situ barcoding of biomolecules in fixed cells and tissues for spatially indexed sequencing," Nature Methods, Oct. 10, 2022, 19(11):1393-1402.
Konry et al., "Microsphere-Based Rolling Circle Amplification Microarray for the Detection of DN A and Proteins in a Single Assay," Anal. Chem., 2009 81(14):5777-5782.
10x Genomics, "Assay Scheme and Configuration of Chromium™ Single Cell V(D)J Libraries," 10x Genomics, CG000109 Rev D, 2017, 10 pages.
Deng et al., "Spatial-ATAC-seq: spatially resolved chromatin accessibility profiling of tissues at genome scale and cellular level," bioRxiv, Jun. 7, 2021, retrieved from URL <https://www.biorxiv.org/content/10.1101/2021.06.06.447244v1>, 49 pages (Preprint).
Hong et al., "Cell Microarray Technologies for High-Throughput Cell-Based Biosensors," Sensors (Basel), Jun. 5, 2017, 17(6):1293.
Stickels et al., "Highly sensitive spatial transcriptomics at near-cellular resolution with Slide-seqV2," Nat Biotechnol., Mar. 2021, 39(3):313-319, 28 pages (Author Manuscript).

* cited by examiner

Ethylene Carbonate (2%) and Glycerol (2.5%)
250mM NaCl

Ethylene Carbonate (2%) and Glycerol (2.5%)
500mM NaCl

METHODS, COMPOSITIONS, AND SYSTEMS FOR ENHANCING SPATIAL ANALYSIS OF ANALYTES IN A BIOLOGICAL SAMPLE

CROSS REFERENCE TO RELATED APPLICATIONS

This application claims the benefit of U.S. Provisional Application No. 63/436,003, filed on Dec. 29, 2022, which is incorporated in its entirety into this application.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling and cross-talk with other cells in the tissue.

Spatial heterogeneity has been previously studied using techniques that only provide data for a small handful of analytes in the context of an intact tissue or a portion of a tissue, or provides substantial analyte data for dissociated tissue (i.e., single cells), but fail to provide information regarding the position of the single cell in a parent biological sample (e.g., tissue sample).

Spatial analysis of a nucleic acid analyte within a biological sample may require determining the sequence of the analyte or a complement thereof and the sequence of spatial barcode or a complement thereof that is associated with the location of the analyte within the biological sample. The biological sample may be placed on a solid support to improve specificity and efficiency when being analyzed for identification or characterization of an analyte, such as DNA or RNA, within the biological sample. Depending on the type and/or state of the biological sample, different approaches may be required to permit spatial analysis of an analyte with specificity and high sensitivity. Thus, there is a need for improved methods to allow for specific and sensitive spatial analysis of analytes in both a targeted and global manner.

SUMMARY

The present disclosure features methods, compositions, devices, and systems for determining the location and/or abundance of an analyte in a biological sample. Determining the spatial location and/or abundance of analytes (e.g., proteins, DNA, or RNA) within a biological sample leads to better understanding of spatial heterogeneity in various contexts, such as disease models. Described herein are methods for capturing probes and/or barcodes associated with an analyte to a capture domain of a capture probe. In some instances, the techniques disclosed herein facilitate downstream processing, such as sequencing of the probes and/or barcodes bound to a capture domain. The methods disclosed herein are predicated on the finding that variations in concentrations of certain reagents and improve spatial protein detection of biological samples without affecting RNA detection. For instances, it has been identified herein that including sodium chloride (NaCl) at certain concentrations (e.g., 500 mM) during incubation of oligo-tagged antibodies can improve protein detection on a spatial array. Also described herein are methods for processing nucleic acids and/or other analytes in a biological sample while retaining spatial context. These methods can, for example, allow for the determination of the location and/or abundance of the target analyte in the biological sample.

Thus, included herein is a method for analyzing an analyte in a biological sample mounted on a first substrate, the method comprising: (a) contacting the biological sample with a plurality of analyte capture agents, wherein an analyte capture agent of the plurality of analyte capture agents comprises an analyte binding moiety and a capture agent barcode domain, wherein the contacting results in the analyte binding moiety specifically binding to the analyte, and wherein the capture agent barcode domain comprises an analyte binding moiety barcode and a capture handle sequence; (b) aligning the first substrate with a second substrate comprising an array, such that at least a portion of the biological sample is aligned with at least a portion of the array, wherein the array comprises a plurality of capture probes, wherein a first capture probe of the plurality of capture probes comprises: (i) a first spatial barcode and (ii) a first capture domain; (c) when the biological sample is aligned with at least a portion of the array, contacting the biological sample and/or the array with a reagent medium comprising a monovalent salt or divalent salt, and releasing the capture agent barcode domain from the analyte capture agent; and (d) hybridizing the capture handle sequence of the capture agent barcode domain to the capture domain.

In some instances, the monovalent salt or divalent salt in the reagent medium is at a concentration of about 100-750 mM. In some instances, the monovalent salt or divalent salt in the reagent medium is at a concentration of about 250 mM or about 500 mM. In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the monovalent salt is potassium chloride. In some instances, the divalent salt is magnesium chloride. In some instances, the reagent medium further comprises ethylene carbonate. In some instances, the ethylene carbonate in the reagent medium comprises about 2% of the reagent medium. In some instances, the reagent medium further comprises glycerol. In some instances, the glycerol in the reagent medium comprises about 2.5% of the reagent medium. In some instances, the plurality of analyte capture agents is in an amount of about 0.1 μg to about 1.5 μg. In some instances, the plurality of analyte capture agents is in an amount of about 0.6 μg to about 1.0 μg. In some instances, the reagent medium further comprises a permeabilization agent, wherein the contacting in step (c) permeabilizes the biological sample.

In some instances, the permeabilization agent comprises a protease. In some instances, the protease is selected from trypsin, pepsin, elastase, or proteinase K.

In some instances, the aligning comprises: (i) mounting the first substrate on a first member of a support device, the first member configured to retain the first substrate; (ii) mounting the second substrate on a second member of the support device; (iii) applying the reagent medium to the first substrate and/or the second substrate; and (iv) operating an alignment mechanism of the support device to move the first member and/or the second member such that at least a portion of the biological sample is aligned with at least a portion of the array, and such that the portion of the biological sample and the portion of the array contact the reagent medium.

In some instances, the alignment mechanism is coupled to the first member, the second member, or both the first member and the second member. In some instances, the alignment mechanism comprises a linear actuator, optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

In some instances, during the hybridization step, a separation distance is maintained between the first substrate and the second substrate, optionally wherein the separation distance is less than 50 microns, optionally wherein the separation distance is between 2-25 microns, optionally wherein the separation distance is measured in a direction orthogonal to the surface of the first substrate to which the biological sample is mounted, and/or at least the portion of the biological sample is vertically aligned with the at least portion of the array.

In some instances, at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample.

In some instances, the chamber comprises a partially or fully sealed chamber, and/or the second substrate comprises the spacer, and/or the first substrate comprises the spacer, and/or the applying the reagent medium to the first substrate and/or the second substrate comprises applying the reagent medium to a region of the spacer, the region outside an enclosed area of the second substrate, or the enclosed area formed by the spacer.

In some instances, as the first substrate and/or the second substrate are moved via the alignment mechanism, the first substrate is at an angle relative to the second substrate such that a dropped slide of the first substrate and a portion of the second substrate contact the reagent medium, optionally wherein: the dropped side of the first substrate urges the reagent medium toward the opposite direction, and/or the alignment mechanism further moves the first substrate and/or the second substrate to maintain an approximately parallel arrangement of the first substrate and the second substrate and a separation distance between the first substrate and the second substrate, optionally when the approximately parallel arrangement and the separation distance are maintained, the spacer fully encloses and surrounds the at least portion of the biological sample and the at least portion of the array, and the spacer forms the sides of the chamber which hold a volume of the reagent medium.

In some instances, the reagent medium further comprises a detergent. In some instances, the reagent medium comprises less than 5 w/v % of one or more detergents. In some instances, the detergent is selected from sodium dodecyl sulfate (SDS), sarkosyl, saponin, a nonionic surfactant, polysorbate 20, or a combination thereof. In some instances, the reagent medium comprises less than 5 w/v % of SDS and/or sarkosyl. In some instances, the reagent medium comprises at least 5% w/v % of SDS and/or sarkosyl. In some instances, the reagent medium does not comprise SDS or sarkosyl. In some instances, the reagent medium further comprises polyethylene glycol (PEG).

In some instances, the first capture probe comprises a poly(T) sequence, preferably wherein the first capture domain of the first capture probe comprises the poly(T) sequence. In some instances, the first capture domain of the first capture probe comprises a sequence substantially complementary to the capture handle sequence. In some instances, the first capture probe further comprises one or more functional domains, a unique molecular identifier (UMI), a cleavage domain, or a combination thereof.

In some instances, the methods also include generating a single nucleic acid molecule that comprises (i) all or a part of the capture agent barcode domain, or a complement thereof; and (ii) the first spatial barcode, or a complement thereof. In some instances, the methods also include determining (i) all or a part of the capture agent barcode domain, or a complement thereof; and (ii) the first spatial barcode, or a complement thereof (e.g., from the single nucleic acid molecule). In some instances, the methods further include using the determined sequences of (i) and (ii) to determine the location and/or abundance of the analyte in the biological sample. In some instances, the determining comprises sequencing (i) all or a part of the sequence of the capture agent barcode domain, or a complement thereof, and (ii) the first spatial barcode, or a complement thereof.

In some instances, the analyte binding moiety is an antibody or an antigen binding fragment thereof. In some instances, the analyte capture agent comprises a linker. In some instances, the linker is a cleavable linker. In some instances, the cleavable linker is a photo-cleavable linker, a UV-cleavable linker, or an enzyme cleavable linker. In some instances, the cleavable linker is a disulfide linker.

In some instances, the analyte is a protein. In some instances, the analyte is an intracellular protein. In some instances, the analyte is an extracellular protein.

In some instances, the methods also include analyzing a different analyte in the biological sample. In some instances, the analyzing the different analyte comprises: (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) coupling the first probe and the second probe, thereby generating a connected probe; (c) when the biological sample is aligned with at least a portion of the array, (i) releasing the connected probe from the different analyte and (ii) migrating the connected probe from the biological sample to the array; and (d) hybridizing the connected probe to a second capture domain of a second capture probe comprised in the plurality of capture probes, wherein the second capture probe comprises: (i) a second spatial barcode and (ii) the second capture domain.

In some instances, the first probe and the second probe are on a contiguous nucleic acid sequence. In some instances, the first probe is on the 3' end of the contiguous nucleic acid sequence. In some instances, the second probe is on the 5' end of the contiguous nucleic acid sequence. In some instances, the adjacent sequences abut one another. In some instances, the adjacent sequences are at least 1, 2, 3, 4, 5, 6, 7, 8, 9, 10, or more nucleotides away from one another. In some instances, the methods include generating an extended first probe using a polymerase, wherein the extended first probe comprises a sequence complementary to a sequence between the sequence hybridized to the first probe and the sequence hybridized to the second probe.

In some instances, the methods also include generating an extended second probe using a polymerase, wherein the extended second probe comprises a sequence complementary to a sequence between the sequence hybridized to the first probe and the sequence hybridized to the second probe.

In some instances, the methods include hybridizing a third probe to the first probe and the second probe. In some instances, the third probe comprises: (i) a sequence that is at least 80%, at least 85%, at least 90%, at least 95%, at least 96%, at least 97%, at least 98%, or at least 99%, or 100% complementary to a portion of the first probe that hybridizes to the third probe; and (ii) a sequence that is at least 80%, at least 85%, at least 90%, at least 95%, at least 96%, at least 97%, at least 98%, or at least 99%, or 100% complementary to a portion of the second probe that hybridizes to the third probe.

In some instances, the coupling the first probe and the second probe comprises ligating via a ligase the first probe and the second probe. In some instances, the coupling the first probe and the second probe comprises ligating via a ligase: (i) the first probe and the extended second probe; or (ii) the extended first probe and the second probe. In some instances, the ligase is selected from a *Chlorella* virus DNA ligase, a single stranded DNA ligase, or a T4 DNA ligase.

In some instances, the methods include amplifying the connected probe prior to the step of releasing the connected probe from the different analyte. In some instances, the amplifying comprises rolling circle amplification.

In some instances, the reagent medium further comprises a nuclease. In some instances, the nuclease comprises an RNase, optionally wherein the RNase is selected from RNase A, RNase C, RNase H, or RNase I.

In some instances, the methods further include determining (i) all or a part of the sequence of the connected probe, or a complement thereof, and (ii) the second spatial barcode, or a complement thereof, optionally wherein the method further comprises using the determined sequence of (i) and (ii) to determine the location and/or abundance of the different analyte in the biological sample. In some instances, the determining comprises sequencing (i) all or a part of the sequence of the connected probe, or a complement thereof, and (ii) the second spatial barcode, or a complement thereof. In some instances, at least 50% of the connected probe released from the portion of the biological sample aligned with the portion of the array are captured by capture probes of the portion of the array. In some instances, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the connected probe are detected in spots directly under the biological sample.

In some instances, the different analyte is RNA. In some instances, the RNA is mRNA.

In some instances, the biological sample is a tissue sample. In some instances, the tissue sample is a solid tissue sample. In some instances, the solid tissue sample is a tissue section. In some instances, the biological sample is a fixed tissue sample. In some instances, the fixed tissue sample is a formalin fixed paraffin embedded (FFPE) tissue sample. In some instances, the FFPE tissue sample is deparaffinized and decrosslinked prior to step (a). In some instances, the fixed tissue sample is a formalin fixed paraffin embedded cell pellet. In some instances, the tissue sample is a fresh frozen tissue sample. In some instances, the biological sample is stained and/or destained. In some instances, the biological sample is stained using hematoxylin and/or eosin, immunohistochemistry, and/or immunofluorescence. In some instances, the tissue sample is a tissue microarray.

In some instances, the connected probe is extended using the second capture probe as template, thereby generating an extended connected probe. In some instances, the methods include releasing the extended connected probe from the capture probe and/or from the array. In some instances, the determining and/or sequencing steps include using the extended connected probe. In some instances, the capture agent barcode domain is extended using the second capture probe as template, thereby generating an extended capture agent barcode domain. In some instances, the methods include releasing the extended capture agent barcode domain from the capture probe and/or from the array. In some instances, the determining and/or sequencing steps include using the extended capture agent barcode domain. In some instances, the first spatial barcode and the second spatial barcode are the same. In some instances, the first spatial barcode and the second spatial barcode are different. In some instances, the first capture domain and the second capture domain are the same. In some instances, the first capture domain and the second capture domain are different. In some instances, the methods also include imaging the biological sample.

Also disclosed herein is a method for analyzing an analyte in a biological sample mounted on a first substrate, the method comprising: (a) contacting the biological sample with a plurality of analyte capture agents, wherein an analyte capture agent of the plurality of analyte capture agents comprises an analyte binding moiety and a capture agent barcode domain, wherein the contacting results in the analyte binding moiety specifically binding to the analyte, and wherein the capture agent barcode domain comprises an analyte binding moiety barcode and a capture handle sequence; (b) contacting the biological sample with an array, wherein the array comprises a plurality of capture probes, wherein a first capture probe of the plurality of capture probes comprises: (i) a first spatial barcode and (ii) a first capture domain; (c) contacting the biological sample and/or the array with a reagent medium comprising a monovalent salt or divalent salt, and releasing the capture agent barcode domain from the analyte capture agent; and (d) hybridizing the capture handle sequence of the capture agent barcode domain to the capture domain.

In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the reagent medium further comprises ethylene carbonate. In some instances, the ethylene carbonate in the reagent medium comprises about 2% of the reagent medium. In some instances, the reagent medium further comprises glycerol. In some instances, the glycerol in the reagent medium comprises about 2.5% of the reagent medium. In some instances, the plurality of analyte capture agents is in an amount of about 0.1 μg to about 1.5 μg. In some instances, the plurality of analyte capture agents is in an amount of about 0.6 μg to about 1.0 μg. In some instances, the methods also include determining (i) all or a part of the capture agent barcode domain, or a complement thereof; and (ii) the first spatial barcode, or a complement thereof. In some instances, the methods further include using the determined sequence of (i) and (ii) to determine the location and/or abundance of the analyte in the biological sample. In some instances, the determining comprises sequencing (i) all or a part of the sequence of the capture agent barcode domain, or a complement thereof, and (ii) the first spatial barcode, or a complement thereof.

In some instances, the methods on a single substrate also include analyzing a different analyte in the biological sample. In some instances, the analyzing the different analyte comprises: (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) coupling the first probe and the second probe, thereby generating a connected probe; (c) when the biological sample is aligned with at least a portion of the array, (i) releasing the connected probe from the different analyte and (ii) migrating the connected probe from the biological sample to the array; and (d) hybridizing the connected probe to a second capture domain of a second capture probe comprised in the plurality of capture probes, wherein the second capture probe comprises: (i) a second spatial barcode and (ii) the second capture domain.

In some instances, the methods also include determining (i) all or a part of the sequence of the connected probe, or a complement thereof, and (ii) the second spatial barcode, or a complement thereof, optionally wherein the method further comprises using the determined sequence of (i) and (ii) to determine the location and/or abundance of the different analyte in the biological sample. In some instances, the determining comprises sequencing (i) all or a part of the sequence of the connected probe, or a complement thereof, and (ii) the second spatial barcode, or a complement thereof.

Also disclosed herein is a system or kit for analyzing an analyte in a biological sample, the system or the kit comprising: (a) a support device configured to retain a first substrate and a second substrate, wherein the biological sample is placed on the first substrate, and wherein the second substrate comprises a plurality of capture probes, wherein a capture probe of the plurality of capture probes comprises: (i) a spatial barcode and (ii) a capture domain; (b) a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and a capture handle sequence; (c) a reagent medium comprising a monovalent salt or divalent salt; and (d) instructions for performing the method of any one of the methods disclosed herein.

In some instances, the system or kit also includes a first probe and a second probe, wherein the first probe and the second probe each comprise a sequence that is substantially complementary to adjacent sequences of the analyte, wherein the second probe comprises a capture probe binding domain, and wherein the first probe and the second probe are capable of being ligated together to form a connected probe. In some instances, the reagent medium further comprises a permeabilization agent. In some instances, the permeabilization agent is pepsin or proteinase K. In some instances, the reagent medium further comprises an agent for releasing the connected probe from the analyte when hybridized thereto. In some instances, the agent for releasing the connected probe is an RNAse, optionally wherein the RNAse is selected from RNase A, RNase C, RNase H, or RNase I.

In some instances, the system or kit also includes an alignment mechanism on the support device to align the first substrate and the second substrate. In some instances, the alignment mechanism comprises a linear actuator, wherein the first substrate comprises a first member and the second substrate comprises a second member, and optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/see, and/or the linear actuator is configured to move the first member, the second member, or both the first member and the second member with an amount of force of at least 0.1 lbs.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

A. Spatial Analysis Methods

Figure 1A:
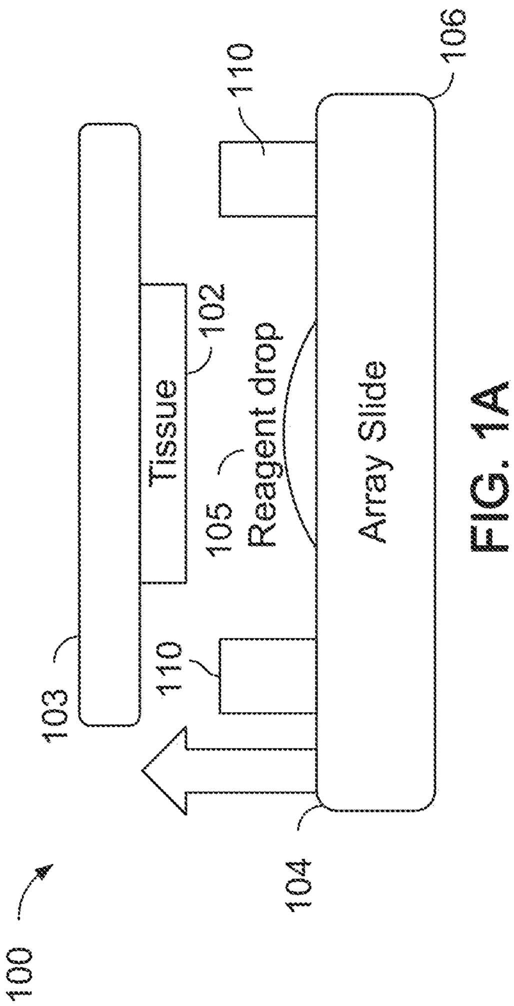
FIG. 1A shows an exemplary sandwiching process where a first substrate (e.g., a slide), including a biological sample, and a second substrate (e.g., array slide) are brought into proximity with one another.

Spatial analysis methodologies described herein can provide a vast amount of analyte and/or expression data for a variety of analytes within a biological sample at high spatial resolution, while retaining native spatial context. Spatial analysis methods can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 11,447,807, 11,352,667, 11,168,350, 11,104,936, 11,008,608, 10,995,361, 10,913,975, 10,774,374, 10,724,078, 10,640,816, 10,494,662, 10,480,022, 10,364,457, 10,317,321, 10,059,990, 10,041,949, 10,030,261, 10,002,316, 9,879,313, 9,783,841, 9,727,810, 9,593,365, 8,951,726, 8,604,182, and 7,709,198; U.S. Patent Application Publication Nos. 2020/0239946, 2020/0080136, 2020/0277663, 2019/0330617, 2020/0256867, 2020/0224244, 2019/0085383, and 2013/0171621; PCT Publication Nos. WO2018/091676, WO2020/176788, WO2017/144338, and WO2016/057552; Non-patent literature references Rodriques et al., Science 363(6434): 1463-1467, 2019; Lee et al., Nat. Protoc. 10(3): 442-458, 2015; Trejo et al., PLOS ONE 14(2):e0212031, 2019; Chen et al., Science 348(6233): aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev F, dated January 2022); and/or the Visium Spatial Gene Expression Reagent Kits—Tissue Optimization User Guide (e.g., Rev E, dated February 2022), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of PCT Publication No. WO2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of PCT Publication No. WO2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, the biological sample is a tissue sample. In some embodiments, the biological sample (e.g., tissue sample) is a tissue microarray (TMA). A tissue microarray contains multiple representative tissue samples—which can be from different tissues or organisms—assembled on a single histologic slide. The TMA can therefore allow for high throughput analysis of multiple specimens at the same time. Tissue microarrays are paraffin blocks produced by extracting cylindrical tissue cores from different paraffin donor blocks and re-embedding these into a single recipient (microarray) block at defined array coordinates.

The biological sample as used herein can be any suitable biological sample described herein or known in the art. In some embodiments, the biological sample is a tissue sample. In some embodiments, the tissue sample is a solid tissue sample. In some embodiments, the biological sample is a tissue section (e.g., a fixed tissue section). In some embodiments, the tissue is flash-frozen and sectioned. Any suitable method described herein or known in the art can be used to flash-freeze and section the tissue sample. In some embodiments, the biological sample, e.g., the tissue, is flash-frozen using liquid nitrogen before sectioning. In some embodiments, the biological sample, e.g., a tissue sample, is flash-frozen using nitrogen (e.g., liquid nitrogen), isopentane, or hexane.

In some embodiments, the biological sample, e.g., the tissue, is embedded in a matrix e.g., optimal cutting temperature (OCT) compound to facilitate sectioning. OCT compound is a formulation of clear, water-soluble glycols and resins, providing a solid matrix to encapsulate biological (e.g., tissue) specimens. In some embodiments, the sectioning is performed by cryosectioning, for example using a microtome. In some embodiments, the methods further comprise a thawing step, after the cryosectioning.

The biological sample can be from a mammal. In some instances, the biological sample is from a human, mouse, or rat. In addition to the subjects described above, the biological sample can be obtained from non-mammalian organisms (e.g., a plants, an insect, an arachnid, a nematode (e.g., *Caenorhabditis elegans*), a fungi, an amphibian, or a fish (e.g., zebrafish)). A biological sample can be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from a eukaryote, such as a patient derived organoid (PDO) or patient derived xenograft (PDX). The biological sample can include organoids, a miniaturized and simplified version of an organ produced in vitro in three dimensions that shows realistic micro-anatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

In some embodiments, the biological sample, e.g., the tissue sample, is fixed in a fixative including alcohol, for example methanol. In some embodiments, instead of methanol, acetone, or an acetone-methanol mixture can be used. In some embodiments, the fixation is performed after sectioning In some instances, when the biological sample is fixed with a fixative including an alcohol (e.g., methanol or acetone-methanol mixture), it is not decrosslinked afterward. In some preferred embodiments, the biological sample is fixed with a fixative including an alcohol (e.g., methanol or an acetone-methanol mixture) after freezing and/or sectioning. In some instances, the biological sample is flash-frozen, and then the biological sample is sectioned and fixed (e.g., using methanol, acetone, or an acetone-methanol mixture). In some instances when methanol, acetone, or an acetone-methanol mixture is used to fix the biological sample, the sample is not decrosslinked at a later step. In instances when the biological sample is frozen (e.g., flash frozen using liquid nitrogen and embedded in OCT) followed by sectioning and alcohol (e.g., methanol, acetone-methanol) fixation or acetone fixation, the biological sample is referred to as "fresh frozen". In some embodiments, fixation of the biological sample e.g., using acetone and/or alcohol (e.g., methanol, acetone-methanol) is performed while the sample is mounted on a substrate (e.g., glass slide, such as a positively charged glass slide).

In some embodiments, the biological sample, e.g., the tissue sample, is fixed e.g., immediately after being harvested from a subject. In such embodiments, the fixative is preferably an aldehyde fixative, such as paraformaldehyde (PFA) or formalin. In some embodiments, the fixative induces crosslinks within the biological sample. In some embodiments, after fixing e.g., by formalin or PFA, the biological sample is dehydrated via sucrose gradient. In some instances, the fixed biological sample is treated with a sucrose gradient and then embedded in a matrix e.g., OCT compound. In some instances, the fixed biological sample is not treated with a sucrose gradient, but rather is embedded in a matrix e.g., OCT compound after fixation. In some embodiments when a fixed frozen tissue sample is treated with a sucrose gradient, it can be rehydrated with an ethanol gradient. In some embodiments, the PFA or formalin fixed biological sample, which can be optionally dehydrated via sucrose gradient and/or embedded in OCT compound, is then frozen e.g., for storage or shipment. In such instances, the biological sample is referred to as “fixed frozen”. In preferred embodiments, a fixed frozen biological sample is not treated with methanol. In preferred embodiments, a fixed frozen biological sample is not paraffin embedded. Thus, in preferred embodiments, a fixed frozen biological sample is not deparaffinized. In some embodiments, a fixed frozen biological sample is rehydrated in an ethanol gradient.

In some instances, the biological sample (e.g., a fixed frozen tissue sample) is treated with a citrate buffer. Citrate buffer can be used for antigen retrieval to decrosslink antigens and fixation medium in the biological sample. Thus, any suitable decrosslinking agent can be used in addition to or alternatively to citrate buffer. In some embodiments, for example, the biological sample (e.g., a fixed frozen tissue sample) is decrosslinked with TE buffer.

In any of the foregoing, the biological sample can further be stained, imaged, and/or destained. For example, in some embodiments, a fresh frozen tissue sample or fixed frozen tissue sample is stained (e.g., via cosin and/or hematoxylin), imaged, destained (e.g., via HCl), or a combination thereof. In some embodiments, when a fresh frozen tissue sample is fixed in methanol, it is treated with isopropanol prior to being stained (e.g., via cosin and/or hematoxylin), imaged, destained (e.g., via HCl), or a combination thereof. In some embodiments when a fixed frozen tissue sample is treated with a sucrose gradient, it can be rehydrated with an ethanol gradient before being stained, (e.g., via cosin and/or hematoxylin), imaged, destained (e.g., via HCl), decrosslinked (e.g., via TE buffer or citrate buffer), or a combination thereof. In some embodiments, the biological sample can undergo further fixation (e.g., while mounted on a substrate), stained, imaged, and/or destained. For example, a fixed frozen biological sample may be subject to an additional fixing step (e.g., using PFA) before optional ethanol rehydration, staining, imaging, and/or destaining.

In any of the foregoing, the biological sample can be fixed using PAXgene. For example, the biological sample can be fixed using PAXgene in addition, or alternatively to, a fixative disclosed herein or known in the art (e.g., alcohol, acetone, acetone-alcohol, formalin, paraformaldehyde). PAXgene is a non-cross-linking mixture of different alcohols, acid and a soluble organic compound that preserves morphology and bio-molecules. It is a two-reagent fixative system in which tissue is firstly fixed in a solution containing methanol and acetic acid then stabilized in a solution containing ethanol. See, Ergin B. et al., J Proteome Res. 2010 Oct. 1; 9(10):5188-96; Kap M. et al., PLOS One.; 6(11): e27704 (2011); and Mathieson W. et al., Am J Clin Pathol.; 146(1):25-40 (2016), each of which are hereby incorporated by reference in their entirety, for a description and evaluation of PAXgene for tissue fixation. Thus, in some embodiments, when the biological sample, e.g., the tissue sample, is fixed in a fixative including alcohol, the fixative is PAXgene. In some embodiments, a fresh frozen tissue sample is fixed with PAXgene. In some embodiments, a fixed frozen tissue sample is fixed with PAXgene.

In some embodiments, the biological sample, e.g., the tissue sample is fixed, for example in methanol, acetone, acetone-methanol, PFA, PAXgene or is formalin-fixed and paraffin-embedded (FFPE). In some embodiments, the biological sample comprises intact cells. In some embodiments, the biological sample is a cell pellet, e.g., a fixed cell pellet, e.g., an FFPE cell pellet. FFPE samples are used in some instances in the RTL methods disclosed herein. A limitation of direct RNA capture for fixed samples is that the RNA integrity of fixed (e.g., FFPE) samples can be lower than a fresh sample, thereby making it more difficult to capture RNA directly, e.g., by capture of a common sequence such as a poly(A) tail of an mRNA molecule. However, by utilizing RTL probes that hybridize to RNA target sequences in the transcriptome, one can avoid a requirement for RNA analytes to have both a poly(A) tail and target sequences intact. Accordingly, RTL probes can be utilized to beneficially improve capture and spatial analysis of fixed samples. The biological sample, e.g., tissue sample, can be stained, and imaged prior, during, and/or after each step of the methods described herein. Any of the methods described herein or known in the art can be used to stain and/or image the biological sample. In some embodiments, the imaging occurs prior to destaining the sample. In some embodiments, the biological sample is stained using an H&E staining method. In some embodiments, the tissue sample is stained and imaged for about 10 minutes to about 2 hours (or any of the subranges of this range described herein). Additional time may be needed for staining and imaging of different types of biological samples.

The tissue sample can be obtained from any suitable location in a tissue or organ of a subject, e.g., a human subject. In some instances, the sample is a mouse sample. In some instances, the sample is a human sample. In some embodiments, the sample can be derived from skin, brain, breast, lung, liver, kidney, prostate, tonsil, thymus, testes, bone, lymph node, ovary, eye, heart, or spleen. In some instances, the sample is a human or mouse breast tissue sample. In some instances, the sample is a human or mouse brain tissue sample. In some instances, the sample is a human or mouse lung tissue sample. In some instances, the sample is a human or mouse tonsil tissue sample. In some instances, the sample is a human or mouse liver tissue sample. In some instances, the sample is a human or mouse bone, skin, kidney, thymus, testes, or prostate tissue sample. In some embodiments, the tissue sample is derived from normal or diseased tissue. In some embodiments, the sample is an embryo sample. The embryo sample can be a non-human embryo sample. In some instances, the sample is a mouse embryo sample.

Biological samples are also described in Section (I)(d) of PCT Publication No. WO2020/176788 and/or U.S. Patent Application Publication No. 2020/0277663.

The following embodiments can be used with any of the methods described herein. In some embodiments, the biological sample (e.g., a fixed and/or stained biological sample) is imaged. In some embodiments, the biological sample is visualized or imaged using bright field microscopy. In some embodiments, the biological sample is visualized or imaged using fluorescence microscopy. Additional methods of visualization and imaging are known in the art. Non-limiting examples of visualization and imaging include expansion microscopy, bright field microscopy, dark field microscopy, phase contrast microscopy, electron microscopy, fluorescence microscopy, reflection microscopy, interference microscopy and confocal microscopy. In some embodiments, the sample is stained and imaged prior to adding reagents for analyzing captured analytes as disclosed herein to the biological sample.

In some embodiments, the methods include staining the biological sample. In some embodiments, the staining includes the use of hematoxylin and/or eosin. Non-limiting examples of stains include histological stains (e.g., hematoxylin and/or cosin) and immunological stains (e.g., fluorescent stains). In some embodiments, a biological sample can be stained using any number of biological stains, including but not limited to, acridine orange, Bismarck brown, carmine, coomassie blue, cresyl violet, DAPI, cosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the biological sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the staining includes the use of a detectable label selected from the group consisting of a radioisotope, a fluorophore, a chemiluminescent compound, a bioluminescent compound, or a combination thereof.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of PCT Publication No. WO2020/176788 and/or U.S. Patent Application Publication No. 2020/0277663. Briefly, in any of the methods described herein, the method includes a step of permeabilizing the biological sample. For example, the biological sample can be permeabilized to facilitate transfer of the extension products to the capture probes on the array. In some embodiments, the permeabilizing includes the use of an organic solvent (e.g., acetone, ethanol, and methanol), a detergent (e.g., saponin, Triton X-100™, Tween-20™, or sodium dodecyl sulfate (SDS)), an enzyme (an endopeptidase, an exopeptidase, a protease), or combinations thereof. In some embodiments, the permeabilizing includes the use of an endopeptidase, a protease, SDS, polyethylene glycol tert-octylphenyl ether, polysorbate 80, and polysorbate 20, N-lauroylsarcosine sodium salt solution, saponin, Triton X-100™, Tween-20™, or combinations thereof. In some embodiments, the endopeptidase is pepsin. In some embodiments, the endopeptidase is Proteinase K. Additional methods for sample permeabilization are described, for example, in Jamur et al., *Method Mol. Biol.* 588:63-66, 2010, the entire contents of which are incorporated herein by reference.

Array-based spatial analysis methods can involve the transfer of one or more analytes or derivatives thereof from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI) and a capture domain). In some instances, the capture probe includes a homopolymer sequence, such as a poly(T) sequence. In some embodiments, a capture probe can include a cleavage domain and/or a functional domain (e.g., a primer-binding site, such as for next-generation sequencing (NGS)). See, e.g., Section (II) (b) (e.g., subsections (i)-(vi)) of PCT Publication No. WO2020/176788 and/or U.S. Patent Application Publication No. 2020/0277663. Generation of capture probes can be achieved by any appropriate method, including those described in Section (II)(d)(ii) of PCT Publication No. WO2020/176788 and/or U.S. Patent Application Publication No. 2020/0277663.

In some instances, a capture probe and a nucleic acid analyte (or any other nucleic acid to nucleic acid interaction) occurs because the sequences of the two nucleic acids are substantially complementary to one another. By "substantial," "substantially" and the like, two nucleic acid sequences can be complementary when at least 60% of the nucleotide residues of one nucleic acid sequence are complementary to nucleotide residues in the other nucleic acid sequence. The complementary residues within a particular complementary nucleic acid sequence need not always be contiguous with each other, and can be interrupted by one or more non-complementary residues within the complementary nucleic acid sequence. In some embodiments, at least 60%, but less than 100%, of the residues of one of the two complementary nucleic acid sequences are complementary to residues in the other nucleic acid sequence. In some embodiments, at least 70%, 80%, 90%, 95% or 99% of the residues of one nucleic acid sequence are complementary to residues in the other nucleic acid sequence. Sequences are said to be "substantially complementary" when at least 60% (e.g., at least 70%, at least 80%, or at least 90%) of the residues of one nucleic acid sequence are complementary to residues in the other nucleic acid sequence. In some embodiments, the biological sample is mounted on a first substrate and the substrate comprising the array of capture probes is a second substrate. During this process, one or more analytes or analyte derivatives (e.g., intermediate agents; e.g., ligation products) are released from the biological sample and migrate to the second substrate comprising an array of capture probes. In some embodiments, the release and migration of the analytes or analyte derivatives to the second substrate comprising the array of capture probes occurs in a manner that preserves the original spatial context of the analytes in the biological sample. This method can be referred to as a sandwiching process, which is described e.g., in U.S. Patent Application Pub. No. 2021/0189475 and PCT Pub. Nos. WO 2021/252747 A1, WO 2022/061152 A2, and WO 2022/140028 A1.

FIG. 1A shows an exemplary sandwiching process 100 where a first substrate (e.g., slide 103), including a biological sample 102, and a second substrate (e.g., array slide 104 including an array having spatially barcoded capture probes 106) are brought into proximity with one another. As shown in FIG. 1A a liquid reagent drop (e.g., permeabilization solution 105) is introduced on the second substrate in proximity to the capture probes 106 and in between the biological sample 102 and the second substrate (e.g., slide

104 including an array having spatially barcoded capture probes 106). The permeabilization solution 105 may release analytes or analyte derivatives (e.g., intermediate agents; e.g., ligation products) that can be captured by the capture probes of the array 106.

During the exemplary sandwiching process, the first substrate is aligned with the second substrate, such that at least a portion of the biological sample is aligned with at least a portion of the capture probes (e.g., aligned in a sandwich configuration). As shown, the second substrate (e.g., array slide 104) is in an inferior position to the first substrate (e.g., slide 103). In some embodiments, the first substrate (e.g., slide 103) may be positioned superior to the second substrate (e.g., slide 104). A reagent medium 105 within a gap between the first substrate (e.g., slide 103) and the second substrate (e.g., slide 104) creates a liquid interface between the two substrates. The reagent medium may be a permeabilization solution which permeabilizes and/or digests the biological sample 102. In some embodiments wherein the biological sample 102 has been pre-permeabilized, the reagent medium is not a permeabilization solution. Herein, the reagent medium may also comprise one or more of a monovalent salt, a divalent salt, ethylene carbonate, and/or glycerol. In some embodiments, analytes (e.g., mRNA transcripts) and/or analyte derivatives (e.g., intermediate agents; e.g., ligation products) of the biological sample 102 may release from the biological sample, and actively or passively migrate (e.g., diffuse) across the gap toward the capture probes on the array 106. Alternatively, in certain embodiments, migration of the analyte or analyte derivative (e.g., intermediate agent; e.g., ligation product) from the biological sample is performed actively (e.g., electrophoretic, by applying an electric field to promote migration). Exemplary methods of electrophoretic migration are described in WO 2020/176788, and US. Patent Application Pub. No. 2021/0189475, each of which is hereby incorporated by reference.

As further shown, one or more spacers 110 may be positioned between the first substrate (e.g., slide 103) and the second substrate (e.g., array slide 104 including spatially barcoded capture probes 106). The one or more spacers 110 may be configured to maintain a separation distance between the first substrate and the second substrate. While the one or more spacers 110 is shown as disposed on the second substrate, the spacer may additionally or alternatively be disposed on the first substrate.

In some embodiments, the one or more spacers 110 is configured to maintain a separation distance between first and second substrates that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, or between about 2 microns and 10 microns), measured in a direction orthogonal to the surface of first substrate that supports the biological sample. In some instances, the separation distance is about 2, 3, 4, 5, 6, 7, 8, 9, 10, 11, 12, 13, 14, 15, 16, 17, 18, 19, 20, 21, 22, 23, 24, or 25 microns. In some embodiments, the separation distance is less than 50 microns. In some embodiments, the separation distance is less than 25 microns. In some embodiments, the separation distance is less than 20 microns. The separation distance may include a distance of at least 2 μm.

Figure 1B:
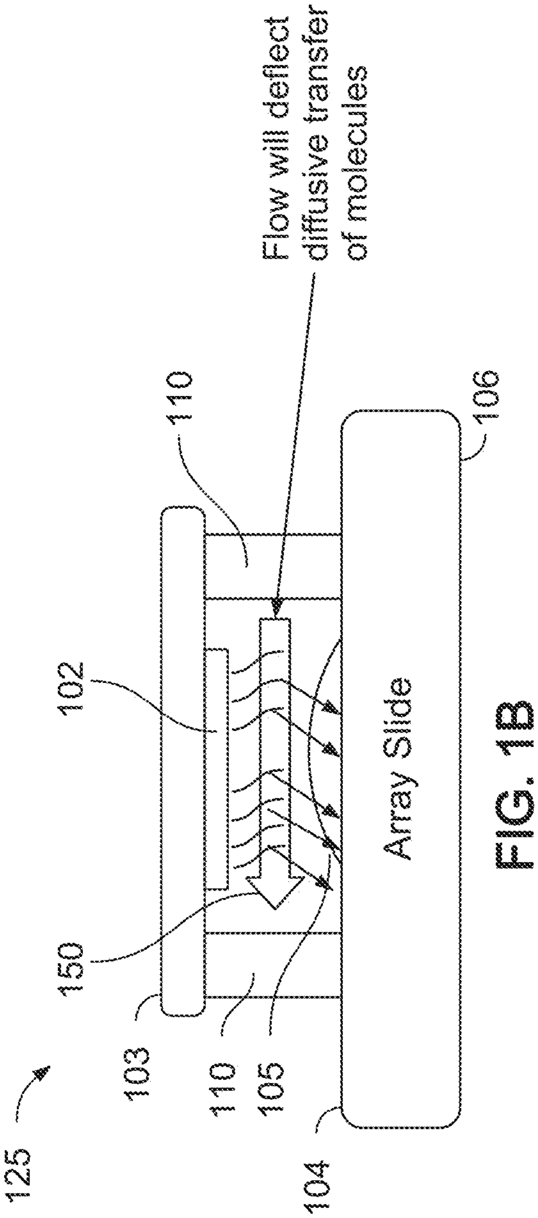
FIG. 1B shows a fully formed sandwich configuration creating a chamber formed from the one or more spacers, the first substrate, and the second substrate.

FIG. 1B shows a fully formed sandwich configuration 125 creating a chamber 150 formed from the one or more spacers 110, the first substrate (e.g., the slide 103), and the second substrate (e.g., the slide 104 including an array 106 having spatially barcoded capture probes) in accordance with some example implementations. In the example of FIG. 1B, the liquid reagent (e.g., the permeabilization solution 105) fills the volume of the chamber 150 and may create a permeabilization buffer that allows analytes (e.g., mRNA transcripts and/or other molecules) or analyte derivatives (e.g., intermediate agents; e.g., ligation products) to diffuse from the biological sample 102 toward the capture probes of the second substrate (e.g., slide 104). In some aspects, flow of the permeabilization buffer may deflect transcripts and/or molecules from the biological sample 102 and may affect diffusive transfer of analytes or analyte derivatives (e.g., intermediate agents; e.g., ligation products) for spatial analysis. A partially or fully sealed chamber 150 resulting from the one or more spacers 110, the first substrate, and the second substrate may reduce or prevent flow from undesirable convective movement of transcripts and/or molecules over the diffusive transfer from the biological sample 102 to the capture probes.

The sandwiching process methods described above can be implemented using a variety of hardware components. For example, the sandwiching process methods can be implemented using a sample holder (also referred to herein as a support device, a sample handling apparatus, and an array alignment device). Further details on support devices, sample holders, sample handling apparatuses, or systems for implementing a sandwiching process are described in, e.g., US. Patent Application Pub. No. 2021/0189475, and PCT Publ. No. WO 2022/061152 A2, each of which are incorporated by reference in their entirety.

In some embodiments of a sample holder, the sample holder can include a first member including a first retaining mechanism configured to retain a first substrate comprising a biological sample. The first retaining mechanism can be configured to retain the first substrate disposed in a first plane. The sample holder can further include a second member including a second retaining mechanism configured to retain a second substrate disposed in a second plane. The sample holder can further include an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The adjustment mechanism may be configured to move the second member along the axis orthogonal to the second plane and/or move the first member along an axis orthogonal to the first plane.

In some embodiments, the adjustment mechanism includes a linear actuator. In some embodiments, the linear actuator is configured to move the second member along an axis orthogonal to the plane of the first member and/or the second member. In some embodiments, the linear actuator is configured to move the first member along an axis orthogonal to the plane of the first member and/or the second member. In some embodiments, the linear actuator is configured to move the first member, the second member, or both the first member and the second member at a velocity of at least 0.1 mm/sec. In some embodiments, the linear actuator is configured to move the first member, the second member, or both the first member and the second member with an amount of force of at least 0.1 lbs.

Figure 2A:
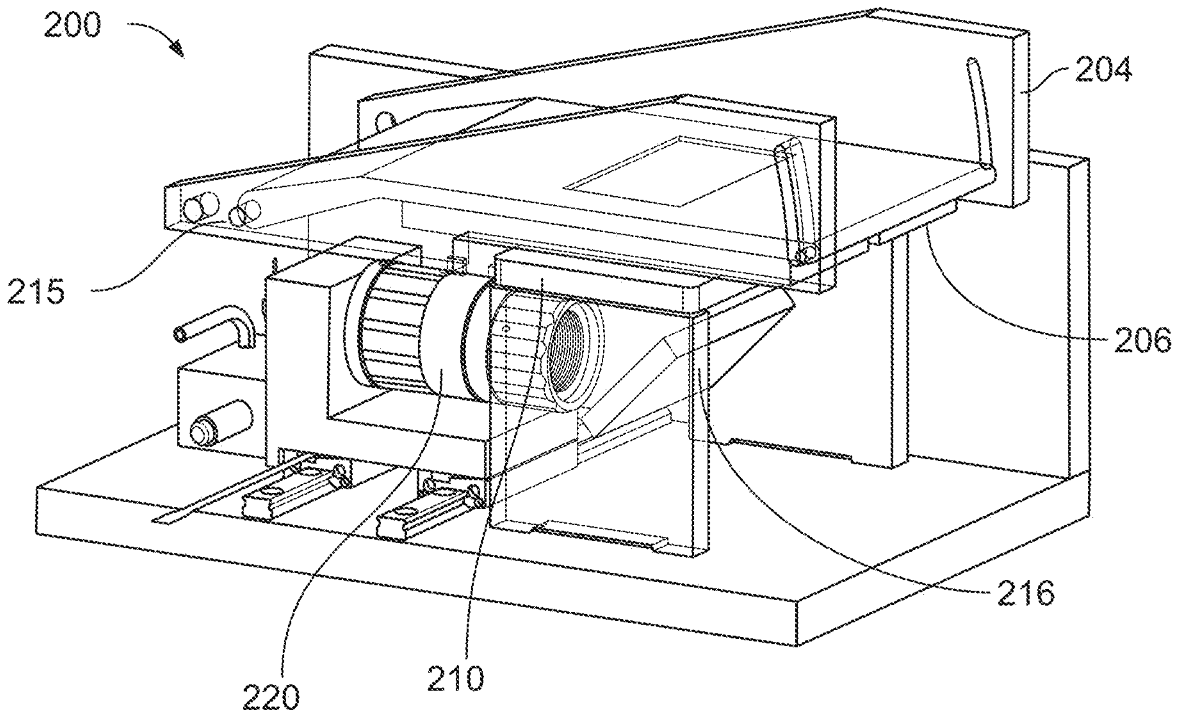
FIG. 2A shows a perspective view of an exemplary sample handling apparatus in a closed position.

FIG. 2A is a perspective view of an example sample handling apparatus 200 in a closed position in accordance with some example implementations. As shown, the sample handling apparatus 200 includes a first member 204, a second member 210, optionally an image capture device 220, a first substrate 206, optionally a hinge 215, and optionally a mirror 216. The hinge 215 may be configured to allow the first member 204 to be positioned in an open or closed configuration by opening and/or closing the first member 204 in a clamshell manner along the hinge 215.

Figure 2B:
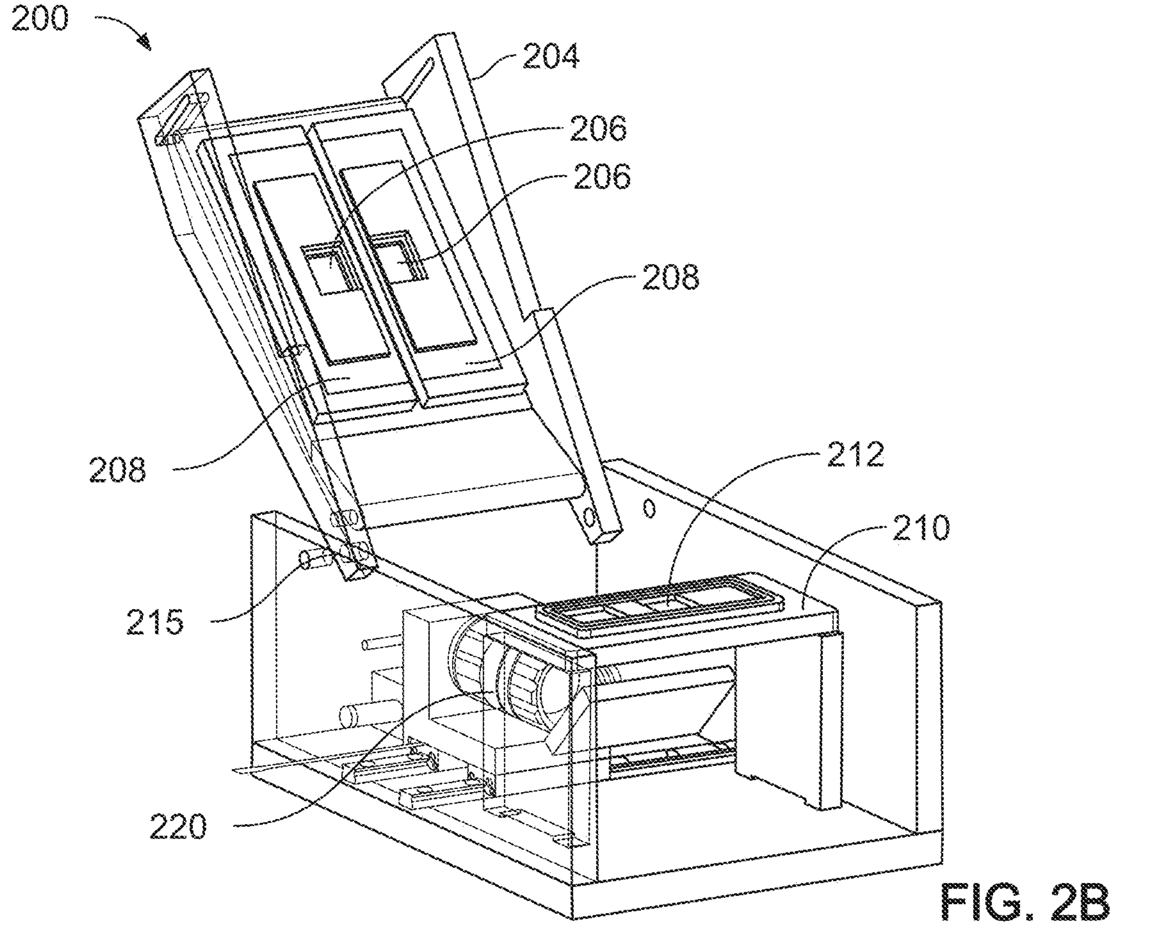
FIG. 2B shows a perspective view of an exemplary sample handling apparatus in an open position.

FIG. 2B is a perspective view of the example sample handling apparatus 200 in an open position in accordance with some example implementations. As shown, the sample handling apparatus 200 includes one or more first retaining mechanisms 208 configured to retain one or more first substrates 206. In the example of FIG. 2B, the first member 204 is configured to retain two first substrates 206, however the first member 204 may be configured to retain more or fewer first substrates 206.

In some aspects, when the sample handling apparatus 200 is in an open position (e.g., in FIG. 2B), the first substrate 206 and/or the second substrate 212 may be loaded and positioned within the sample handling apparatus 200 such as within the first member 204 and the second member 210, respectively. As noted, the hinge 215 may allow the first member 204 to close over the second member 210 and form a sandwich configuration.

In some aspects, after the first member 204 closes over the second member 210, an adjustment mechanism of the sample handling apparatus 200 may actuate the first member 204 and/or the second member 210 to form the sandwich configuration for the permeabilization step (e.g., bringing the first substrate 206 and the second substrate 212 closer to each other and within a threshold distance for the sandwich configuration). The adjustment mechanism may be configured to control a speed, an angle, a force, or the like of the sandwich configuration.

In some embodiments, the biological sample (e.g., sample 102 from FIG. 1A) may be aligned within the first member 204 (e.g., via the first retaining mechanism 208) prior to closing the first member 204 such that a desired region of interest of the sample is aligned with the barcoded array of the second substrate (e.g., the slide 104 from FIG. 1A), e.g., when the first and second substrates are aligned in the sandwich configuration. Such alignment may be accomplished manually (e.g., by a user) or automatically (e.g., via an automated alignment mechanism). After or before alignment, spacers may be applied to the first substrate 206 and/or the second substrate 212 to maintain a minimum spacing between the first substrate 206 and the second substrate 212 during sandwiching. In some aspects, the permeabilization solution (e.g., permeabilization solution 305) may be applied to the first substrate 206 and/or the second substrate 212. The first member 204 may then close over the second member 210 and form the sandwich configuration. Analytes or analyte derivatives (e.g., intermediate agents; e.g., ligation products) may be captured by the capture probes of the array and may be processed for spatial analysis.

In some embodiments, during the permeabilization step, the image capture device 220 may capture images of the overlap area between the biological sample and the capture probes on the array 106. If more than one first substrates 206 and/or second substrates 212 are present within the sample handling apparatus 200, the image capture device 220 may be configured to capture one or more images of one or more overlap areas.

Figures 3A, 3B, 3C:
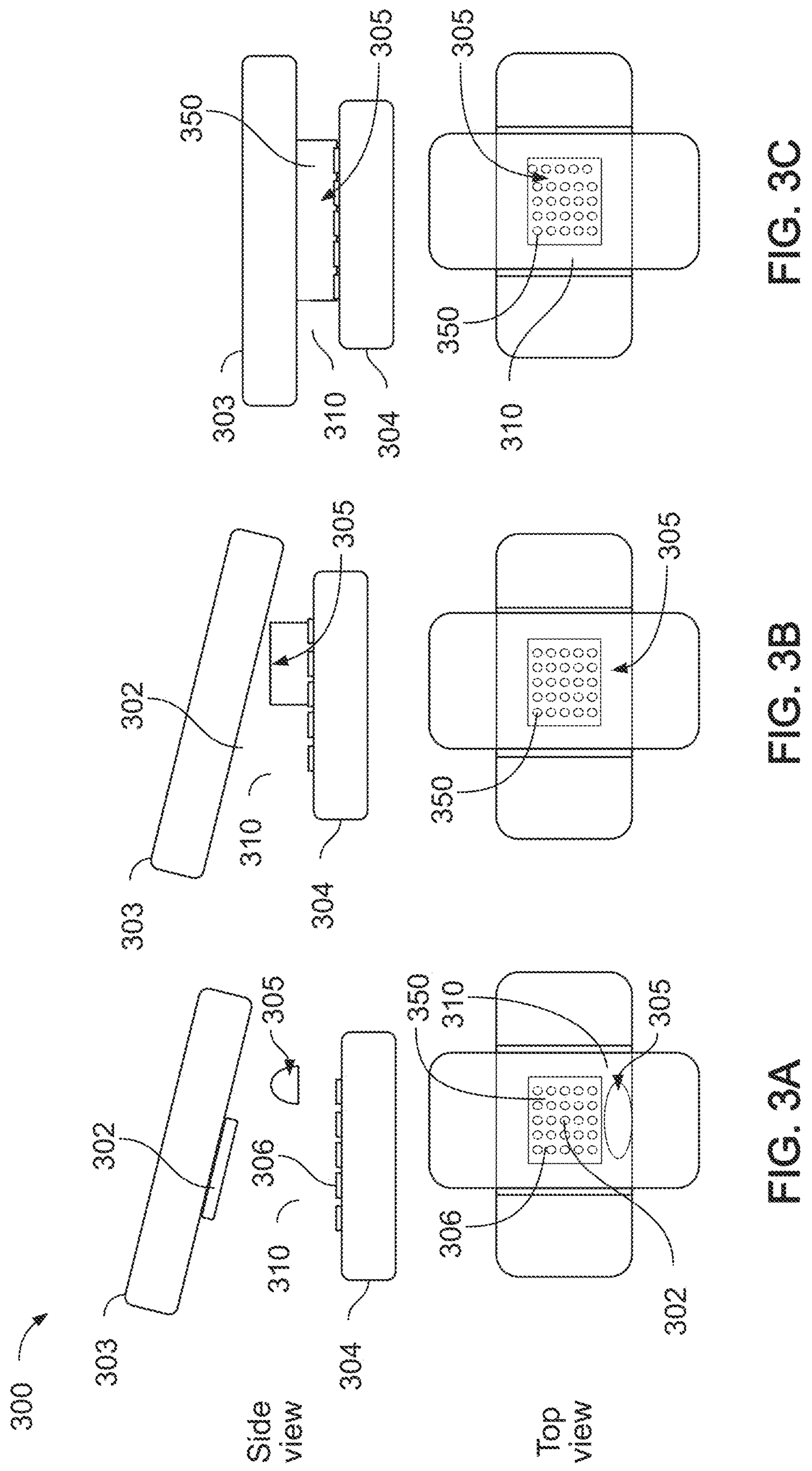
FIG. 3A shows the first substrate angled over (superior to) the second substrate.
FIG. 3B shows that as the first substrate lowers, and/or as the second substrate rises, the dropped side of the first substrate may contact a drop of reagent medium.
FIG. 3C shows a full closure of the sandwich between the first substrate and the second substrate with one or more spacers contacting both the first substrate and the second substrate.

Provided herein are methods for delivering a fluid to a biological sample disposed on an area of a first substrate and an array disposed on a second substrate. FIGS. 3A-3C depict a side view and a top view of an exemplary angled closure workflow 300 for sandwiching a first substrate (e.g., slide 303) having a biological sample 302 and a second substrate (e.g., slide 304 having capture probes 306) in accordance with some exemplary implementations.

FIG. 3A depicts the first substrate (e.g., the slide 303 including a biological sample 302) angled over (superior to) the second substrate (e.g., slide 304). As shown, reagent medium (e.g., permeabilization solution) 305 is located on the spacer 310 toward the right-hand side of the side view in FIG. 3A. While FIG. 3A depicts the reagent medium on the right hand side of side view, it should be understood that such depiction is not meant to be limiting as to the location of the reagent medium on the spacer.

FIG. 3B shows that as the first substrate lowers, and/or as the second substrate rises, the dropped side of the first substrate (e.g., a side of the slide 303 angled toward the second substrate) may contact the reagent medium 305. The dropped side of the first substrate may urge the reagent medium 305 toward the opposite direction (e.g., towards an opposite side of the spacer 310, towards an opposite side of the first substrate relative to the dropped side). For example, in the side view of FIG. 3B the reagent medium 305 may be urged from right to left as the sandwich is formed.

In some embodiments, the first substrate and/or the second substrate are further moved to achieve an approximately parallel arrangement of the first substrate and the second substrate.

FIG. 3C depicts a full closure of the sandwich between the first substrate and the second substrate with the spacer 310 contacting both the first substrate and the second substrate and maintaining a separation distance and optionally the approximately parallel arrangement between the two substrates. As shown in the top view of FIG. 3C, the spacer 310 fully encloses and surrounds the biological sample 302 and the capture probes 306, and the spacer 310 form the sides of chamber 350 which holds a volume of the reagent medium 305.

While FIG. 3C depicts the first substrate (e.g., the slide 303 including biological sample 302) angled over (superior to) the second substrate (e.g., slide 304) and the second substrate comprising the spacer 310, it should be understood that an exemplary angled closure workflow can include the second substrate angled over (superior to) the first substrate and the first substrate comprising the spacer 310.

It may be desirable that the reagent medium be free from air bubbles between the substrates to facilitate transfer of target analytes with spatial information. Additionally, air bubbles present between the substrates may obscure at least a portion of an image capture of a desired region of interest. Accordingly, it may be desirable to ensure or encourage suppression and/or elimination of air bubbles between the two substrates (e.g., slide 303 and slide 304) during a permeabilization step (e.g., step 104). In some aspects, it may be possible to reduce or eliminate bubble formation between the substrates using a variety of filling methods and/or closing methods. In some instances, the first substrate and the second substrate are arranged in an angled sandwich assembly as described herein. For example, during the sandwiching of the two substrates (e.g., the slide 303 and the slide 304), an angled closure workflow may be used to suppress or eliminate bubble formation.

Figures 4A, 4B:
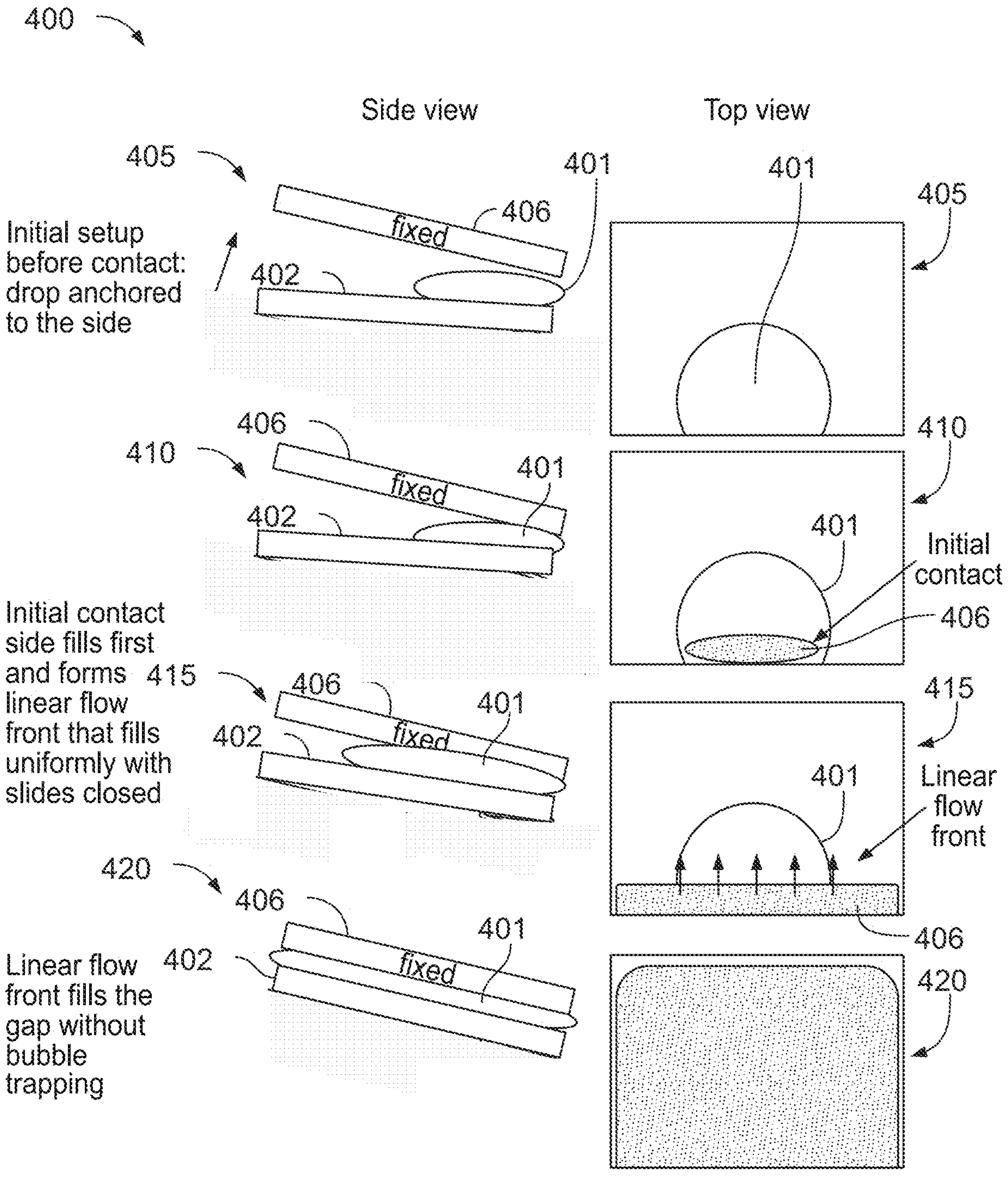
FIG. 4A shows a side view of the angled closure workflow.
FIG. 4B shows a top view of the angled closure workflow.

FIG. 4A is a side view of the angled closure workflow 400 in accordance with some exemplary implementations. FIG. 4B is a top view of the angled closure workflow 400 in accordance with some exemplary implementations. As shown at 405, reagent medium 401 is positioned to the side of the substrate 402 contacting the spring.

At step 410, the dropped side of the angled substrate 406 contacts the reagent medium 401 first. The contact of the substrate 406 with the reagent medium 401 may form a linear or low curvature flow front that fills uniformly with the slides closed.

At step 415, the substrate 406 is further lowered toward the substrate 402 (or the substrate 402 is raised up toward the substrate 406) and the dropped side of the substrate 406 may contact and may urge the reagent medium toward the side opposite the dropped side and creating a linear or low curvature flow front that may prevent or reduce bubble trapping between the substrates.

At step 420, the reagent medium 401 fills the gap between the substrate 406 and the substrate 402. The linear flow front of the liquid reagent may form by squeezing the 401 volume along the contact side of the substrate 402 and/or the substrate 406. Additionally, capillary flow may also contribute to filling the gap area.

In some embodiments, the reagent medium (e.g., 105 in FIG. 1A) comprises a permeabilization agent. In some embodiments, following initial contact between the biological sample and a permeabilization agent, the permeabilization agent can be removed from contact with the biological sample (e.g., by opening the sample holder). Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution).

In some embodiments, the reagent medium comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. In some embodiments, the reagent medium comprises a protease. Exemplary proteases include, e.g., pepsin, trypsin, elastase, and proteinase K. In some embodiments, the reagent medium comprises a nuclease. In some embodiments, the nuclease comprises an RNase. In some embodiments, the RNase is selected from RNase A, RNase C, RNase H, and RNase I. In some embodiments, the reagent medium comprises one or more of sodium dodecyl sulfate (SDS) or a sodium salt thereof, proteinase K, pepsin, N-lauroylsarcosine, and RNase.

In some embodiments, the reagent medium comprises polyethylene glycol (PEG). In some embodiments, the PEG is from about 2K to about 16K. In some embodiments, the PEG is 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v).

In certain embodiments a dried permeabilization reagent is applied or formed as a layer on the first substrate or the second substrate or both prior to contacting the biological sample with the array. For example, a permeabilization reagent can be deposited in solution on the first substrate or the second substrate or both and then dried.

In some instances, the aligned portions of the biological sample and the array are in contact with the reagent medium for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium for about 1-60 minutes.

In some instances, the device is configured to control a temperature of the first and second substrates. In some embodiments, the temperature of the first and second members is lowered to a first temperature that is below room temperature.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of PCT Publication No. WO2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligation products that serve as proxies for the template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended by a reverse transcriptase. In some embodiments, the capture probe is extended using one or more DNA polymerases. In some embodiments, the extended capture probes include the sequence of the capture domain, the sequence of the spatial barcode of the capture probe, and the complementary sequence of the template used for extension of the capture probe.

In some embodiments, extended capture probes are amplified (e.g., in bulk solution or on the array) to yield quantities that are sufficient for downstream analysis, e.g., sequencing. In some embodiments, extended capture probes (e.g., DNA molecules) can act as templates for an amplification reaction (e.g., a polymerase chain reaction).

Additional variants of spatial analysis methods, including in some embodiments, an imaging step, are described in Section (II)(a) of PCT Publication No. WO2020/176788 and/or U.S. Patent Application Publication No. 2020/0277663. Analysis of captured analytes (and/or intermediate agents or portions thereof), for example, including sample removal, extension of capture probes using the capture analyte as a template, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of PCT Publication No. WO2020/176788 and/or U.S. Patent Application Publication No. 2020/0277663.

Some quality control measures are described in Section (II)(h) of PCT Publication No. WO2020/176788 and/or U.S. Patent Application Publication No. 2020/0277663.

Spatial information can provide information of medical importance. For example, the methods described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication Nos. 2021/0140982, 2021/0198741, and 2021/0199660.

Spatial information can provide information of biological importance. For example, the methods described herein can allow for: identification of transcriptome and/or proteome expression profiles (e.g., in healthy and/or diseased tissue); identification of multiple analyte types in close proximity (e.g., nearest neighbor or proximity based analysis); determination of up- and/or down-regulated genes and/or proteins in diseased tissue; characterization of tumor microenvironments; characterization of tumor immune responses; characterization of cells types and their co-localization in healthy and diseased tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of PCT Publication No. WO2020/176788 and/or U.S. Patent Application Publication No. 2020/0277663. Exemplary features and geometric attributes of an array can be found in Sections (II)(d)(i), (II)(d)(iii), and (II)(d)(iv) of PCT Publication No. WO2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(c) of PCT Publication No. WO2020/176788 and/or U.S. Patent Application Publication No. 2020/0277663.

Figure 5:
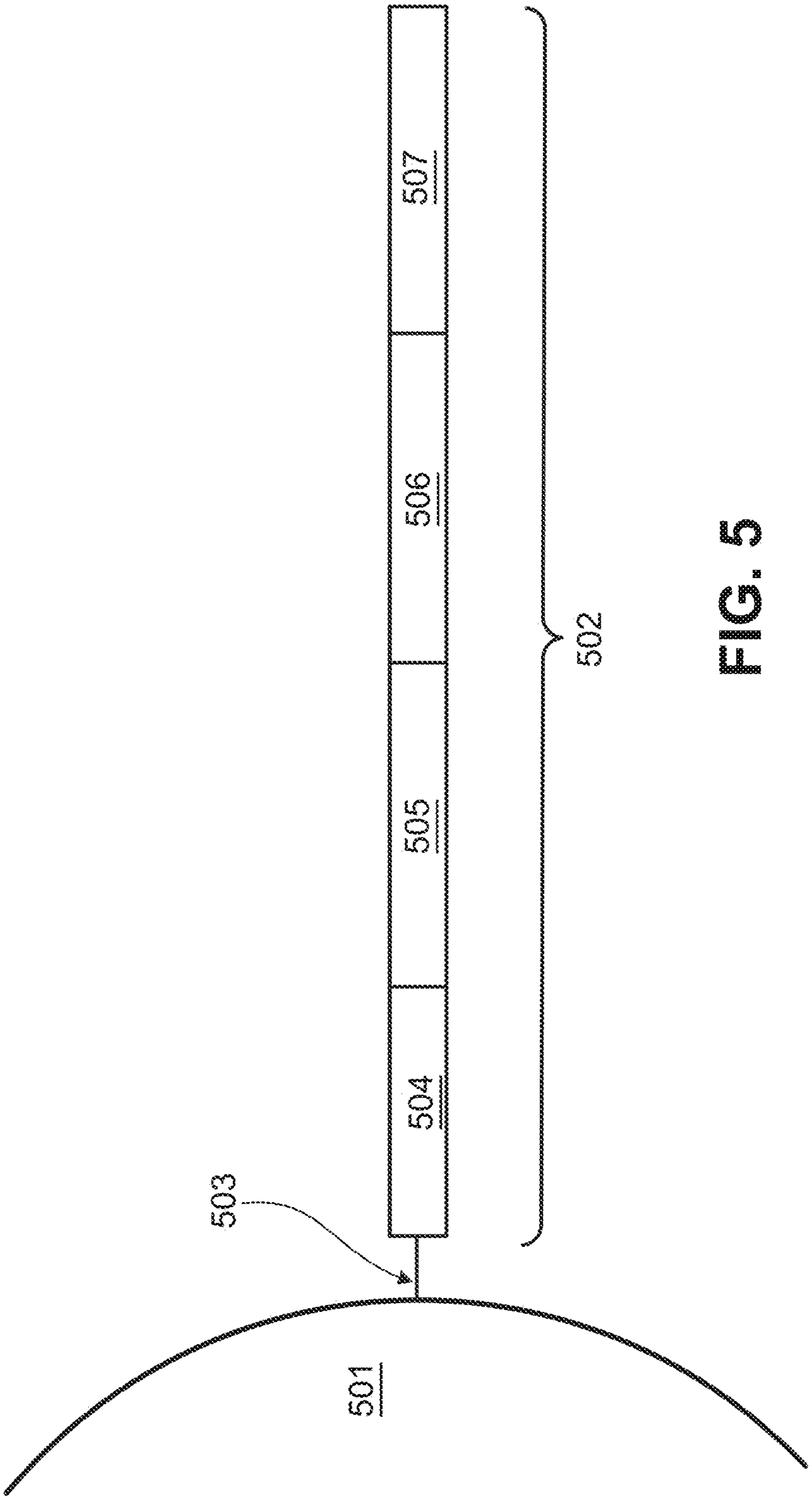
FIG. 5 is a schematic diagram showing an example of a barcoded capture probe, as described herein.

FIG. 5 is a schematic diagram showing an exemplary capture probe, as described herein. As shown, the capture probe 502 is optionally coupled to a feature 501 by a cleavage domain 503, such as a disulfide linker. The capture probe can include a functional sequence 504 that is useful for subsequent processing. The functional sequence 504 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 505. The capture probe can also include a unique molecular identifier (UMI) sequence 506. While FIG. 5 shows the spatial barcode 505 as being located upstream (5') of UMI sequence 506, it is to be understood that capture probes wherein UMI sequence 506 is located upstream (5') of the spatial barcode 505 is also suitable for use in any of the methods described herein. The capture probe can also include a capture domain 507 to facilitate capture of a target analyte. The capture domain can have a sequence complementary to a sequence of a nucleic acid analyte. The capture domain can have a sequence complementary to a connected probe described herein. The capture domain can have a sequence complementary to a analyte capture sequence present in an analyte capture agent. The capture domain can have a sequence complementary to a splint oligonucleotide. A splint oligonucleotide, in addition to having a sequence complementary to a capture domain of a capture probe, can have a sequence complementary to a sequence of a nucleic acid analyte, a portion of a connected probe described herein, a capture handle sequence described herein, and/or a methylated adaptor described herein.

Figure 6:
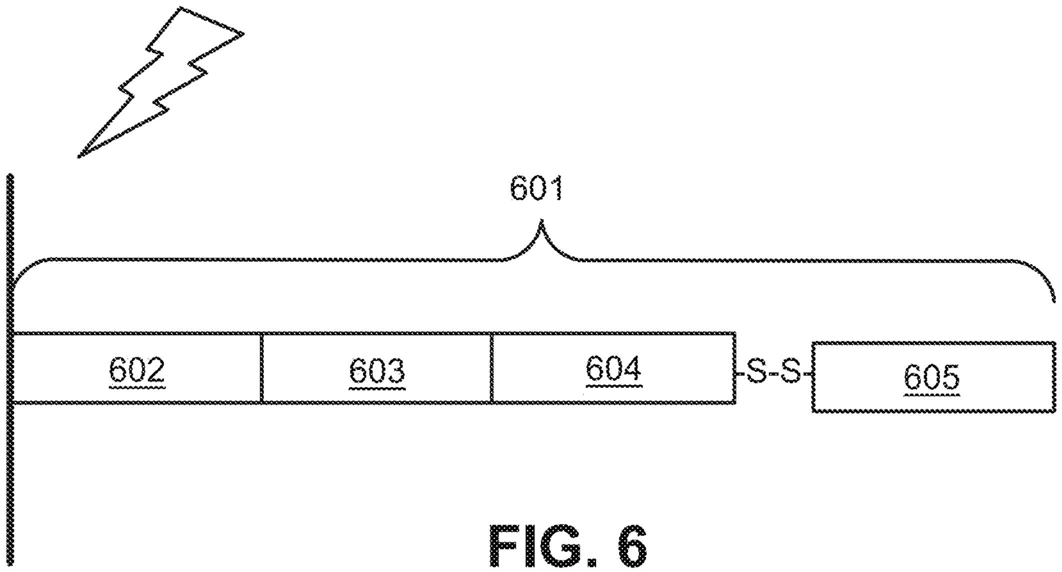
FIG. 6 shows a schematic illustrating a cleavable capture probe.

FIG. 6 is a schematic illustrating a cleavable capture probe, wherein the cleaved capture probe can enter into a non-permeabilized cell and bind to analytes within the sample. The capture probe 601 contains a cleavage domain 602, a cell penetrating peptide 603, a reporter molecule 604, and a disulfide bond (—S—S—). 605 represents all other parts of a capture probe, for example a spatial barcode and a capture domain.

Figure 7:
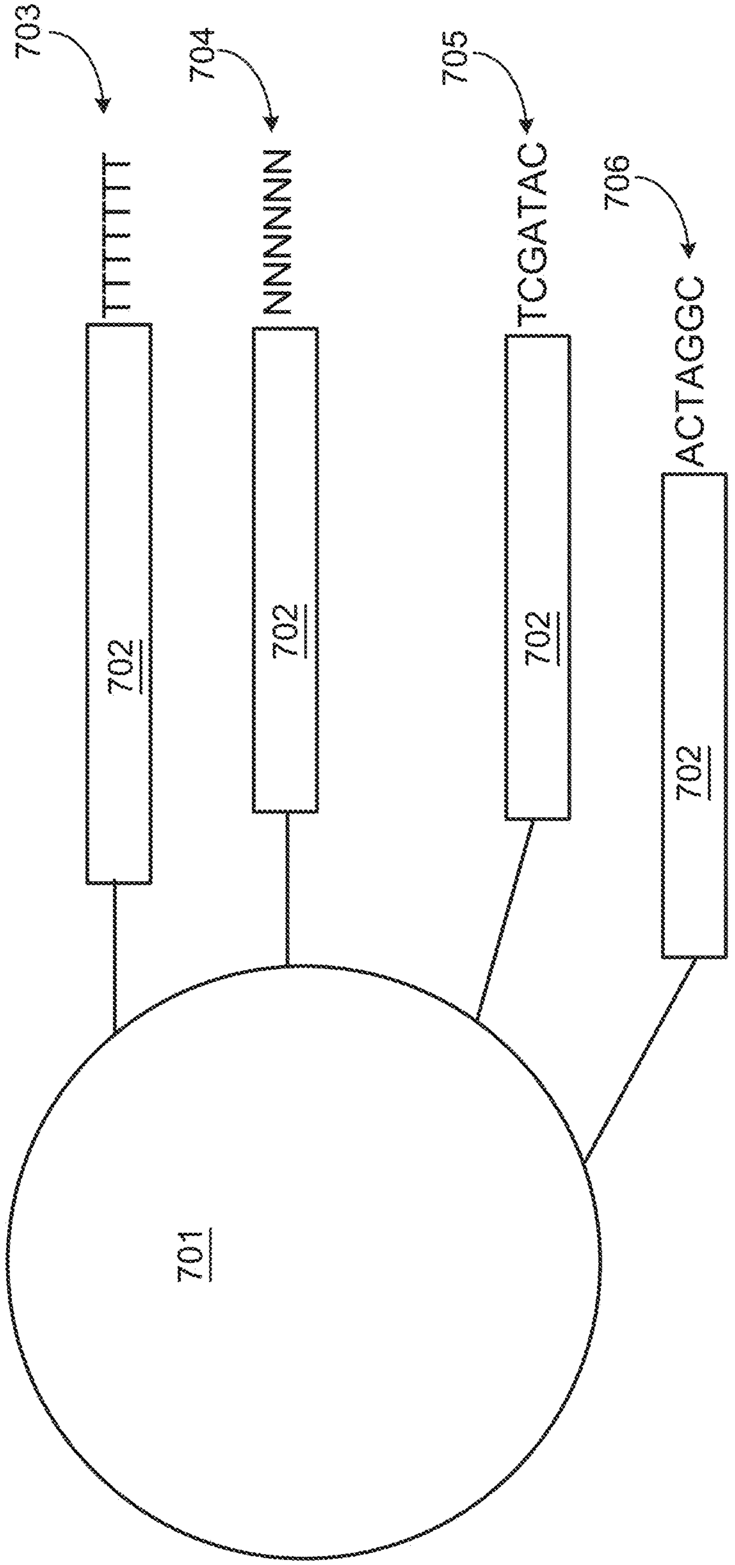
FIG. 7 shows exemplary capture domains on capture probes.

FIG. 7 is a schematic diagram of an exemplary multiplexed spatially-barcoded feature. In FIG. 7, the feature 701 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may include four different types of spatially-barcoded capture probes, each type of spatially-barcoded capture probe possessing the spatial barcode 702. One type of capture probe associated with the feature includes the spatial barcode 702 in combination with a poly(T) capture domain 703, designed to capture mRNA target analytes. A second type of capture probe associated with the feature includes the spatial barcode 702 in combination with a random N-mer capture domain 704 for gDNA analysis. A third type of capture probe associated with the feature includes the spatial barcode 702 in combination with a capture domain complementary to the analyte capture agent of interest 705. A fourth type of capture probe associated with the feature includes the spatial barcode 702 in combination with a capture probe that can specifically bind a nucleic acid molecule 706 that can function in a CRISPR assay (e.g., CRISPR/Cas9). While only four different capture probe-barcoded constructs are shown in FIG. 7, capture-probe barcoded constructs can be tailored for analyses of any given analyte associated with a nucleic acid and capable of binding with such a construct. For example, the schemes shown in FIG. 7 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 505 and functional sequences 504 are common to all of the probes attached to a given feature. In some embodiments, the UMI sequence 506 of a capture probe attached to a given feature is different from the UMI sequence of a different capture probe attached to the given feature.

Figure 8:
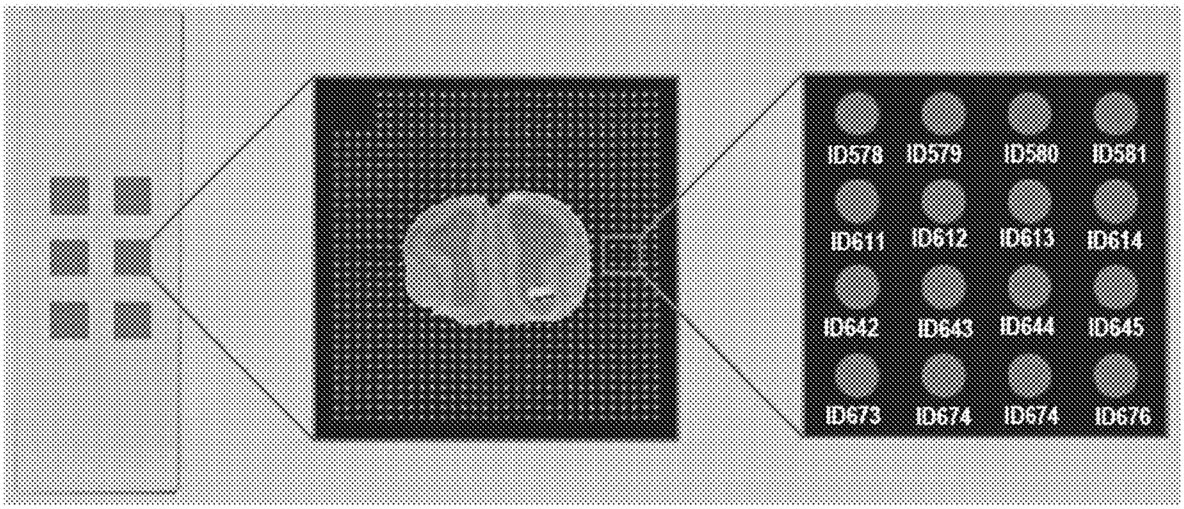
FIG. 8 shows an exemplary arrangement of barcoded features within an array.

FIG. 8 depicts an exemplary arrangement of barcoded features within an array. From left to right, FIG. 8 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

In some embodiments, more than one analyte type (e.g., nucleic acids and proteins) from a biological sample can be detected (e.g., simultaneously or sequentially) using any appropriate multiplexing technique, such as those described in Section (IV) of PCT Publication No. WO2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of PCT Publication No. WO2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. Sec, e.g., Credle et al., *Nucleic Acids Res.* 2017 Aug. 21; 45(14):e 128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., a T4 RNA ligase (Rnl2), a PBCV-1 DNA Ligase or *Chlorella* virus DNA Ligase, a single-stranded DNA ligase, or a T4 DNA ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNase H). In some instances, the ligation product is removed using heat. In some instances, the ligation product is removed using KOH. The released ligation product can then be captured by capture probes (e.g., instead of direct capture of an analyte) on an array, optionally amplified, and sequenced, thus determining the location and optionally the abundance of the analyte in the biological sample.

In some instances, one or both of the oligonucleotides may hybridize to genomic DNA (gDNA) which can lead to false positive sequencing data from ligation events on gDNA (off target) in addition to the desired (on target) ligation events on target nucleic acids, (e.g., mRNA). Thus, in some embodiments, the disclosed methods can include contacting the biological sample with a deoxyribonuclease (DNase). The DNase can be an endonuclease or exonuclease. In some embodiments, the DNase digests single- and/or double-stranded DNA. Suitable DNases include, without limitation, a DNase I and a DNase II. Use of a DNase as described can mitigate false positive sequencing data from off target gDNA ligation events.

Figure 9A:
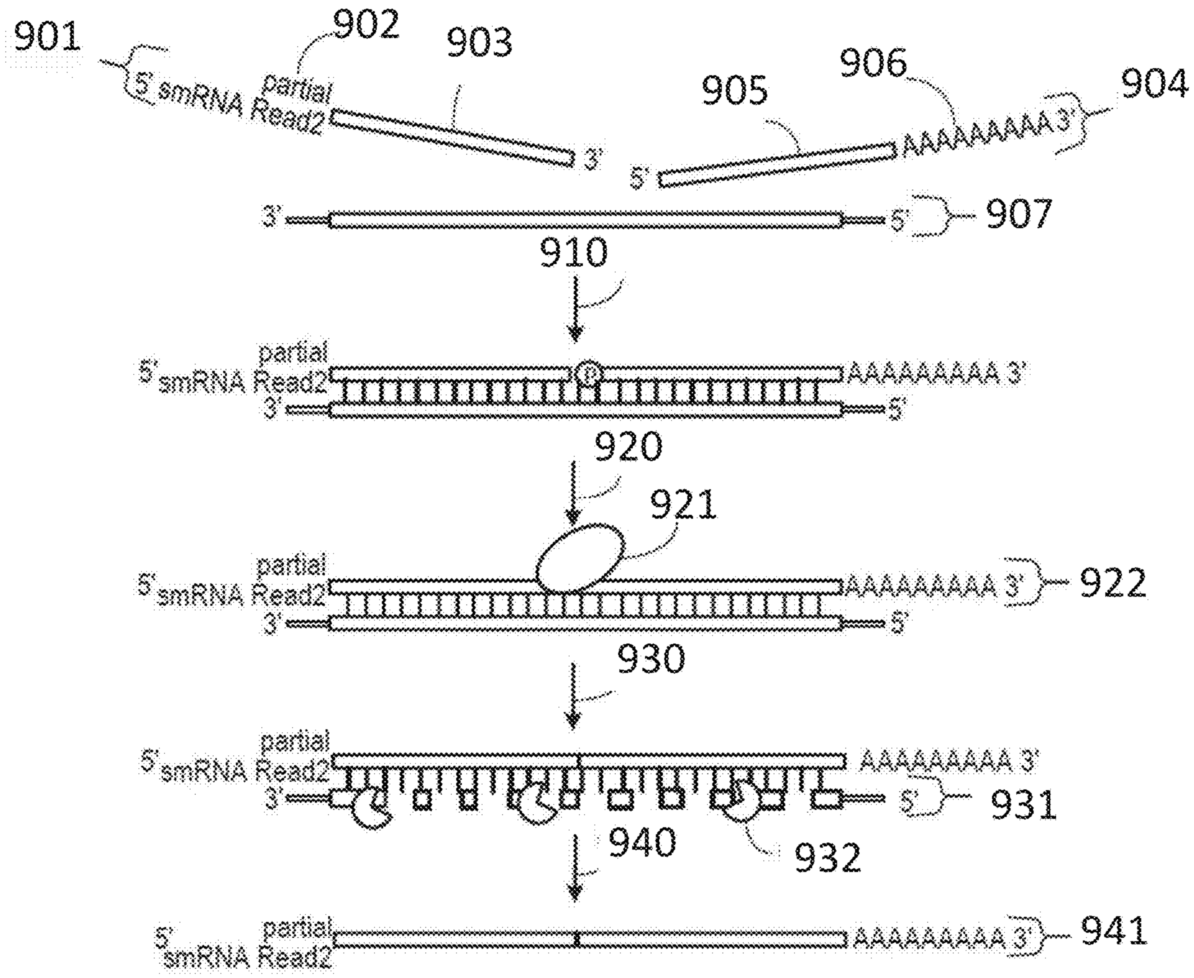
FIG. 9A shows and exemplary workflow for performing a templated capture and producing a ligation product.

A non-limiting example of templated ligation methods disclosed herein is depicted in FIG. 9A. After a biological sample is contacted with a substrate including a plurality of capture probes and contacted with (a) a first probe 901 having a target-hybridization sequence 903 and a primer sequence 902 and (b) a second probe 904 having a target-hybridization sequence 905 and a capture domain (e.g., a poly-A sequence) 906, the first probe 901 and a second probe 904 hybridize 910 to an analyte 907. A ligase 921 ligates 920 the first probe to the second probe thereby generating a ligation product 922. The ligation product is released 930 from the analyte 931 by digesting the analyte using an endoribonuclease 932. The sample is permeabilized 940 and the ligation product 941 is able to hybridize to a capture probe on the substrate. Methods and composition for spatial detection using templated ligation have been described in PCT Publ. No. WO 2021/133849 A1, U.S. Pat. Nos. 11,332,790 and 11,505,828, each of which is incorporated by reference in its entirety.

Figure 9B:
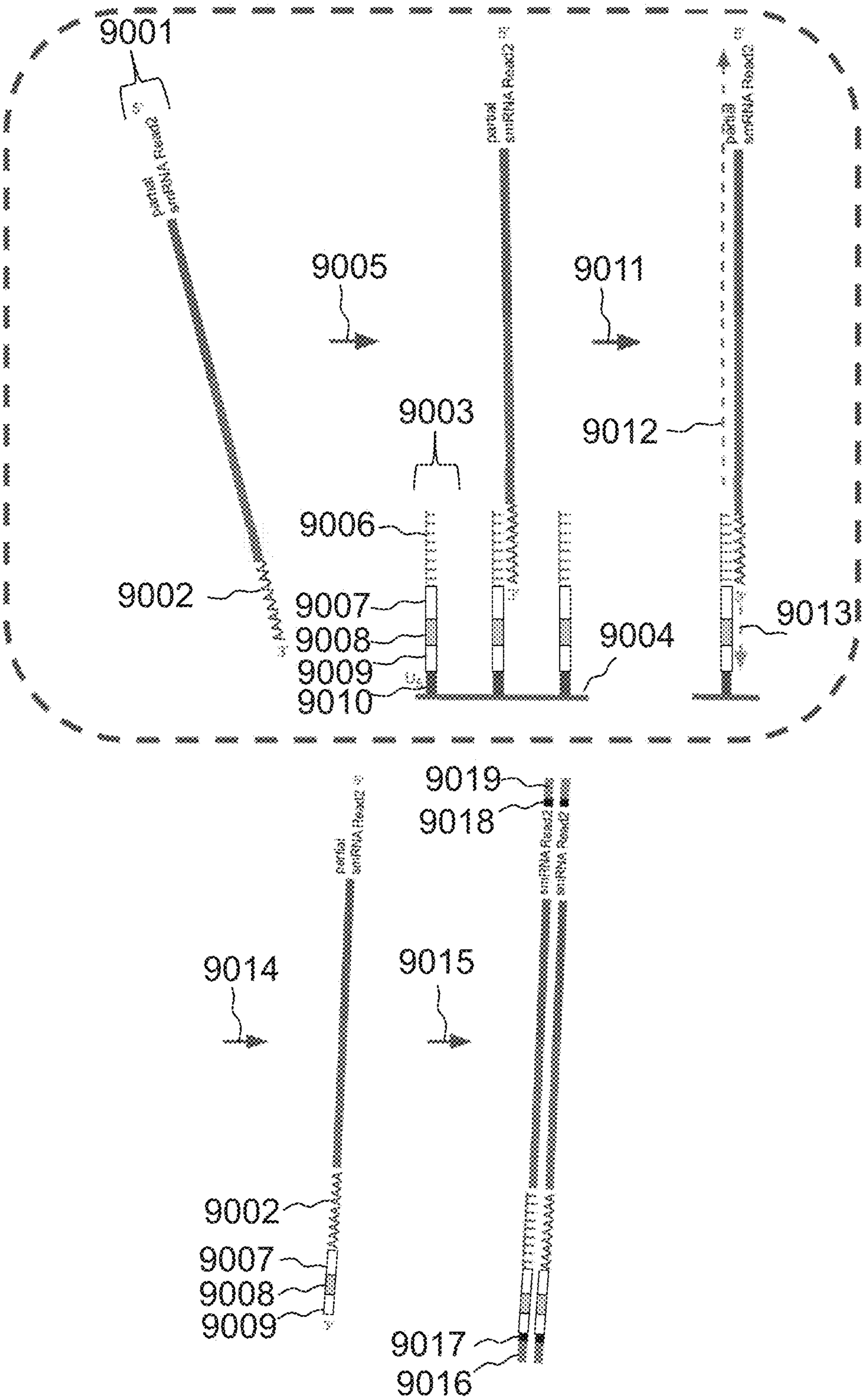
FIG. 9B shows an exemplary workflow for capturing a ligation product from FIG. 9A on a substrate.

In some embodiments, as shown in FIG. 9B, the ligation product 9001 includes a capture probe capture domain 9002, which can bind to a capture probe 9003 (e.g., a capture probe immobilized, directly or indirectly, on a substrate 9004). In some embodiments, methods provided herein include contacting 9005 a biological sample with a substrate 9004, wherein the capture probe 9003 is affixed to the substrate (e.g., immobilized to the substrate, directly or indirectly). In some embodiments, the capture probe capture domain 9002 of the ligated product specifically binds to the capture domain 9006. The capture probe can also include a unique molecular identifier (UMI) 9007, a spatial barcode 9008, a functional sequence 9009, and a cleavage domain 9010.

In some embodiments, methods provided herein include permeabilization of the biological sample such that the capture probe can more easily capture the ligation products (i.e., compared to no permeabilization). In some embodiments, reverse transcription (RT) reagents can be added to permeabilized biological samples. Incubation with the RT reagents can extend the capture probes 9011 to produce spatially-barcoded full-length cDNA 9012 and 9013 from the captured ligation products (e.g., ligation products).

In some embodiments, the extended ligation products can be denatured 9014 from the capture probe and transferred (e.g., to a clean tube) for amplification, and/or library construction. The spatially-barcoded ligation products can be amplified 9015 via PCR prior to library construction. P5 9016, i5 9017, i7 9018, and P7 9019, and can be used as sample indexes. The amplicons can then be sequenced using paired-end sequencing using TruSeq Read 1 and TruSeq Read 2 as sequencing primer sites.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of PCT Publication No. WO2020/176788 and/or Section (II)(b)(viii) U.S. Patent Application Publication No. 2020/0277663.

Figure 10:
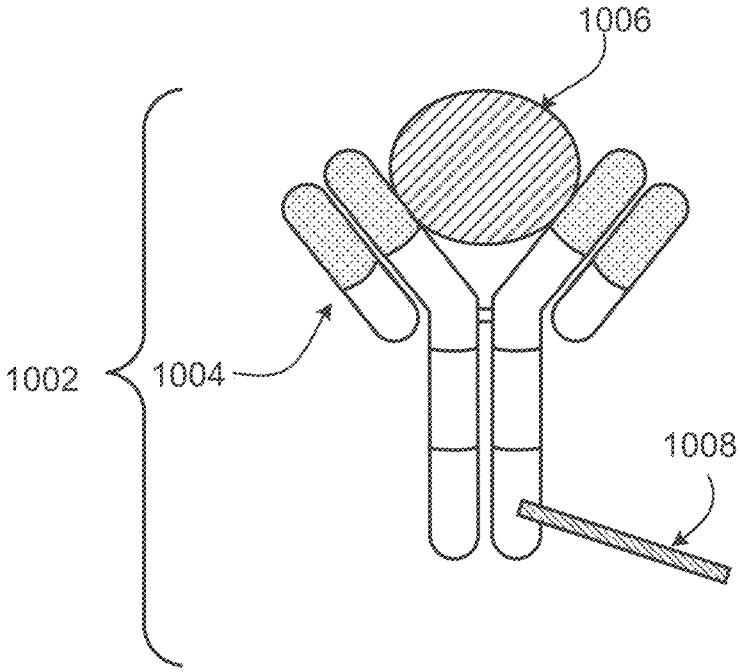
FIG. 10 is a schematic diagram of an exemplary analyte capture agent.

FIG. 10 is a schematic diagram of an exemplary analyte capture agent 1002 comprised of an analyte-binding moiety 1004 and an analyte-binding moiety barcode domain 1008. The exemplary analyte-binding moiety 1004 is a molecule capable of binding to an analyte 1006 and the analyte capture agent is capable of interacting with a spatially-barcoded capture probe. The analyte-binding moiety can bind to the analyte 1006 with high affinity and/or with high specificity. The analyte capture agent can include an analyte-binding moiety barcode domain 1008 which serves to identify the analyte binding moiety, and a capture domain which can hybridize to at least a portion or an entirety of a capture domain of a capture probe. The analyte-binding moiety 1004 can include a polypeptide and/or an aptamer. The analyte-binding moiety 1004 can include an antibody or antibody fragment (e.g., an antigen-binding fragment).

Figure 11:
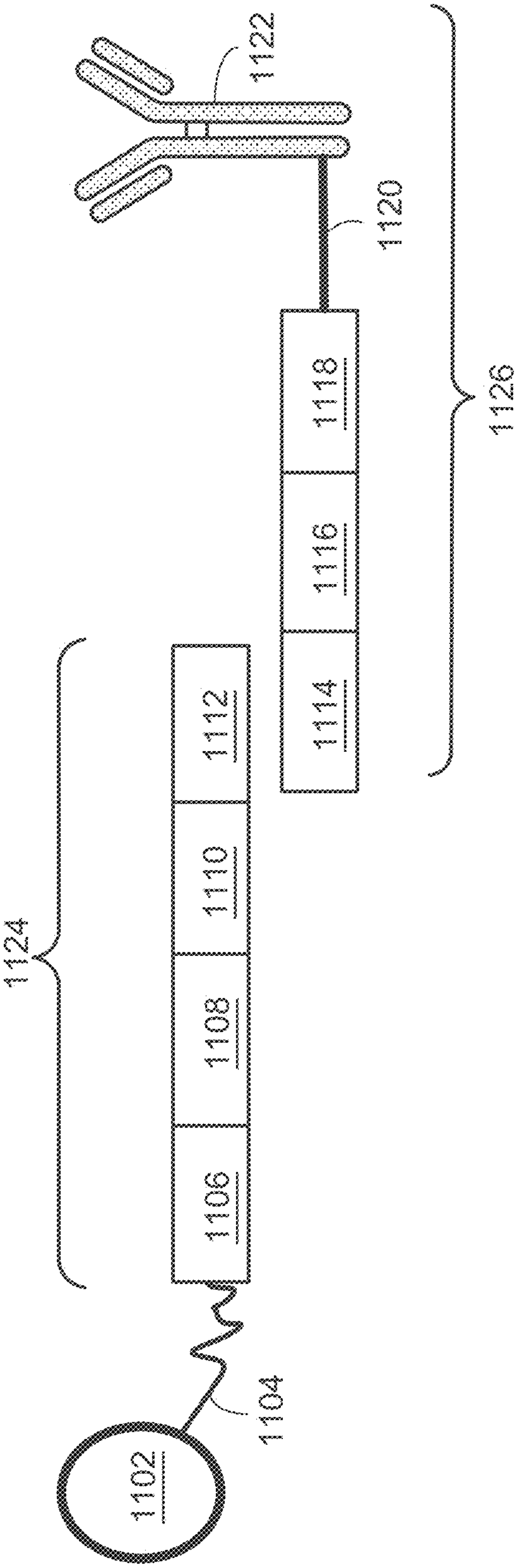
FIG. 11 is a schematic diagram depicting an exemplary interaction between a feature-immobilized capture probe 1124 and an analyte capture agent 1126.

FIG. 11 is a schematic diagram depicting an exemplary interaction between a feature-immobilized capture probe 1124 and an analyte capture agent 1126. The feature-immobilized capture probe 1124 can include a spatial barcode 1108 as well as functional sequences 1106 and a UMI 1110, as described elsewhere herein. The capture probe can be affixed 1104 to a feature such as a bead 1102. The capture probe can also include a capture domain 1112 that is capable of binding to an analyte capture agent 1126. The analyte-binding moiety barcode domain of the analyte capture agent 1126 can include a functional sequence 1118, analyte binding moiety barcode 1116, and an analyte capture sequence 1114 that is capable of binding (e.g., hybridizing) to the capture domain 1112 of the capture probe 1124. The analyte capture agent can also include a linker 1120 that allows the analyte-binding moiety barcode domain (e.g., including the functional sequence 1118, analyte binding barcode 1116, and analyte capture sequence 1114) to couple to the analyte binding moiety 1122. In some embodiments, the linker is a cleavable linker. In some embodiments, the cleavable linker is a photo-cleavable linker, a UV-cleavable linker, or an enzyme cleavable linker. In some instances, the cleavable linker is a disulfide linker. A disulfide linker can be cleaved by use of a reducing agent, such as dithiothreitol (DTT), Beta-mercaptoethanol (BME), or Tris (2-carboxyethyl) phosphine (TCEP).

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of PCT Publication No. WO2020/176788 and/or U.S. Patent Application Publication No. 2020/0277663. See, for example, the Exemplary embodiment starting with "In some non-limiting examples of the workflows described herein, the sample can be immersed . . . " of PCT Publication No. WO2020/176788 and/or U.S. Patent Application Publication No. 2020/0277663. See also, e.g., the Visium Spatial Gene Expression Reagent Kits User Guide (e.g., Rev F, dated January 2022); and/or the Visium Spatial Gene Expression Reagent Kits—Tissue Optimization User Guide (e.g., Rev E, dated February 2022).

In some embodiments, spatial analysis can be performed using dedicated hardware and/or software, such as any of the systems described in Sections (II)(c)(ii) and/or (V) of PCT Publication No. WO2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of PCT Publication No. WO2020/123320.

Suitable systems for performing spatial analysis can include components such as a chamber (e.g., a flow cell or scalable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Publication No. WO2021/102003 and/or U.S. Patent Application Publication No. 2021/0150707, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Publication No. WO2020/053655 and spatial analysis methods are generally described in PCT Publication No. WO2021/102039 and/or U.S. Patent Application Publication No. 2021/0155982, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of PCT Publication Nos. WO2020/123320, WO 2021/102005, and/or U.S. Patent Application Publication No. 2021/0158522, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

B. Methods, Compositions, Devices, and Systems for Capturing Analytes and Derivatives Thereof (i) Introduction Provided herein are methods, devices, compositions, and systems for analyzing the location and/or abundance of a nucleic acid or protein analyte in a biological sample. In some instances, the methods include aligning (i.e., sandwiching) a first substrate having the biological sample with a second substrate that includes a plurality of capture probes, thereby "sandwiching" the biological sample between the two substrates. Upon alignment of the biological sample with the substrate having a plurality of probes (in either instance), subsequent transfer of an analyte or analyte-derived molecule/intermediate agent, the location and/or abundance of an analyte (e.g., a nucleic acid or protein analyte) in a biological sample can be determined, as provided herein. The methods provide an advantage in that, prior to analyte or analyte-derived molecule capture by the capture probe, most—if not all—steps can be performed on a substrate that does not have capture probes, thereby providing a method that is cost effective.

Herein, Applicant has identified that modulating the reagent medium added after antibodies (e.g., oligonucleotide-tagged antibodies are added to the biological sample) used in the sandwiching process can increase the sensitivity and detection of proteins in a sample. Modulating the reagent medium after oligonucleotide-tagged antibody incubation includes adding mono- or bi-valent salts such as sodium chloride to the reagent medium used to release an analyte capture agent from a biological sample. It is further appreciated that including additional components, such as ethylene carbonate and/or glycerol, can further enhance detection.

Thus, disclosed herein are methods for analyzing an analyte in a biological sample mounted on a first substrate. In some instances, the method include (a) contacting the biological sample with a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and an capture handle sequence; (b) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; (c) when the biological sample is aligned with at least a portion of the array, contacting the biological sample and/or the array with a reagent medium comprising a monovalent salt or divalent salt, and releasing the capture agent barcode domain from the analyte capture agent and/or the analyte capture agent from the biological sample; and (d) hybridizing the capture handle sequence of the capture agent barcode domain to the capture domain.

The methods disclosed herein can also be performed on a single substrate, wherein the single substrate comprises capture probes, each having a capture domain and spatial barcode. In these instances, all steps of analyte or analyte-derived capture occur on the single substrate (e.g., there is no transfer of an analyte or analyte-derived molecule from one substrate to a second substrate). Thus, disclosed herein are methods for analyzing an analyte in a biological sample mounted on a first substrate comprising an array, wherein the array comprises a plurality of capture probes, wherein a capture probe of the plurality of capture probes comprises: (i) a spatial barcode and (ii) a capture domain. In some instances, the method comprises: (a) contacting the biological sample with a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and an capture handle sequence, (b) releasing the capture agent barcode domain from the analyte capture agent and/or the analyte capture agent from the biological sample using a reagent medium comprising a monovalent salt or divalent salt; and (c) hybridizing the capture handle sequence of the capture agent barcode domain to the capture domain.

In both setups (sandwiching or single substrate), after analyte or analyte-derived capture, the capture probe can be extended; the extended capture probe can be amplified, purified, and/or sequenced in order to determine the abundance and/or location of the analyte in the biological sample.

It is appreciated that the methods and systems provided herein can be applied to an analyte or an analyte-derived molecule(s). As used herein, an analyte derived molecule includes, without limitation, a connected probe (e.g., a ligation product) from a templated ligation assay (e.g., an RNA-templated ligation (RTL) assay), a product of reverse transcription (e.g., an extended capture probe), and an analyte binding moiety barcode (e.g., a binding moiety barcode that identifies that analyte binding moiety (e.g., an antibody)). In some embodiments, the analyte or analyte derived molecules comprise RNA and/or DNA. In some embodiments, the analyte or analyte derived molecules comprise one or more proteins.

In some instances, the methods, devices, compositions, and systems disclosed herein provide efficient release of an analyte or analyte derived molecule from a biological sample so that it can be captured or detected using methods disclosed herein.

In some instances, the methods, devices, compositions, and systems disclosed herein allow for detection of analytes or analyte derived molecules from different biological samples using a single array comprising a plurality of capture probes. As such, in some instances, the methods, devices, compositions, and systems allow for serial capture of analytes or analyte derived molecules from multiple samples. The analytes or analyte derived molecules can then be demultiplexed using biological-sample-specific index sequences to identify its biological sample origin.

Embodiments of the methods, devices, compositions, and systems disclosed herein are provided below.

(A) Methods of Increasing Detection of Proteins—Modifications to Reagent Medium

Provided herein are methods of detecting an analyte. The methods are based on modifications to reagent media used throughout the steps of the methods disclosed herein. For instance, after the oligo-tagged antibodies (e.g., analyte capture agents) are contacted with a sample, during the sandwich step which may involve permeabilization of the sample (see e.g., FIG. 12), a reagent medium can be introduced after the oligonucleotide-tagged antibodies (e.g., analyte capture agents) are introduced to the biological sample, wherein the reagent medium includes one or more of a divalent or monovalent salt, ethylene carbonate, and/or glycerol. In some instances, the monovalent salt or divalent salt in the reagent medium is at a concentration of about 100-750 mM. In some instances, the monovalent salt or divalent salt in the reagent medium is at a concentration of about 250 mM. In some instances, the monovalent salt or divalent salt in the reagent medium is at a concentration of about 500 mM. In some instances, the monovalent salt or divalent salt in the reagent medium is at a concentration between about 100 mM and 1000 mM (e.g., about 100, 200, 300, 400, 500, 600, 700, 800, 900, or 1000 mM). In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the monovalent salt is potassium chloride. In some instances, the divalent salt is magnesium chloride. In some instances, the potassium chloride in the reagent medium is at a concentration of about 250 mM. In some instances, the potassium chloride in the reagent medium is at a concentration of about 500 mM.

In some instances, the reagent medium comprises ethylene carbonate. In some instances, the ethylene carbonate in the reagent medium comprises about 0.5%-5% of the reagent medium (e.g., about 0.5%, 1%, 1.5%, 2%, 2.5%, 3%, 3.5%, 4%, 4.5%, 5%) of the reagent medium. In some instances, the ethylene carbonate in the reagent medium comprises about 2% of the reagent medium. In some instances, the reagent medium comprises glycerol. In some instances, the glycerol in the reagent medium comprises about 0.5%-5% of the reagent medium (e.g., about 0.5%, 1%, 1.5%, 2%, 2.5%, 3%, 3.5%, 4%, 4.5%, 5%) of the reagent medium. In some instances, the glycerol in the reagent medium comprises about 2.5% of the reagent medium.

In some embodiments, the amount of the plurality of analyte capture agents contacted with the biological sample is about 0.1 μg to about 1.5 μg (about 0.1, 0.2, 0.3, 0.4, 0.5, 0.6, 0.7, 0.8, 0.9, 1.0, 1.1, 1.2, 1.3, 1.4, or 1.5). In some instances, the amount of the plurality of analyte capture agents is about 0.6 μg to about 1.0 μg.

Figure 12:
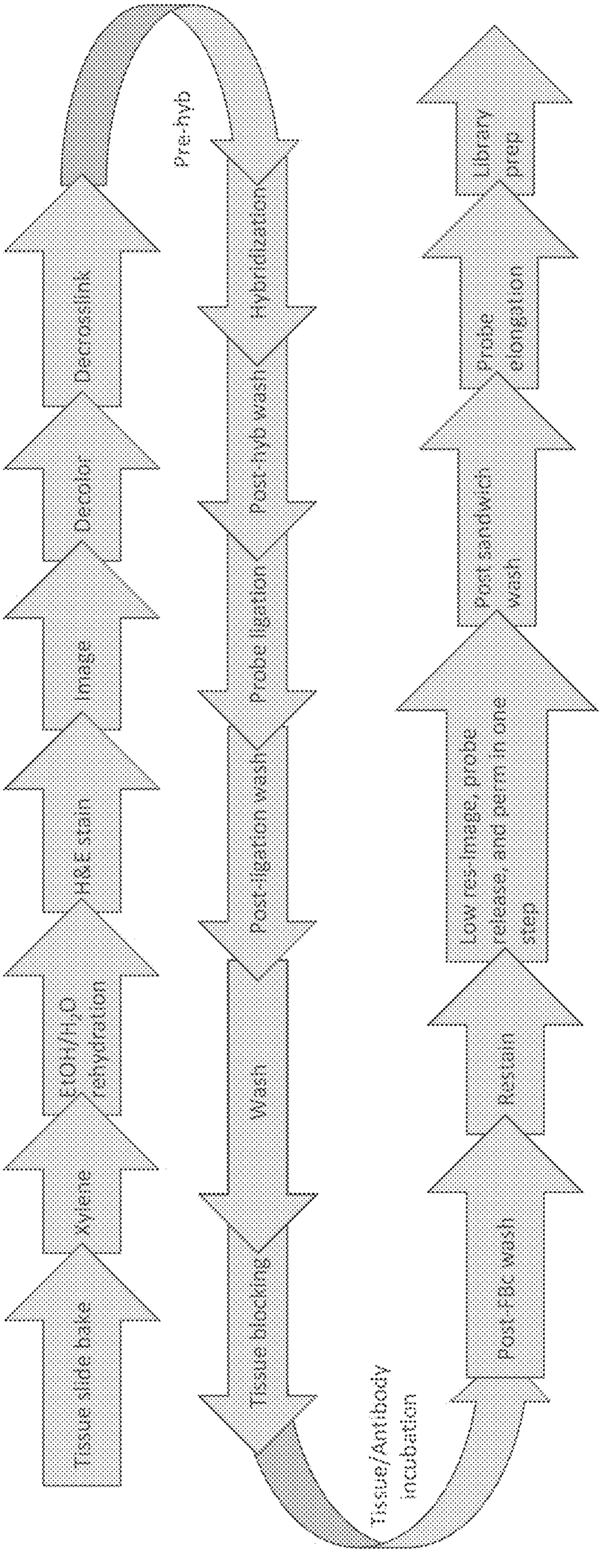
FIG. 12 shows a workflow of RNA and protein detection using the methods disclosed herein.
Figure 13A:
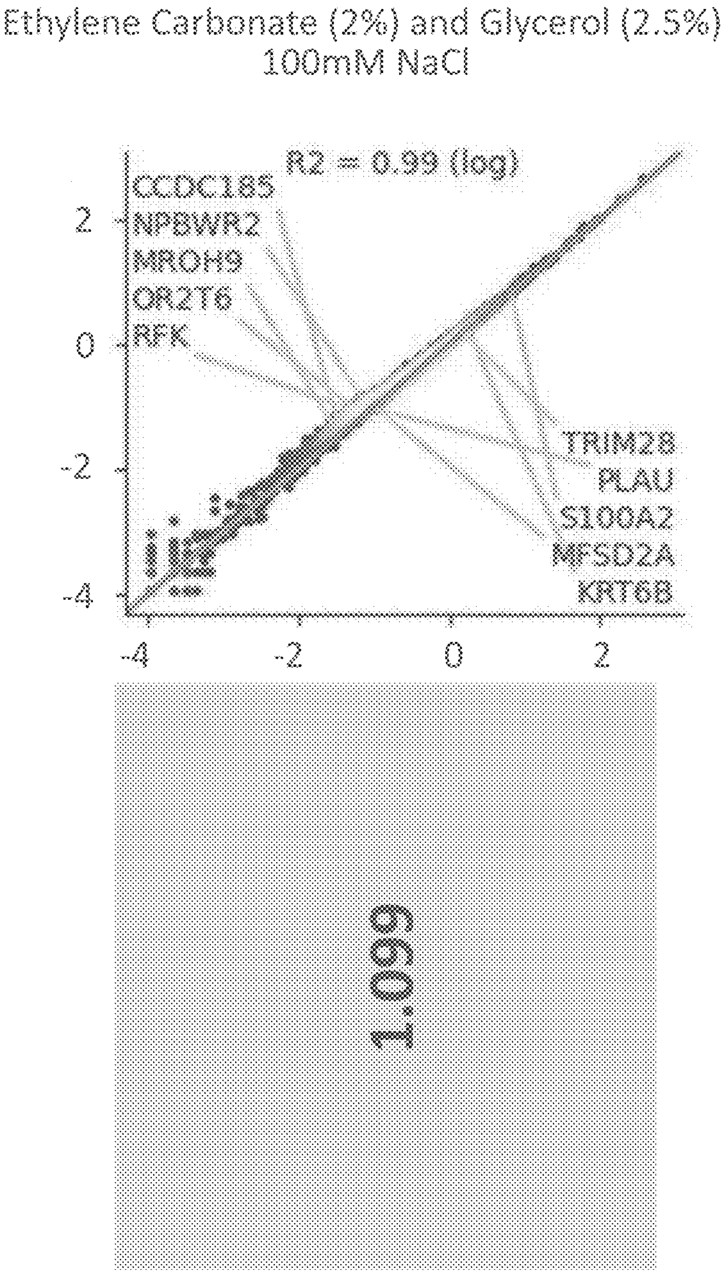
FIG. 13A shows a graph of unique molecular identifier (UMI) counts at a sodium chloride (NaCl) concentration of 100 mM.
Figure 13B:
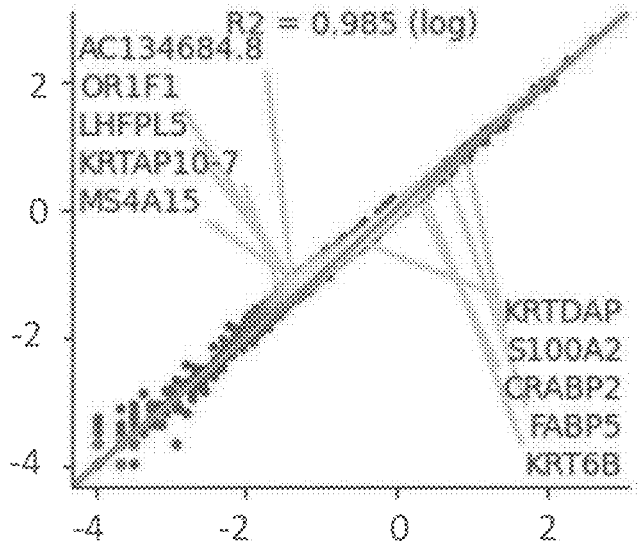
FIG. 13B shows a graph of unique molecular identifier (UMI) counts at a sodium chloride (NaCl) concentration of 250 mM.
Figure 13B:
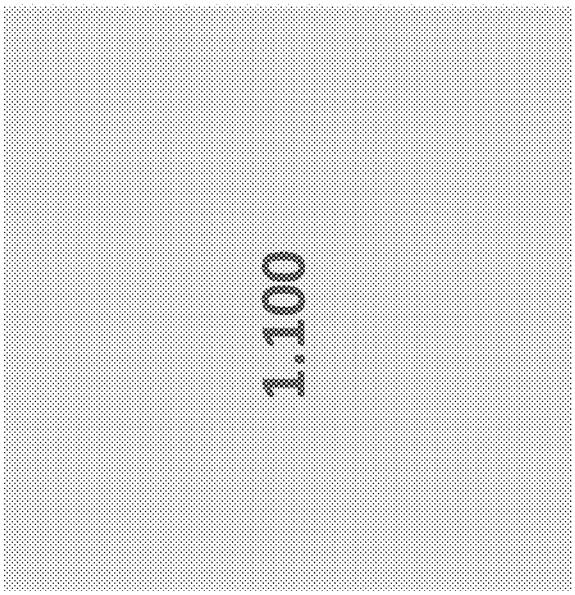
Figure 13C:
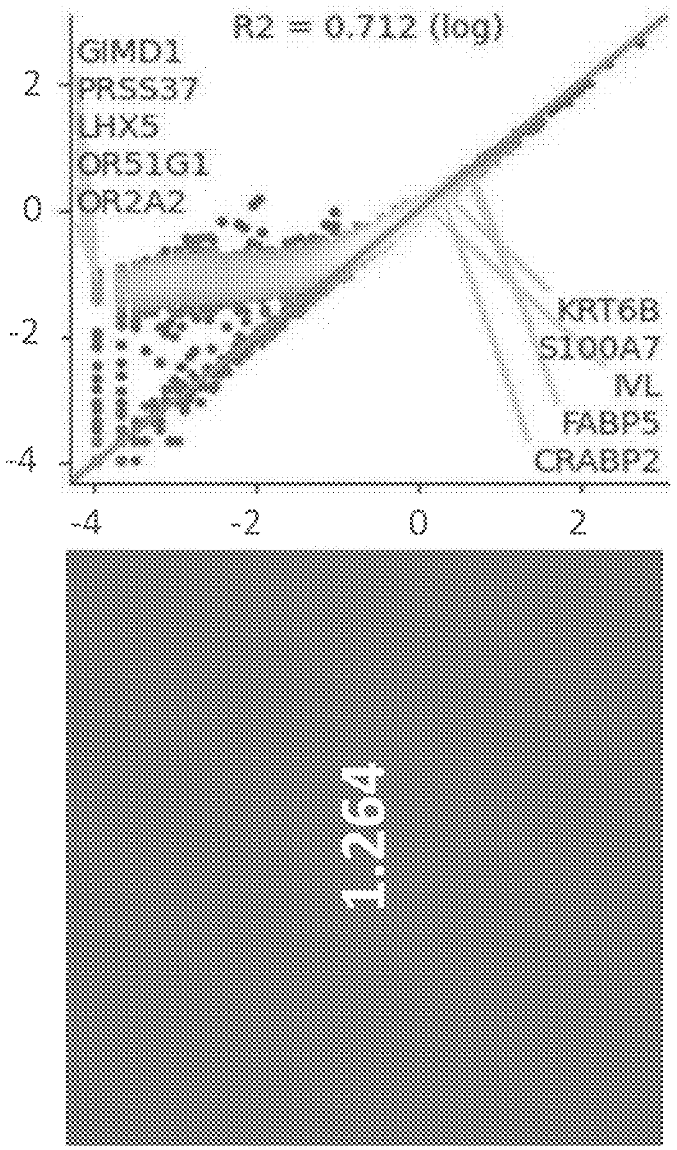
FIG. 13C shows a graph of unique molecular identifier (UMI) counts at a sodium chloride (NaCl) concentration of 500 mM.

It is appreciated that the modifications to the reagent medium described herein (e.g., at the permeabilization and/or release step) do not affect the RTL process performed prior to the incubation step (see FIG. 12). In particular, the selected protocol modifications described herein do not affect sensitivity to the RTL method nor do they increase non-specific UMI detection (e.g., in genomic DNA). At the same time, the methods that include modifications to the reagent medium decrease a "patchiness" phenotype (e.g., detecting uneven/low antibody UMI distribution) observed with protocol and reagents e.g., without a monovalent or divalent salt, such as NaCl.

In some instances, the correlation between analyte capture agent detection of proteins and nucleic acid capture using RTL methods is at about a 1:1 ratio (e.g., about 3:1, about 2:1, about 1:1, about 1:2, or about 1:3 of the protein to nucleic acid molecules detected)

In some embodiments, the reagent medium added after oligonucleotide-tagged antibody incubation includes a detergent. In some embodiments, the detergent is present at about 2% to about 10% (v/v) (e.g., about 2%, 3%, 4%, 5%, 6%, 7%, 8%, or 9% (v/v)). In some embodiments, the detergent is sarkosyl. In some embodiments, the sarkosyl is present at about 2% to about 10% (v/v). In some embodiments, the sarkosyl is present at about 3%, 4%, 5%, 6%, 7%, 8%, or 9% (v/v). In some embodiments, the reagent medium comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, 15K, 16K, 17K, 18K, 19K, or 20K. In some embodiments, the PEG is present at a concentration from about 2% to 25%, from about 4% to about 23%, from about 6% to about 21%, or from about 8% to about 20% (v/v).

The methods provided herein can also include antibody staining. In some embodiments, antibody staining includes the use of an antibody staining buffer. In some embodiments, the antibody staining buffer (e.g., a PBS-based buffer) includes a detergent (e.g., Tween-20, SDS, sarkosyl). In some embodiments, the antibody staining buffer includes a serum, such as for example, a goat serum. In some embodiments, the goat serum is from about 1% to about 10% (v/v), from about 2% to about 9% (v/v), from about 3% to about 8% (v/v), or about 4% to about 7% (v/v). In some embodiments, the antibody staining buffer includes dextran sulfate. In some embodiments, the dextran sulfate is at a concentration of about 1 mg/ml to about 20 mg/ml, from about 5 mg/ml to about 15 mg/ml, or from about 8 mg/ml to about 12 mg/ml.

(B) Exemplary First and Second Substrates

In some instances, the biological sample is placed (e.g., mounted or otherwise immobilized) on a first substrate. The first substrate can be any solid or semi-solid support upon which a biological sample can be mounted. In some instances, the first substrate is a slide. In some instances, the slide is a glass slide. In some embodiments, the substrate is made of glass, silicon, paper, hydrogel, polymer monoliths, or other material known in the art. In some embodiments, the first substrate is comprised of an inert material or matrix (e.g., glass slides) that has been functionalized by, for example, treating the substrate with a material comprising reactive groups which facilitate mounting of the biological sample.

In some embodiments, the first substrate does not comprise a plurality (e.g., array) of capture probes, each comprising a spatial barcode.

A substrate, e.g., a first substrate and/or a second substrate, can generally have any suitable form or format. For example, a substrate can be flat, curved, e.g., convexly or concavely curved. For example, a first substrate can be curved towards the area where the interaction between a biological sample, e.g., tissue sample, and a first substrate takes place. In some embodiments, a substrate is flat, e.g., planar, chip, or slide. A substrate can contain one or more patterned surfaces within the first substrate (e.g., channels, wells, projections, ridges, divots, etc.).

A substrate, e.g., a first substrate and/or second substrate, can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments wherein a substrate structure is flat, the substrate structure can be any appropriate type of support having a flat surface (e.g., a chip or a slide such as a microscope slide).

First and/or second substrates can optionally include various structures such as, but not limited to, projections, ridges, and channels. A substrate can be micropatterned to limit lateral diffusion of analytes (e.g., to improve resolution of the spatial analysis). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a first and/or second substrate is modified to contain one or more wells, using techniques such as (but not limited to) stamping, microetching, or molding techniques. In some embodiments in which a first and/or second substrate includes one or more wells, the first substrate can be a concavity slide or cavity slide. For example, wells can be formed by one or more shallow depressions on the surface of the first and/or second substrate. In some embodiments, where a first and/or second substrate includes one or more wells, the wells can be formed by attaching a cassette (e.g., a cassette containing one or more chambers) to a surface of the first substrate structure.

In some embodiments where the first and/or second substrate is modified to contain one or more structures, including but not limited to, wells, projections, ridges, features, or markings, the structures can include physically altered sites. For example, a first and/or second substrate modified with various structures can include physical properties, including, but not limited to, physical configurations, magnetic or compressive forces, chemically functionalized sites, chemically altered sites, and/or electrostatically altered sites. In some embodiments where the first substrate is modified to contain various structures, including but not limited to wells, projections, ridges, features, or markings, the structures are applied in a pattern. Alternatively, the structures can be randomly distributed.

In some embodiments, a first substrate includes one or more markings on its surface, e.g., to provide guidance for aligning at least a portion of the biological sample with a plurality of capture probes on the second substrate during a sandwich process disclosed herein. For example, the first substrate can include a sample area indicator identifying the sample area. In some embodiments, during a sandwiching process described herein the sample area indicator on the first substrate is aligned with an area of the second substrate comprising a plurality of capture probes. In some embodiments, the first and/or second substrate can include a fiducial mark. In some embodiments, the first and/or second substrate does not comprise a fiducial mark. In some embodiments, the first substrate does not comprise a fiducial mark and the second substrate comprises a fiducial mark. Such markings can be made using techniques including, but not limited to, printing, sand-blasting, and depositing on the surface.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., Applied Optics 46:421-427, 2007), the entire contents of which are incorporated herein by reference. In some embodiments, a fiducial marker can be a physical particle (e.g., a nanoparticle, a microsphere, a nanosphere, a bead, a post, or any of the other exemplary physical particles described herein or known in the art).

In some embodiments, a fiducial marker can be present on a first substrate to provide orientation of the biological sample. In some embodiments, a microsphere can be coupled to a first substrate to aid in orientation of the biological sample. In some examples, a microsphere coupled to a first substrate can produce an optical signal (e.g., fluorescence). In some embodiments, a quantum dot can be coupled to the first substrate to aid in the orientation of the biological sample. In some examples, a quantum dot coupled to a first substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Although not required, it can be advantageous to use a marker that can be detected using the same conditions (e.g., imaging conditions) used to detect a labelled cDNA.

In some embodiments, a fiducial marker can be randomly placed in the field of view. For example, an oligonucleotide containing a fluorophore can be randomly printed, stamped, synthesized, or attached to a first substrate (e.g., a glass slide) at a random position on the first substrate. A tissue section can be contacted with the first substrate such that the oligonucleotide containing the fluorophore contacts, or is in proximity to, a cell from the tissue section or a component of the cell (e.g., an mRNA or DNA molecule). An image of the first substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a first substrate). In this instance, a fiducial marker can be stamped, attached, or synthesized on the first substrate and contacted with a biological sample. Typically, an image of the sample and the fiducial marker is taken, and the position of the fiducial marker on the first substrate can be confirmed by viewing the image.

In some embodiments, a fiducial marker can be an immobilized molecule (e.g., a physical particle) attached to the first substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

A wide variety of different first substrates can be used for the foregoing purposes. In general, a first substrate can be any suitable support material. Exemplary first substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof.

Among the examples of first substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface, the nucleic acid immobilization can be increased. Such an enhancement can permit a relatively more densely packed formation (e.g., provide improved specificity and resolution).

In another example, a first substrate can be a flow cell. Flow cells can be formed of any of the foregoing materials, and can include channels that permit reagents, solvents, features, and analytes to pass through the flow cell. In some embodiments, a hydrogel embedded biological sample is assembled in a flow cell (e.g., the flow cell is utilized to introduce the hydrogel to the biological sample). In some embodiments, a hydrogel embedded biological sample is not assembled in a flow cell. In some embodiments, the hydrogel embedded biological sample can then be prepared and/or isometrically expanded as described herein.

Exemplary substrates similar to the first substrate (e.g., a substrate having no capture probes) and/or the second substrate are described in Section (I) above and in WO 2020/123320, which is hereby incorporated by reference in its entirety.

(ii) Capturing Protein for Spatial Detection Using Analyte Capture Agents

In some embodiments, the methods, compositions, devices, and systems provided herein utilize analyte capture agents for spatial detection. An analyte capture agent interacts both with a target analyte (e.g., a protein) and with a capture probe. Such analyte capture agents can be used to identify the analyte. In some embodiments, the analyte capture agent can include an analyte binding moiety and a capture agent barcode domain. In some embodiments, the analyte capture agent includes a linker. In some embodiments, the linker is a cleavable linker. In some embodiments, the cleavable linker is a photo-cleavable linker, a UV-cleavable linker, or an enzyme cleavable linker.

An analyte binding moiety is a molecule capable of binding to a specific analyte. In some embodiments, the analyte binding moiety comprises an antibody or antibody fragment (e.g., an antigen binding fragment). In some embodiments, the analyte binding moiety comprises a polypeptide and/or an aptamer. In some embodiments, the analyte is a protein (e.g., a protein on a surface of a cell or an intracellular protein).

A capture agent barcode domain can include a capture handle sequence which can hybridize to at least a portion or an entirety of a capture domain of a capture probe. In some embodiments, the capture handle sequence is complementary to a portion or entirety of a capture domain of a capture probe. In some embodiments, the capture handle sequence includes a poly (A) tail. In some embodiments, the capture handle sequence includes a sequence capable of binding a poly (T) domain. In some embodiments, the capture agent barcode domain comprises an analyte binding moiety barcode and a capture handle sequence. The analyte binding moiety barcode refers to a barcode that is associated with or otherwise identifies the analyte binding moiety, and the capture handle sequence can hybridize to a capture probe. In some embodiments, the capture handle sequence specifically binds to the capture domain of the capture probe. Other embodiments of an analyte capture agent useful in spatial analyte detection are described herein.

Provided herein are methods for analyzing an analyte in a biological sample including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and a capture handle sequence; (b) contacting the biological sample with a reagent medium including a monovalent salt or divalent salt and/or an agent for releasing the capture agent barcode domain from the analyte binding moiety, thereby releasing the capture agent barcode domain from the analyte binding moiety; and (c) hybridizing the capture handle sequence to a capture domain of a capture probe, wherein the capture probe includes (i) a spatial barcode and (ii) a capture domain. In some embodiments, methods for analyzing an analyte in a biological sample including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and a capture handle sequence; (b) contacting the biological sample with a reagent medium including a monovalent salt or divalent salt and/or an agent for releasing the analyte capture agent (e.g., including the analyte binding moiety and capture agent barcode domain) from the biological sample, thereby releasing the analyte capture agent from the biological sample; and (c) hybridizing the capture handle sequence to a capture domain of a capture probe, wherein the capture probe includes (i) a spatial barcode and (ii) a capture domain.

In some instances, the monovalent salt or divalent salt in the reagent medium is at a concentration of about 250 mM. In some instances, the monovalent salt or divalent salt in the reagent medium is at a concentration of about 500 mM. In some instances, the monovalent salt or divalent salt in the reagent medium is at a concentration between about 100 mM and 1000 mM (e.g., about 100, 200, 300, 400, 500, 600, 700, 800, 900, or 1000 mM). In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the monovalent salt is potassium chloride. In some instances, the divalent salt is magnesium chloride. In some instances, the reagent medium further comprises ethylene carbonate. In some instances, the ethylene carbonate in the reagent medium comprises about 2% of the reagent medium. In some instances, the reagent medium further comprises glycerol. In some instances, the glycerol in the reagent medium comprises about 2.5% of the reagent medium.

Also provided herein are methods for analyzing an analyte in a biological sample mounted on a first substrate including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) aligning the first substrate with a second substrate comprising an array, such that at least a portion of the biological sample is aligned with at least a portion of the array, wherein the array includes a plurality of capture probes, wherein a capture probe of the plurality of capture probes includes (i) a spatial barcode and (ii) a capture domain; (c) when the biological sample is aligned with at least a portion of the array, (i) releasing the capture agent barcode domain from the analyte and (ii) passively or actively migrating the capture agent barcode domain from the biological sample to the array; and (d) coupling the capture handle sequence to the capture domain.

The methods disclosed herein can also include a polishing step after analyte capture agent capture. In some instances, the polishing step includes treatment with a media comprising one or more of proteinase K, a buffer, and a detergent (e.g., sarkosyl). A polishing step in general aims to degrade protein, and overall allows for cleanup of a slide in order to improve data quality. In some instances, the polishing step is performed at 42 °C for 30 minutes.

In some instances, the polishing step includes treatment with a medium comprising urea. In some embodiments, the urea is at a concentration of about 0.5M to 3.0M. In some embodiments, the concentration of the urea is about 0.5, 1.0, 1.5, 2.0, 2.5, or about 3.0M.

Also provided herein are methods for analyzing an analyte in a biological sample mounted on a first substrate including (a) contacting the biological sample with a reagent medium that includes monovalent salt and/or divalent salt after the biological sample has been contacted with the analyte capture agents. In some instances, the monovalent salt or divalent salt in the reagent medium is at a concentration of about 250 mM. In some instances, the monovalent salt or divalent salt in the reagent medium is at a concentration of about 500 mM. In some instances, the monovalent salt or divalent salt in the reagent medium is at a concentration between about 100 mM and 1000 mM (e.g., about 100, 200, 300, 400, 500, 600, 700, 800, 900, or 1000 mM). In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the monovalent salt is potassium chloride. In some instances, the divalent salt is magnesium chloride. In some instances, the reagent medium comprises ethylene carbonate. In some instances, the ethylene carbonate in the reagent medium comprises about 2% of the reagent medium. In some instances, the reagent medium comprises glycerol. In some instances, the glycerol in the reagent medium comprises about 2.5% of the reagent medium. In some instances, an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and a capture handle sequence. Then, in some instances, the methods also include: (b) aligning the first substrate with a second substrate comprising an array, such that at least a portion of the biological sample is aligned with at least a portion of the array, wherein the array includes a plurality of capture probes, wherein a capture probe of the plurality of capture probes includes (i) a spatial barcode and (ii) a capture domain; (c) when the biological sample is aligned with at least a portion of the array, (i) releasing the analyte capture agent or capture agent barcode domain from the analyte and (ii) passively or actively migrating the capture agent barcode domain from the biological sample to the array; and (d) hybridizing the capture handle sequence to the capture domain.

In some embodiments, the method further includes determining (i) all or a part of the capture agent barcode domain, or a complement thereof; and (ii) the spatial barcode, or a complement thereof. In some embodiments, the method further includes using the determined sequence of (i) and (ii) to determine the location and/or abundance of the analyte in the biological sample.

In some embodiments, an analyte capture agent is introduced to a biological sample, wherein the analyte binding moiety specifically binds to a target analyte, and then the biological sample can be treated to release the analyte capture agent or the capture agent barcode domain from the biological sample. In some embodiments, the capture agent barcode domain can then migrate and bind to a capture domain of a capture probe, and the capture agent barcode domain can be extended to generate a spatial barcode complement at the end of the capture agent barcode domain. In some embodiments, the spatially-tagged capture agent barcode domain can be denatured from the capture probe, and analyzed using methods described herein.

In some embodiments, the reagent medium also includes a nuclease. In some embodiments, the nuclease includes an RNase. In some embodiments, the RNase is selected from RNase A, RNase C, RNase H, and RNase I. In some embodiments, the reagent medium further includes a permeabilization agent. In some embodiments, the releasing further includes simultaneously permeabilizing the biological sample and releasing the analyte capture agent or capture agent barcode domain from the analyte. In some embodiments, the permeabilization agent further includes a protease. In some embodiments, the protease is selected from trypsin, pepsin, elastase, or Proteinase K.

In some embodiments, the capture agent barcode domain is released from the analyte binding moiety by using a different stimulus that can include, but is not limited to, a proteinase (e.g., Proteinase K), an RNase, and UV light.

In some embodiments, the reagent medium further includes a detergent. In some embodiments, the detergent is selected from sodium dodecyl sulfate (SDS), sarkosyl, saponin, Triton X-100™, or Tween-20™. In some embodiments, the reagent medium includes less than 5 w/v % of a detergent selected from sodium dodecyl sulfate (SDS) and sarkosyl. In some embodiments, the reagent medium includes as least 5% w/v % of a detergent selected from SDS and sarkosyl. In some embodiments, the reagent medium does not include SDS or sarkosyl.

In some embodiments, the reagent medium further includes one or more of a monovalent salt, a divalent salt, ethylene carbonate, and glycerol. In some embodiments, the reagent medium includes a monovalent salt, a divalent salt, ethylene carbonate, glycerol, a nuclease (e.g., RNase), a protease (e.g., Proteinase K), a detergent, or a combination thereof.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about 35 minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, about 10 to about 45 minutes, about 10 to about 40 minutes, about 10 to about 35 minutes, about 10 to about 30 minutes, about 10 to about 25 minutes, about 10 to about 20 minutes, about 10 to about 15 minutes, about 15 to about 60 minutes, about 15 to about 55 minutes, about 15 to about 50 minutes, about 15 to about 45 minutes, about 15 to about 40 minutes, about 15 to about 35 minutes, about 15 to about 30 minutes, about 15 to about 25 minutes, about 15 to about 20 minutes, about 20 to about 60 minutes, about 20 to about 55 minutes, about 20 to about 50 minutes, about 20 to about 45 minutes, about 20 to about 40 minutes, about 20 to about 35 minutes, about 20 to about 30 minutes, about 20 to about 25 minutes, about 25 to about 60 minutes, about 25 to about 55 minutes, about 25 to about 50 minutes, about 25 to about 45 minutes, about 25 to about 40 minutes, about 25 to about 35 minutes, about 25 to about 30 minutes, about 30 to about 60 minutes, about 30 to about 55 minutes, about 30 to about 50 minutes, about 30 to about 45 minutes, about 30 to about 40 minutes, about 30 to about 35 minutes, about 35 to about 60 minutes, about 35 to about 55 minutes, about 35 to about 50 minutes, about 35 to about 45 minutes, about 35 to about 40 minutes, about 40 to about 60 minutes, about 40 to about 55 minutes, about 40 to about 50 minutes, about 40 to about 45 minutes, about 45 to about 60 minutes, about 45 to about 55 minutes, about 45 to about 50 minutes, about 50 to about 60 minutes, about 50 to about 55 minutes, or about 55 to about 60 minutes). In some embodiments, the biological sample and the array are contacted with the reagent medium for about 30 minutes.

Also provided herein are methods further including analyzing a different analyte in the biological sample. In some embodiments, the analysis of the different analyte includes (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) ligating the first probe and the second probe, thereby generating a connected probe (e.g., a ligation product) comprising the capture probe binding domain; and (c) hybridizing the capture probe binding domain of the connected probe (e.g., a ligation product) to the capture domain.

In some embodiments, the method further includes determining (i) all or part of the sequence of the connected probe (e.g., a ligation product), or a complement thereof, and (ii) the spatial barcode, or a complement thereof. In some embodiments, the method further includes using the determined sequence of (i), and (ii) to analyze the different analyte in the biological sample. In some embodiments, the releasing step further releases the connected probe (e.g., a ligation product) from the different analyte. In some embodiments, the different analyte is RNA. In some embodiments, the different analyte is mRNA.

In some embodiments, the capture probe comprises a poly(T) sequence. In some embodiments, the capture probe comprises a sequence substantially complementary to the capture handle sequence. In some embodiments, the capture probe comprises a functional domain. In some embodiments, the capture probe further comprises one or more functional domains, a unique molecular identifier (UMI), a cleavage domain, and combinations thereof.

In some instances, two analytes (e.g., two different proteins) in close proximity in a biological sample are detected by a first analyte-binding moiety and a second analyte-binding moiety, respectively. In some embodiments, a first analyte-binding moiety and/or the second analyte-binding moiety is an analyte capture agent (e.g., any of the exemplary analyte capture agents described herein). In some embodiments, the first analyte-binding moiety and/or the second analyte-binding moiety is a first protein. In some embodiments, the first analyte-binding moiety and/or the second analyte-binding moiety is an antibody. For example, the antibody can include, without limitation, a monoclonal antibody, recombinant antibody, synthetic antibody, a single domain antibody, a single-chain variable fragment (scFv), and or an antigen-binding fragment (Fab). In some embodiments, the first analyte-binding moiety binds to a cell surface analyte (e.g., any of the exemplary cell surface analytes described herein). In some embodiments, binding of the analyte is performed metabolically. In some embodiments, binding of the analyte is performed enzymatically. In some embodiments, the methods include a secondary antibody that binds to a primary antibody, enhancing its detection.

In some embodiments, the first analyte-binding moiety and the second analyte-binding moiety each bind to the same analyte. In some embodiments, the first analyte-binding moiety and/or second analyte-binding moiety each bind to a different analyte. For example, in some embodiments, the first analyte-binding moiety binds to a first polypeptide and the second analyte-binding moiety binds to a second polypeptide.

In some embodiments of any of the methods of determining a location of at least one analyte in a biological sample, a first and/or a second oligonucleotide are bound (e.g., conjugated or otherwise attached using any of the methods described herein) to a first analyte-binding moiety and/or a second analyte-binding moiety, respectively.

In some embodiments of any of the methods of determining a location of at least one analyte in a biological sample as described herein, a second oligonucleotide is bound (e.g., conjugated or otherwise attached using any of the methods described herein) to a second analyte-binding moiety. For example, the second oligonucleotide can be covalently linked to the second analyte-binding moiety. In some embodiments, the second oligonucleotide is bound to the second analyte-binding moiety via its 5' end. In some embodiments, the second oligonucleotide includes a free 3' end. In some embodiments the second oligonucleotide is bound to the second analyte-binding moiety via its 3' end. In some embodiments, the second oligonucleotide includes a free 5' end.

In some embodiments, the oligonucleotides are bound to the first and/or second analyte-binding moieties via a linker (e.g., any of the exemplary linkers described herein). In some embodiments, the linker is a cleavable linker. In some embodiment, the linker is a linker with photo-sensitive chemical bonds (e.g., photo-cleavable linkers). In some embodiments, the linker is a cleavable linker that can undergo induced dissociation.

In some embodiments, the oligonucleotides are bound (e.g., attached via any of the methods described herein) to an analyte-binding domain via a 5' end.

In some embodiments, a barcode is used to identify the analyte-binding moiety to which it is bound. The barcode can be any of the exemplary barcodes described herein. In some embodiments, the first and/or second oligonucleotide include a capture probe binding domain sequence. For example, a capture probe binding domain sequence can be a poly(A) sequence when the capture domain sequence is a poly(T) sequence.

In some embodiments, a third oligonucleotide (e.g., a splint oligonucleotide) hybridizes to both the first and second oligonucleotides and enables ligation of the first oligonucleotide and the second oligonucleotide. In some embodiments, a ligase is used. In some aspects, the ligase includes a DNA ligase. In some aspects, the ligase includes a RNA ligase. In some aspects, the ligase includes T4 DNA ligase. In some embodiments, the ligase is a *Chlorella* virus DNA ligase.

(iii) Capturing Nucleic Acid Analytes Using RNA-Templated Ligation

In some embodiments, the methods, devices, compositions, and systems described herein utilize RNA-templated ligation to detect the analyte. As used herein, spatial "RNA-templated ligation," or "RTL" or simply "templated ligation" is a process wherein individual probes (e.g., a first probe, a second probe) in a probe pair hybridize to adjacent sequences of an analyte (e.g., an RNA molecule) in a biological sample (e.g., a tissue sample). The RTL probes are then coupled (e.g., ligated) together, thereby creating a connected probe (e.g., a ligation product). RNA-templated ligation is disclosed in PCT Publ. No. WO 2021/133849 A1 and US Publ. No. US 2021/0285046 A1, each of which is incorporated by reference in its entirety.

As shown in FIG. 12, RTL steps can be performed prior to oligo-tagged antibody (e.g., analyte capture agent) incubation.

An advantage to using RTL is that it allows for enhanced detection of analytes (e.g., low expressing analytes) because both probes must hybridize to the analyte in order for the coupling (e.g., ligating) reaction to occur. As used herein, "coupling" refers to an interaction between two probes that results in a single connected probe that comprises the two probes. In some instances, coupling is achieved through ligation. In some instances, coupling is achieved through extension of one probe to the second probe followed by ligation. In some instances, coupling is achieved through hybridization (e.g., using a third probe that hybridized to each of the two probes) followed by extension of one probe or gap filling of the sequence between the two probes using the third probe as a template.

The connected probe (e.g., ligation product) that results from the coupling (e.g., ligation) of the two probes can serve as a proxy for the target analyte, as such an analyte derived molecule. Further, it is appreciated that probe pairs can be designed to cover any gene of interest. For example, a pair of probes can be designed so that each analyte, e.g., a whole exome, a transcriptome, a genome, can conceivably be detected using a probe pair.

In some instances, disclosed herein are methods for analyzing an analyte in a biological sample comprising (a) hybridizing a first probe and a second probe to the analyte, wherein the first probe and the second probe each comprise a sequence that is substantially complementary to adjacent sequences of the analyte, and wherein the second probe comprises a capture probe binding domain; (b) coupling the first probe and the second probe, thereby generating a connected probe (e.g., a ligation product) comprising the capture probe binding domain; (c) contacting the biological sample with a reagent medium comprising a permeabilization agent and an agent for releasing the connected probe (e.g., a ligation product), thereby (i) permeabilizing the biological sample and (ii) releasing the connected probe (e.g., a ligation product) from the analyte; and (d) hybridizing the capture probe binding domain of the connected probe (e.g., a ligation product) to a capture domain of a capture probe, wherein the capture probe comprises: (i) a spatial barcode and (ii) a capture domain.

Also provided herein are methods for analyzing an analyte in a biological sample mounted on a first substrate including (a) hybridizing a first probe and a second probe to the analyte, wherein the first probe and the second probe each include a sequence that is substantially complementary to adjacent sequences of the analyte, and wherein the second probe includes a capture probe binding domain; (b) coupling (e.g., ligating) the first probe and the second probe, thereby generating a connected probe (e.g., a ligation product) including the capture probe binding domain; (c) aligning the first substrate with a second substrate including an array, such that at least a portion of the biological sample is aligned with at least a portion of the array, wherein the array includes a plurality of capture probes, wherein a capture probe of the plurality of capture probes includes: (i) a spatial barcode and (ii) a capture domain; (d) when the biological sample is aligned with at least a portion of the array, (i) releasing the connected probe (e.g., a ligation product) from the analyte and (ii) passively or actively migrating the connected probe (e.g., a ligation product) from the biological sample to the array; and (c) hybridizing the capture probe binding domain of the connected probe (e.g., a ligation product) to the capture domain.

In some embodiments, the process of transferring the connected probe (e.g., a ligation product) from the first substrate to the second substrate is referred to as a "sandwich" process. The sandwich process is described in PCT Patent Application Publication No. WO 2020/123320, which is incorporated by reference in its entirety. Described herein are methods in which an array with capture probes located on a substrate and a biological sample located on a different substrate, are contacted such that the array is in contact with the biological sample (e.g., the substrates are sandwiched together). In some embodiments, the array and the biological sample can be contacted (e.g., sandwiched), without the aid of a substrate holder. In some embodiments, the array and biological sample substrates can be placed in a substrate holder (e.g., an array alignment device) designed to align the biological sample and the array. For example, the substrate holder can have placeholders for two substrates. In some embodiments, an array including capture probes can be positioned on one side of the substrate holder (e.g., in a first substrate placeholder). In some embodiments, a biological sample can be placed on the adjacent side of the substrate holder in a second placeholder. In some embodiments, a hinge can be located between the two substrate placeholders that allows the substrate holder to close, e.g., make a sandwich between the two substrate placeholders. In some embodiments, when the substrate holder is closed the biological sample and the array with capture probes are contacted with one another under conditions sufficient to allow analytes present in the biological sample to interact with the capture probes of the array. For example, dried permeabilization reagents can be placed on the biological sample and rehydrated. A permeabilization solution can be flowed through the substrate holder to permeabilize the biological sample and allow analytes in the biological sample to interact with the capture probes. Additionally, the temperature of the substrates or permeabilization solution can be used to initiate or control the rate of permeabilization. For example, the substrate including the array, the substrate including the biological sample, or both substrates can be held at a low temperature to slow diffusion and permeabilization efficiency. Once sandwiched, in some embodiments, the substrates can be heated to initiate permeabilization and/or increase diffusion efficiency. Transcripts that are released from the permeabilized tissue can diffuse to the array and be captured by the capture probes. The sandwich can be opened, and cDNA synthesis can be performed on the array.

In some embodiments, the methods as disclosed herein include hybridizing of one or more probe pairs (e.g., RTL probes) to adjacent or nearby sequences of a target analyte (e.g., RNA; e.g., mRNA) of interest. In some embodiments, the probe pairs include sequences that are complementary or substantially complementary to an analyte. For example, in some embodiments, each probe includes a sequence that is complementary or substantially complementary to an mRNA of interest (e.g., to a portion of the sequence of an mRNA of interest). In some embodiments, each target analyte includes a first target region and a second target region. In some embodiments, the methods include providing a plurality of first probes and a plurality of second probes, wherein a pair of probes for a target analyte comprises both a first and second probe. In some embodiments, a first probe hybridizes to a first target region of the analyte, and the second probe hybridizes to a second, adjacent or nearly adjacent target region of the analyte.

In some instances, the probes are DNA molecules. In some instances, the first probe is a DNA molecule. In some instances, the second probe is a DNA molecule. In some instances, the first probe comprises at least two ribonucleic acid bases at the 3' end. In some instances, the second probe comprises a phosphorylated nucleotide at the 5' end.

RTL probes can be designed using methods known in the art. In some instances, probe pairs are designed to cover an entire transcriptome of a species (e.g., a mouse or a human). In some instances, RTL probes are designed to cover a subset of a transcriptome (e.g., a mouse or a human). In some instances, the methods disclosed herein utilize about 500, about 1000, about 2000, about 3000, about 4000, about 5000, about 6000, about 7000, about 8000, about 9000, about 10,000, about 15,000, about 20,000, or more probe pairs.

In some embodiments, one of the probes of the pair of probes for RTL includes a poly(A) sequence or a complement thereof. In some instances, the poly(A) sequence or a complement thereof is on the 5' end of one of the probes. In some instances, the poly(A) sequence or a complement thereof is on the 3' end of one of the probes. In some embodiments, one probe of the pair of probes for RTL includes a degenerate or UMI sequence. In some embodiments, the UMI sequence is specific to a particular target or set of targets. In some instances, the UMI sequence or a complement thereof is on the 5' end of one of the probes. In some instances, the UMI sequence or a complement thereof is on the 3' end of one of the probes.

In some instances, the first and second target regions of an analyte are directly adjacent to one another. In some embodiments, the complementary sequences to which the first probe and the second probe hybridize are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probes may first be filled prior to coupling (e.g., ligation), using, for example, dNTPs in combination with a polymerase such as polymerase mu, DNA polymerase, RNA polymerase, reverse transcriptase, VENT polymerase, Taq polymerase, and/or any combinations, derivatives, and variants (e.g., engineered mutants) thereof. In some embodiments, when the first and second probes are separated from each other by one or more nucleotides, deoxyribonucleotides are used to extend and couple (e.g., ligate) the first and second probes.

In some instances, the first probe and the second probe hybridize to an analyte on the same transcript. In some instances, the first probe and the second probe hybridize to an analyte on the same exon. In some instances, the first probe and the second probe hybridize to an analyte on different exons. In some instances, the first probe and the second probe hybridize to an analyte that is the result of a translocation event (e.g., in the setting of cancer). The methods provided herein make it possible to identify alternative splicing events, translocation events, and mutations that change the hybridization rate of one or both probes (e.g., single nucleotide polymorphisms, insertions, deletions, point mutations).

In some embodiments, the first and/or second probe as disclosed herein includes at least two ribonucleic acid bases at the 3' end; a functional sequence; a phosphorylated nucleotide at the 5' end; and/or a capture probe binding domain. In some embodiments, the functional sequence is a primer sequence.

The "capture probe binding domain" is a sequence that is complementary to a particular capture domain present in a capture probe. In some embodiments, the capture probe binding domain includes a poly(A) sequence. In some embodiments, the capture probe binding domain includes a poly-uridine sequence, a poly-thymidine sequence, or a combination thereof. In some embodiments, the capture probe binding domain includes a random sequence (e.g., a random hexamer or octamer). In some embodiments, the capture probe binding domain is complementary to a capture domain in a capture probe that detects a particular target(s) of interest. In some embodiments, a capture probe binding domain blocking moiety that interacts with the capture probe binding domain is provided. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a connected probe (e.g., a ligation product)) to a capture probe. In some embodiments, a capture probe binding domain blocking moiety comprises a poly-uridine sequence, a poly-thymidine sequence, or a combination thereof.

Hybridization of the probes to the target analyte can occur at a target having a sequence that is 100% complementary to the probe(s). In some embodiments, hybridization can occur at a target having a sequence that is at least (e.g. at least about) 80%, at least (e.g. at least about) 85%, at least (e.g. at least about) 90%, at least (e.g. at least about) 95%, at least (e.g. at least about) 96%, at least (e.g. at least about) 97%, at least (e.g. at least about) 98%, or at least (e.g. at least about) 99% complementary to the probe(s). After hybridization, in some embodiments, the first probe is extended. After hybridization, in some embodiments, the second probe is extended. For example, in some instances a first probe hybridizes to a target sequence upstream for a second oligonucleotide probe, whereas in other instances a first probe hybridizes to a target sequence downstream of a second probe.

In some embodiments, methods disclosed herein include a wash step after hybridizing the first and the second probes. The wash step removes any unbound oligonucleotides and can be performed using any technique known in the art. In some embodiments, a pre-hybridization buffer is used to wash the sample. In some embodiments, a phosphate buffer is used. In some embodiments, multiple wash steps are performed to remove unbound oligonucleotides. For example, it is advantageous to decrease the amount of unhybridized probes present in a biological sample as they may interfere with downstream applications and methods.

In some embodiments, after hybridization of probes (e.g., first and the second probes) to the target analyte, the probes (e.g., the first probe and the second probe) are coupled (e.g., ligated) together, creating a single connected probe (e.g., a ligation product) that is complementary to the target analyte. Ligation can be performed enzymatically or chemically, as described herein. For example, the first and second probes are hybridized to the first and second target regions of the analyte, and the probes are subjected to a nucleic acid reaction to ligate them together. For example, the probes may be subjected to an enzymatic ligation reaction using a ligase (e.g., T4 RNA ligase (Rnl2), a *Chlorella* virus DNA ligase, or a T4 DNA ligase). Sec, e.g., Zhang L., et al.; Archacal RNA ligase from thermoccocus kodakarensis for template dependent ligation RNA Biol. 2017; 14(1): 36-44 for a description of KOD ligase. A skilled artisan will understand that various reagents, buffers, cofactors, etc. may be included in a ligation reaction depending on the ligase being used.

In some embodiments, the first probe and the second probes are on a contiguous nucleic acid sequence. In some embodiments, the first probe is on the 3' end of the contiguous nucleic acid sequence. In some embodiments, the first probe is on the 5' end of the contiguous nucleic acid sequence. In some embodiments, the second probe is on the 3' end of the contiguous nucleic acid sequence. In some embodiments, the second probe is on the 5' end of the contiguous nucleic acid sequence.

In some embodiments, the method further includes hybridizing a third probe to the first probe and the second probe such that the first probe and the second probe abut each other. In some embodiments, the third probe comprises a sequence that is at least 80%, at least 85%, at least 90%, at least 95%, at least 96%, at least 97%, at least 98%, or at least 99% complementary to a portion of the first probe that hybridizes to the third probe. In some embodiments, the third probe comprises a sequence that is 100% complementary to a portion of the first probe that hybridizes to the third probe. In some embodiments, the third probe comprises a sequence that is at least 80%, at least 85%, at least 90%, at least 95%, at least 96%, at least 97%, at least 98%, or at least 99% complementary to a portion of the second probe that hybridizes to the third probe. In some embodiments, the third probe comprises a sequence that is 100% complementary to a portion of the second probe that hybridizes to the third probe.

In some embodiments, a method for identifying a location of an analyte in a biological sample exposed to different incubation conditions includes (a) contacting the biological sample with a substrate, wherein the substrate comprises a plurality of capture probes, wherein a capture probe of the plurality of capture probes comprises a capture domain; (b) contacting the biological sample with a first probe and a second probe, wherein the first probe and the second probe are substantially complementary to adjacent sequences of the analyte, and wherein the second probe comprises a capture probe-binding domain that is capable of binding to a capture domain of the capture probe; (c) hybridizing the first probe and the second probe to adjacent sequences of the analyte; (d) coupling (e.g., ligating) the first probe and the second probe, thereby creating a connected probe (e.g., a connected probe (e.g., a ligation product)) that is substantially complementary to the analyte; (c) releasing the connected probe (e.g., a ligation product) from the analyte; (f) hybridizing the capture probe-binding domain of the connected probe (e.g., a ligation product) to the hybridization domain of the capture probe; (g) hybridizing a padlock oligonucleotide to the connected probe (e.g., a ligation product) bound to the capture domain (e.g., such that the padlock oligonucleotide is circularized), wherein the padlock oligonucleotide comprises: (i) a first sequence that is substantially complementary to a first portion of the connected probe (e.g., a ligation product), (ii) a backbone sequence, and (iii) a second sequence that is substantially complementary to a second portion of the connected probe (e.g., a ligation product); and (i) ligating and amplifying the circularized padlock oligonucleotide (e.g., using rolling circle amplification using the circularized padlock oligonucleotide as a template), thereby creating an amplified circularized padlock oligonucleotide, and using the amplified circularized padlock oligonucleotide to identify the location of the analyte in the biological sample.

In some embodiments, the method further includes amplifying the connected probe (e.g., a ligation product) prior to the releasing step. In some embodiments, the entire connected probe (e.g., a ligation product) is amplified. In some embodiments, only part of the connected probe (e.g., a ligation product) is amplified. In some embodiments, amplification is isothermal. In some embodiments, amplification is not isothermal. Amplification can be performed using any of the methods described herein such as, but not limited to, a strand-displacement amplification reaction, a rolling circle amplification reaction, a ligase chain reaction, a transcription-mediated amplification reaction, an isothermal amplification reaction, and/or a 10 loop-mediated amplification reaction. In some embodiments, amplifying the connected probe (e.g., a ligation product) creates an amplified connected probe (e.g., a ligation product) that includes (i) all or part of sequence of the connected probe (e.g., a ligation product) specifically bound to the capture domain, or a complement thereof, and (ii) the spatial barcode, or a complement thereof.

In some embodiments, the method further includes determining (i) all or a part of the sequence of the connected probe (e.g., a ligation product), or a complement thereof, and (ii) the spatial barcode, or a complement thereof. In some embodiments, the method further includes using the determined sequence of (i) and (ii) to determine the location and/or abundance of the analyte in the biological sample.

In some embodiments, after coupling (e.g., ligation) of the first and second probes to create a ligation product, the connected probe (e.g., a ligation product) is released from the analyte. To release the connected probe (e.g., a ligation product), an endoribonuclease (e.g., RNase A, RNase C, RNase H, or RNase I) is used. An endoribonuclease such as RNase H specifically cleaves RNA in RNA:DNA hybrids. In some embodiments, the connected probe (e.g., a ligation product) is released enzymatically. In some embodiments, an endoribonuclease is used to release the probe from the analyte. In some embodiments, the endoribonuclease is one or more of RNase H. In some embodiments, the RNase H is RNase H1 or RNase H2.

In some embodiments, the releasing of the connected probe (e.g., a ligation product) includes contacting the biological sample with a reagent medium comprising a permeabilization agent and an agent for releasing the connected probe (e.g., a ligation product), thereby permeabilizing the biological sample and releasing the connected probe (e.g., a ligation product) from the analyte. In some embodiments, the agent for releasing the connected probe (e.g., a ligation product) comprises a nuclease. In some embodiments, the nuclease is an endonuclease. In some embodiments, the nuclease is an exonuclease. In some embodiments, the nuclease includes an RNase. In some embodiments, the RNase is selected from RNase A, RNase C, RNase H, or RNase I.

In some embodiments, the reagent medium further comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v).

In some embodiments, the reagent medium further includes a wetting agent.

In some instances, after creation of the connected probe (e.g., a ligation product), the methods disclosed herein include simultaneous treatment of the biological sample with a permeabilization agent such as proteinase K (to permeabilize the biological sample) and a releasing agent such as an endonuclease such as RNase H (to release the connected probe (e.g., a ligation product) from the analyte). In some instances, the permeabilization step and releasing step occur at the same time. In some instances, the permeabilization step occurs before the releasing step. In some embodiments, the permeabilization agent comprises a protease. In some embodiments, the protease is selected from trypsin, pepsin, elastase, or Proteinase K. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

In some embodiments, the reagent medium further includes a detergent. In some embodiments, the detergent is selected from sodium dodecyl sulfate (SDS), sarkosyl, saponin, Triton X-100™, or Tween-20™. In some embodiments, the reagent medium includes less than 5 w/v % of a detergent selected from sodium dodecyl sulfate (SDS) and sarkosyl. In some embodiments, the reagent medium includes as least 5% w/v % of a detergent selected from SDS and sarkosyl. In some embodiments, the reagent medium does not include SDS or sarkosyl.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about 35 minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, about 10 to about 45 minutes, about 10 to about 40 minutes, about 10 to about 35 minutes, about 10 to about 30 minutes, about 10 to about 25 minutes, about 10 to about 20 minutes, about 10 to about 15 minutes, about 15 to about 60 minutes, about 15 to about 55 minutes, about 15 to about 50 minutes, about 15 to about 45 minutes, about 15 to about 40 minutes, about 15 to about 35 minutes, about 15 to about 30 minutes, about 15 to about 25 minutes, about 15 to about 20 minutes, about 20 to about 60 minutes, about 20 to about 55 minutes, about 20 to about 50 minutes, about 20 to about 45 minutes, about 20 to about 40 minutes, about 20 to about 35 minutes, about 20 to about 30 minutes, about 20 to about 25 minutes, about 25 to about 60 minutes, about 25 to about 55 minutes, about 25 to about 50 minutes, about 25 to about 45 minutes, about 25 to about 40 minutes, about 25 to about 35 minutes, about 25 to about 30 minutes, about 30 to about 60 minutes, about 30 to about 55 minutes, about 30 to about 50 minutes, about 30 to about 45 minutes, about 30 to about 40 minutes, about 30 to about 35 minutes, about 35 to about 60 minutes, about 35 to about 55 minutes, about 35 to about 50 minutes, about 35 to about 45 minutes, about 35 to about 40 minutes, about 40 to about 60 minutes, about 40 to about 55 minutes, about 40 to about 50 minutes, about 40 to about 45 minutes, about 45 to about 60 minutes, about 45 to about 55 minutes, about 45 to about 50 minutes, about 50 to about 60 minutes, about 50 to about 55 minutes, or about 55 to about 60 minutes). In some embodiments, the biological sample and the array are contacted with the reagent medium for about 30 minutes.

In some embodiments, the connected probe (e.g., a ligation product) includes a capture probe binding domain, which can hybridize to a capture probe (e.g., a capture probe immobilized, directly or indirectly, on a substrate). In some embodiments, the capture probe includes a spatial barcode and the capture domain. In some embodiments, the capture probe binding domain of the connected probe (e.g., a ligation product) specifically binds to the capture domain of the capture probe.

In some embodiments, methods provided herein include mounting a biological sample on a first substrate, then aligning the first substrate with a second substrate including an array, such that at least a portion of the biological sample is aligned with at least a portion of the array, wherein the array includes a plurality of capture probes. After hybridization of the connected probe (e.g., a ligation product) to the capture probe, downstream methods (e.g., analyte capture agent addition to a biological sample) as disclosed herein can be performed.

In some embodiments, at least 50% of connected probes (e.g., a ligation products) released from the portion of the biological sample aligned with the portion of the array are captured by capture probes of the portion of the array. In some embodiments, at least 50%, at least 55%, at least 60%, at least 65%, at least 70%, at least 75%, at least 85%, at least 90%, at least 95%, at least 96%, at least 97%, at least 98%, at least 99%, or 100% of connected probe (e.g., a ligation products) are detected in spots directly under the biological sample.

In some embodiments, the capture probe includes a poly (T) sequence. In some embodiments, capture probe includes a sequence specific to the analyte. In some embodiments, the capture probe includes a functional domain. In some embodiments, the capture probe further includes one or more functional domains, a unique molecular identifier (UMI), a cleavage domain, and combinations thereof. In some embodiments, the capture probe binding domain includes a poly(A) sequence. In some embodiments, the capture probe binding domain includes a sequence complementary to a capture domain of a capture probe that detects a target analyte of interest. In some embodiments, the analyte is RNA. In some embodiments, the analyte is mRNA.

In some embodiments, the connected probe (e.g., a ligation product) (e.g., the analyte derived molecule) includes a capture probe binding domain, which can hybridize to a capture probe (e.g., a capture probe immobilized, directly or indirectly, on a substrate). Methods provided herein include contacting a biological sample with a substrate, wherein the capture probe is affixed to the substrate (e.g., immobilized to the substrate, directly or indirectly). After hybridization of the connected probe (e.g., a ligation product) to the capture probe, downstream methods as disclosed herein (e.g., sequencing, in situ analysis such as RCA) can be performed.

In some embodiments, the method further includes analyzing a different analyte in the biological sample. In some embodiments, the analysis of the different analyte includes (a) further contacting the biological sample with a plurality of analyte capture agents, wherein an analyte capture agent of the plurality of analyte capture agents includes an analyte binding moiety and a capture agent barcode domain, wherein the analyte binding moiety specifically binds to the different analyte, and wherein the capture agent barcode domain includes an analyte binding moiety barcode and an capture handle sequence that is complementary to a capture domain of a capture probe; and (b) hybridizing the analyte capture sequence to the capture domain.

Provided herein are methods that allow for analysis of protein and RNA analytes. Briefly, a fixed tissue sample mounted on a first substrate (e.g., a slide-mounted tissue sample) is decrosslinked. In some embodiments, decrosslinking crosslinks (e.g., formaldehyde-induced crosslinks) can be performed in the presence of a buffer. In some embodiments, the buffer is Tris-EDTA (TE) buffer (e.g., TE buffer for FFPE biological samples). In some embodiments, the buffer is citrate buffer (e.g., citrate buffer for FFPE biological samples). In some embodiments, the buffer is Tris-HCl buffer (e.g., Tris-HCl buffer for PFA fixed biological samples). In some embodiments, the buffer (e.g., TE buffer, Tris-HCl buffer) has a pH of about 5.0 to about 10.0 and a temperature between about 60 °C to about 100 °C.

In some instances, the methods are followed by hybridization of probe pairs to nucleic acid analyte analytes. Then, a first and second probe of a probe pair is connected, e.g., ligated. The sample is optionally washed (e.g., with a buffer), prior to incubation with an analyte capture agent (e.g., an antibody) that specifically binds a different analyte, e.g., a protein analyte. The analyte capture agent comprises a capture agent barcode domain. In some embodiments, the analyte capture agent is an antibody with an oligonucleotide tag, the oligonucleotide tag comprising a capture agent barcode domain. In some embodiments, the connected probes (e.g., the ligation products) and antibody oligonucleotide tags are released from the tissue under sandwich conditions as described herein. For the sandwich conditions, the tissue-mounted slide can be aligned with an array and permeabilized with a reagent medium in the sandwich configuration as described herein. In some embodiments, the reagent medium comprises RNase and a permeabilization agent (e.g., Proteinase K). Permeabilization releases the connected probe (e.g., a ligation product) and capture agent barcode domain, for capture onto a second substrate comprising an array with a plurality of capture probes. After capture of the connected probe and capture agent barcode domain, the tissue slide can be removed (e.g., the sandwich can be “opened” or “broken”).

In some embodiments, following opening of the sandwich, the capture probes can be extended, sequencing libraries can be prepared and sequenced, and the results can be analyzed computationally.

In some embodiments, the method further includes determining (i) all or part of the sequence of the capture agent barcode domain; and (ii) the spatial barcode, or a complement thereof. In some embodiments, the method further includes using the determined sequence of (i), and (ii) to analyze the different analyte in the biological sample. In some embodiments, the releasing step further releases the capture agent barcode domain from the different analyte. In some embodiments, the different analyte is a protein analyte. In some embodiments, the protein analyte is an extracellular protein. In some embodiments, the protein analyte is an intracellular protein.

(iv) Sandwich Processes

In some embodiments, one or more analytes from the biological sample are released from the biological sample and migrate to a substrate comprising an array of capture probes for attachment to the capture probes of the array. In some embodiments, the release and migration of the analytes to the substrate comprising the array of capture probes occurs in a manner that preserves the original spatial context of the analytes in the biological sample. In some embodiments, the biological sample is mounted on a first substrate and the substrate comprising the array of capture probes is a second substrate. In some embodiments, the alignment of the first substrate and the second substrate is facilitated by a sandwiching process. Accordingly, described herein are methods, compositions, devices, and systems for sandwiching together the first substrate as described herein with a second substrate having an array with capture probes.

In some embodiments, the sandwiching process may be facilitated by a device, sample holder, sample handling apparatus, or system described in, e.g., US. Patent Application Pub. No. 20210189475, PCT/US2021/036788, or PCT/US2021/050931.

In some embodiments, the first and second substrates are placed in a substrate holder (e.g., an array alignment device) configured to align the biological sample and the array. In some embodiments, the device comprises a sample holder. In some embodiments, the sample holder includes a first member and a second member that receive a first substrate and a second substrate, respectively. The device can include an alignment mechanism that is connected to at least one of the members and aligns the first and second members. Thus, the devices of the disclosure can advantageously align the first substrate and the second substrate and any samples, barcoded probes, or permeabilization reagents that may be on the surface of the first and second substrates.

In some embodiments, the sandwiching process comprises: mounting the first substrate on a first member of a support device, the first member configured to retain the first substrate; mounting the second substrate on a second member of the support device, the second member configured to retain the second substrate, applying a reagent medium to the first substrate and/or the second substrate, the reagent medium comprising e.g., a monovalent or divalent salt, ethylene carbonate, glycerol, and/or a permeabilization agent, operating an alignment mechanism of the support device to move the first member and/or the second member such that a portion of the biological sample is aligned (e.g., vertically aligned) with a portion of the array of capture probes and within a threshold distance of the array of capture probes, and such that the portion of the biological sample and the capture probe contact the reagent medium, wherein the permeabilization agent releases the analyte from the biological sample.

In some embodiments of a sample holder, the sample holder can include a first member including a first retaining mechanism configured to retain a first substrate comprising a sample. The first retaining mechanism can be configured to retain the first substrate disposed in a first plane. The sample holder can further include a second member including a second retaining mechanism configured to retain a second substrate disposed in a second plane. The sample holder can further includes an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The alignment mechanism may be configured to move the second member along the axis orthogonal to the second plane and/or move the first member along an axis orthogonal to the first plane.

In some embodiments, the alignment mechanism includes a linear actuator. In some embodiments, the alignment mechanism includes one or more of a moving plate, a bushing, a shoulder screw, a motor bracket, and a linear actuator. The moving plate may be coupled to the first member or the second member. The alignment mechanism may, in some cases, include a first moving plate coupled to the first member and a second moving plate coupled to the second member. In some embodiments, the linear actuator is configured to move the second member along an axis orthogonal to the plane of the first member and/or the second member. For example, the moving plate may be coupled to the second member and adjust the separation distance along a z axis (e.g., orthogonal to the second substrate) by moving the moving plate up in a superior direction toward the first substrate. In some embodiments, the linear actuator is configured to move the first member along an axis orthogonal to the plane of the first member and/or the second member. The movement of the moving plate may be accomplished by the linear actuator configured to move the first member and/or the second member at a velocity. The velocity may be controlled by a controller communicatively coupled to the linear actuator. In some embodiments, the linear actuator is configured to move the first member, the second member, or both the first member and the second member at a velocity of at least 0.1 mm/sec (e.g., at least 0.1 mm/sec to 2 mm/sec). In some aspects, the velocity may be selected to reduce or minimize bubble generation or trapping within the reagent medium. In some embodiments, the linear actuator is configured to move the first member, the second member, or both the first member and the second member with an amount of force of at least 0.1 lbs (e.g., between 0.1-4.0 pounds of force).

In some aspects, the velocity of the moving plate (e.g., closing the sandwich) may affect bubble generation or trapping within the reagent medium. It may be advantageous to minimize bubble generation or trapping within the reagent medium during the "sandwiching" process, as bubbles can interfere with the migration of analytes through the reagent medium to the array. In some embodiments, the closing speed is selected to minimize bubble generation or trapping within the reagent medium. In some embodiments, the closing speed is selected to reduce the time it takes the flow front of the reagent medium from an initial point of contact with the first and second substrate to sweep across the sandwich area (also referred to herein as "closing time"). In some embodiments, the closing speed is selected to reduce the closing time to less than about 1100 milliseconds (ms). In some embodiments, the closing speed is selected to reduce the closing time to less than about 1000 ms. In some embodiments, the closing speed is selected to reduce the closing time to less than about 900 ms. In some embodiments, the closing speed is selected to reduce the closing time to less than about 750 ms. In some embodiments, the closing speed is selected to reduce the closing time to less than about 600 ms. In some embodiments, the closing speed is selected to reduce the closing time to about 550 ms or less. In some embodiments, the closing speed is selected to reduce the closing time to about 370 ms or less. In some embodiments, the closing speed is selected to reduce the closing time to about 200 ms or less. In some embodiments, the closing speed is selected to reduce the closing time to about 150 ms or less.

Further details on support devices, sample holders, sample handling apparatuses, or systems for implementing a sandwiching process are described in, e.g., PCT Publ. No. WO 2021/0189475 and PCT/US2021/050931, each of which are incorporated by reference in their entirety.

Analytes within a biological sample may be released through disruption (e.g., permeabilization, digestion, etc.) of the biological sample or may be released without disruption. Various methods of permeabilizing (e.g., any of the permeabilization reagents and/or conditions described herein) a biological sample are described herein, including for example including the use of various detergents, buffers, proteases, and/or nucleases for different periods of time and at various temperatures. Additionally, various methods of delivering fluids (e.g., a buffer, a permeabilization solution) to a biological sample are described herein including the use of a substrate holder (e.g., for sandwich assembly, sandwich configuration, as described herein)

Provided herein are methods for delivering a fluid to a biological sample disposed on an area of a first substrate and an array disposed on a second substrate.

In some embodiments, the sandwich configuration described herein between a first substrate comprising a biological sample and a second substrate comprising a spatially barcoded array may include a reagent medium comprising a monovalent or divalent salt (e.g., NaCl), ethylene carbonate, and/or glycerol to fill a gap. It may be desirable that the reagent medium be free from air bubbles between the slides to facilitate transfer of target molecules with spatial information. Additionally, air bubbles present between the slides may obscure at least a portion of an image capture of a desired region of interest. Accordingly, it may be desirable to ensure or encourage suppression and/or elimination of air bubbles between the two substrates during a permeabilization step.

In some aspects, it may be possible to reduce or eliminate bubble formation between the slides using a variety of filling methods and/or closing methods.

Workflows described herein may include contacting a drop of the reagent medium (e.g., liquid reagent medium comprising NaCl, ethylene carbonate, and/or glycerol) disposed on a first substrate or a second substrate with at least a portion of the second substrate or first substrate, respectively. In some embodiments, the contacting comprises bringing the two substrates into proximity such that the sample on the first substrate is aligned with the barcode array of capture probes on the second substrate.

In some embodiments, the drop includes permeabilization reagents (e.g., any of the permeabilization reagents described herein). In some embodiments, the rate of permeabilization of the biological sample is modulated by delivering the permeabilization reagents (e.g., a fluid containing permeabilization reagents) at various temperatures.

In the example sandwich maker workflows described herein, the reagent medium comprising NaCl, ethylene carbonate, and/or glycerol may fill a gap between a first substrate and a second substrate to warrant or enable transfer of target molecules with spatial information. Described herein are examples of filling methods that may suppress bubble formation and suppress undesirable flow of transcripts and/or target molecules or analytes. Robust fluidics in the sandwich making described herein may preserve spatial information by reducing or preventing deflection of molecules as they move from the tissue slide to the capture slide.

Further details on angled closure workflows, and devices and systems for implementing an angled closure workflow, are described in PCT/US2021/036788 and PCT/US2021/050931, which are hereby incorporated by reference in their entirety. Additional configurations for reducing or eliminating bubble formation, and/or for reducing unwanted fluid flow, are described in PCT/US2021/036788, which is hereby incorporated by reference in its entirety.

In some embodiments, the reagent medium comprising NaCl, ethylene carbonate, and/or glycerol also comprises a permeabilization agent. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). Exemplary permeabilization reagents are described in in PCT Patent Application Publication No. WO 2020/123320, which is incorporated by reference in its entirety.

In some embodiments, the reagent medium comprising NaCl, ethylene carbonate, and/or glycerol also comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. Exemplary lysis reagents are described in PCT Patent Application Publication No. WO 2020/123320, which is incorporated by reference in its entirety.

In some embodiments, the reagent medium comprising NaCl, ethylene carbonate, and/or glycerol also comprises a protease. Exemplary proteases include, e.g., pepsin, trypsin, pepsin, elastase, and proteinase K. Exemplary proteases are described in PCT Patent Application Publication No. WO 2020/123320, which is incorporated by reference in its entirety.

In some embodiments, the reagent medium comprising NaCl, ethylene carbonate, and/or glycerol also comprises a detergent. Exemplary detergents include sodium dodecyl sulfate (SDS), sarkosyl, saponin, Triton X-100™, and Tween-20™. Exemplary detergents are described in PCT Patent Application Publication No. WO 2020/123320, which is incorporated by reference in its entirety.

In some embodiments, the reagent medium comprising NaCl, ethylene carbonate, and/or glycerol also comprises a nuclease. In some embodiments, the nuclease comprises am RNase. In some embodiments, the RNase is selected from RNase A, RNase C, RNase H, and RNase I. In some embodiments, the reagent medium comprises one or more of sodium dodecyl sulfate (SDS), proteinase K, pepsin, N-lauroylsarcosine, RNAse, and a sodium salt thereof.

The sample holder is compatible with a variety of different schemes for contacting the aligned portions of the biological sample and array with the reagent medium to promote analyte capture. In some embodiments, the reagent medium is deposited directly on the second substrate (e.g., forming a reagent medium that includes the permeabilization reagent and the feature array), and/or directly on the first substrate. In some embodiments, the reagent medium is deposited on the first and/or second substrate, and then the first and second substrates aligned in the sandwich configuration such that the reagent medium contacts the aligned portions of the biological sample and array. In some embodiments, the reagent medium is introduced into the gap while the first and second substrates are aligned in the sandwich configuration.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid). In some instances, the substrate that includes the sample (e.g., a histological tissue section) is hydrated. The sample can be hydrated by contacting the sample with a reagent medium, e.g., a buffer that does not include a permeabilization reagent. In some embodiments, the hydration is performed while the first and second substrates are aligned in a sandwich configuration.

In some instances, the aligned portions of the biological sample and the array are in contact with the reagent medium comprising NaCl, ethylene carbonate, and/or glycerol also for about 1 minute. In some instances, the aligned portions of the biological sample and the array are in contact with the reagent medium comprising NaCl, ethylene carbonate, and/or glycerol also for about 5 minutes. In some instances, the aligned portions of the biological sample and the array are in contact with the reagent medium comprising NaCl, ethylene carbonate, and/or glycerol also in the gap for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium comprising NaCl, ethylene carbonate, and/or glycerol also for about 1-60 minutes. In some instances, the aligned portions of the biological sample and the array are in contact with the reagent medium comprising NaCl, ethylene carbonate, and/or glycerol also for about 30 minutes.

In some embodiments, following initial contact between sample and a permeabilization agent, the permeabilization agent can be removed from contact with sample (e.g., by opening sample holder) before complete permeabilization of sample. For example, in some embodiments, only a portion of sample is permeabilized, and only a portion of the analytes in sample may be captured by feature array. In some instances, the reduced amount of analyte captured and available for detection can be offset by the reduction in lateral diffusion that results from incomplete permeabilization of sample. In general, the spatial resolution of the assay is determined by the extent of analyte diffusion in the transverse direction (i.e., orthogonal to the normal direction to the surface of sample). The larger the distance between the sample on the first substrate and the feature array on the second substrate, the greater the extent of diffusion in the transverse direction, and the concomitant loss of resolution. Analytes liberated from a portion of the sample closest to the feature array have a shorter diffusion path, and therefore do not diffuse as far laterally as analytes from portions of the sample farthest from the feature array. As a result, in some instances, incomplete permeabilization of the sample (by reducing the contact interval between the permeabilization agent and the sample) can be used to maintain adequate spatial resolution in the assay.

In some instances, the device is configured to control a temperature of the first and second substrates. In some embodiments, the temperature of the first and second members is lowered to a first temperature that is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower). In some embodiments, the device includes a temperature control system (e.g., heating and cooling conducting coils) to control the temperature of the sample holder. Alternatively, in other embodiments, the temperature of the sample holder is controlled externally (e.g., via refrigeration or a hotplate). In a first step, the second member, set to or at the first temperature, contacts the first substrate, and the first member, set to or at the first temperature, contacts the second substrate, thereby lowering the temperature of the first substrate and the second substrate to a second temperature. In some embodiments, the second temperature is equivalent to the first temperature. In some embodiments, the first temperature is lower than room temperature (e.g., 25 degrees Celsius). In some embodiments, the second temperature ranges from about −10 degrees Celsius to about 4 degrees Celsius. In some embodiments, the second temperature is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower).

In an exemplary embodiment, the second substrate is contacted with the permeabilization reagent. In some embodiments, the permeabilization reagent is dried. In some embodiments, the permeabilization reagent is a gel or a liquid. Also in the exemplary embodiment, the biological sample is contacted with buffer. Both the first and second substrates are placed at lower temperature to slow down diffusion and permeabilization efficiency. Alternatively, in some embodiments, the sample can be contacted directly with a liquid permeabilization reagent without inducing an unwanted initiation of permeabilization due to the substrates being at the second temperature. In some embodiments, the low temperature slows down or prevents the initiation of permeabilization. In a second step, keeping the sample holder and substrates at a cold temperature (e.g., at the first or second temperatures) continues to slow down or prevent the permeabilization of the sample. In a third step, the sample holder (and consequently the first and second substrates) is heated up to initiate permeabilization. In some embodiments, the sample holder is heated up to a third temperature. In some embodiments, the third temperature is above room temperature (e.g., 25 degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of the sample diffuse to the surface of the second substrate and are captured on the array (e.g., barcoded probes) of the second substrate. In a fourth step, the first substrate and the second substrate are separated (e.g., pulled apart) and temperature control is stopped.

In some embodiments, where either the first substrate or substrate second (or both) includes wells, a permeabilization solution can be introduced into some or all of the wells, and then the sample and the feature array can be contacted by closing the sample holder to permeabilize the sample. In certain embodiments, a permeabilization solution can be soaked into a hydrogel film that is applied directly to the sample, and/or soaked into features (e.g., beads) of the array. When the first and second substrates are aligned in the sandwich configuration, the permeabilization solution promotes migration of analytes from the sample to the array.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from the sample can be spatially adjusted.

In some instances, migration of the analyte from the biological sample to the second substrate is passive (e.g., via diffusion). Alternatively, in certain embodiments, migration of the analyte from the biological sample is performed actively (e.g., electrophoretic, by applying an electric field to promote migration). In some instances, first and second substrates can include a conductive epoxy. Electrical wires from a power supply can connect to the conductive epoxy, thereby allowing a user to apply a current and generate an electric field between the first and second substrates. In some embodiments, electrophoretic migration results in higher analyte capture efficiency and better spatial fidelity of captured analytes (e.g., on a feature array) than random diffusion onto matched substrates without the application of an electric field (e.g., via manual alignment of the two substrates). Exemplary methods of electrophoretic migration are described in WO 2020/176788, including at FIGS. 13-15, 24A-24B, and 25A-25C, which is hereby incorporated by reference in its entirety.

Loss of spatial resolution can occur when analytes migrate from the sample to the feature array and a component of diffusive migration occurs in the transverse (e.g., lateral) direction, approximately parallel to the surface of the first substrate on which the sample is mounted. To address this loss of resolution, in some embodiments, a permeabilization agent deposited on or infused into a material with anisotropic diffusion can be applied to the sample or to the feature array. The first and second substrates are aligned by the sample holder and brought into contact. A permeabilization layer that includes a permeabilization solution infused into an anisotropic material is positioned on the second substrate.

In some embodiments, the feature array can be constructed atop a hydrogel layer infused with a permeabilization agent. The hydrogel layer can be mounted on the second substrate, or alternatively, the hydrogel layer itself may function as the second substrate. When the first and second substrates are aligned, the permeabilization agent diffuses out of the hydrogel layer and through or around the feature array to reach the sample. Analytes from the sample migrate to the feature array. Direct contact between the feature array and the sample helps to reduce lateral diffusion of the analytes, mitigating spatial resolution loss that would occur if the diffusive path of the analytes was longer.

Spatial analysis workflows can include a sandwiching process described herein. In some embodiments, the workflow includes provision of the first substrate comprising the biological sample. In some embodiments, the workflow includes, mounting the biological sample onto the first substrate. In some embodiments wherein the biological sample is a tissue sample, the workflow include sectioning of the tissue sample (e.g., cryostat sectioning). In some embodiments, the workflow includes a fixation step. In some instances, the fixation step can include fixation with methanol. In some instances, the fixation step includes formalin (e.g., 2% formalin).

In some embodiments, the biological sample on the first substrate is stained using any of the methods described herein. In some instances, the biological sample is imaged, capturing the stain pattern created during the stain step. In some instances, the biological sample then is destained prior to the sandwiching process.

In some instances, the methods include imaging the biological sample. In some instances, imaging occurs prior to sandwich assembly. In some instances, imaging occurs while the sandwich configuration is assembled. In some instances, imaging occurs during permeabilization of the biological sample. In some instances, image are captured using high resolution techniques (e.g., having 300 dots per square inch (dpi) or greater). For example, images can be captured using brightfield imaging (e.g., in the setting of hematoxylin or H&E stain), or using fluorescence microscopy to detect adhered labels. In some instances, high resolution images are captured temporally using e.g., confocal microscopy. In some instances, a low resolution image is captured. A low resolution image (e.g., images that are about 72 dpi and normally have an RGB color setting) can be captured at any point of the workflow, including but not limited to staining, destaining, permeabilization, sandwich assembly, and migration of the analytes. In some instances, a low resolution image is taken during permeabilization of the biological sample.

In some embodiments, the location of the one or more analytes in a biological sample are determined by immunofluorescence. In some embodiments, one or more detectable labels (e.g., fluorophore-labeled antibodies) bind to the one or more analytes that are captured (hybridized to) by a probe on the first slide and the location of the one or more analytes is determined by detecting the labels under suitable conditions. In some embodiments, one or more fluorophore-labeled antibodies are used to conjugate to a moiety that associates with a probe on the first slide or the analyte that is hybridized to the probe on the first slide. In some instances, the location(s) of the one or more analytes is determined by imaging the fluorophore-labeled antibodies when the fluorophores are excited by a light of a suitable wavelength. In some embodiments, the location of the one or more analytes in the biological sample is determined by correlating the immunofluorescence data to an image of the biological sample. In some instances, the tissue is imaged throughout the permeabilization step.

In some instances, the biological samples can be destained. In some instances, destaining occurs prior to permeabilization of the biological sample. By way of example only, H&E staining can be destained by washing the sample in HCl. In some instances, the hematoxylin of the H&E stain is destained by washing the sample in HCl. In some embodiments, destaining can include 1, 2, 3, or more washes in HCl. In some embodiments, destaining can include adding HCl to a downstream solution (e.g., permeabilization solution).

Between any of the methods disclosed herein, the methods can include a wash step (e.g., with SSC (e.g., 0.1×SSC)). Wash steps can be performed once or multiple times (e.g., 1×, 2×, 3×, between steps disclosed herein). In some instances, wash steps are performed for about 10 seconds, about 15 seconds, about 20 seconds, about 30 seconds, or about a minute. In some instances, three washes occur for 20 seconds each. In some instances, the wash step occurs before staining the sample, after destaining the sample, before permeabilization the sample, after permeabilization the sample, or any combination thereof.

In some instances, after the sandwiching process the first substrate and the second substrate are separated (e.g., such that they are no longer aligned in a sandwich configuration, also referred to herein as opening the sandwich). In some embodiments, subsequent analysis (e.g., cDNA synthesis, library preparation, and sequences) can be performed on the captured analytes after the first substrate and the second substrate are separated.

In some embodiments, the process of transferring the ligation product or methylated-adaptor-containing nucleic acid from the first substrate to the second substrate is referred to interchangeably herein as a “sandwich process,” “sandwiching process,” or “sandwiching”. The sandwich process is further described in PCT Patent Application Publication No. WO 2020/123320, PCT/US2021/036788, and PCT/US2021/050931, which are incorporated by reference in its entirety.

(v) Use of Multiplexed Sandwich Makers

This disclosure also provides methods, compositions, devices, and systems for using a single capture probe-containing to detect analytes from different biological samples (e.g., tissues) on different slides using serial sandwich processes. Thus, only one capture probe-containing array is necessary for the methods disclosed herein. In this way, as described herein, analytes from different samples or tissues can be captured serially and demultiplexed by sample-specific index sequences.

The methods include generating a connected probe (e.g., a ligation product) in multiple biological samples (i.e., a first sample, a second sample, a third sample, etc.). Generation of a connected probe (e.g., a ligation product) has been described above, and the same methods are used herein to generate a connected probe (e.g., a ligation product) from analytes that are either protein analytes or nucleic acid (e.g., mRNA) analytes. That is, in some instances, the multiplexed sandwich maker methods disclosed herein can be used to detect protein analytes. In other instances, the multiplexed sandwich maker methods disclosed herein can be used to detect nucleic acid (e.g., mRNA) analytes.

The methods, compositions, devices, and systems include utilizing an analyte capture agent in multiple biological samples (i.e., a first sample, a second sample, a third sample, etc.). Using analyte capture agents for spatial detection has been described above, and, the same methods are used herein to use an analyte capture agent to identify analytes in a biological sample. In some embodiments, the multiplexed sandwich maker methods disclosed herein can be used to detect protein analytes.

As discussed below, each connected probe (e.g., a ligation product) that is generated or analyte capture agent includes a sample index sequence, which is a nucleotide sequence that is associated with a particular sample of origin in the multiplex sandwich methods. After generation of each connected probe (e.g., a ligation product) or analyte capture agent, each sample is serially sandwiched to an array or slide having a plurality of capture probes that can detect and hybridize to a capture probe binding domain from the connected probe (e.g., a ligation product) or analyte capture agent. During the sandwiching process, the indexed connected probe or analyte capture agent actively or passively migrates from the sample to the array for capture by a capture probe. Then the sandwich is opened, and the next sample is sandwiched with the array. In some embodiments, the array is washed prior to sandwiching with the next sample. Additional samples or tissues (e.g., 2 or more) can then be sandwiched with the array or slide having a plurality of capture probes, wherein connected probes (e.g., ligation products) or analyte capture agents from the additional samples or tissues can be transferred to the array in a similar manner. Because each sample includes a unique sample index, the sample of origin for each connected probe (e.g., a ligation product) or analyte capture agent that is captured on the array can be identified. In addition, the location of the connected probe (e.g., a ligation product) can be identified. In some embodiments, the location of the analyte capture agent can be identified. In some instances, the location is identified using fiducial markers on the gene expression slide (i.e., array) so that location of the ligation probe on the array mirrors the location of the sample on the sample slide. Exemplary fiducial markers are described in PCT Patent Application Publication No. WO 2020/123320, which is incorporated by reference in its entirety.

Such methods, compositions, devices, and systems allow for detection of analytes in multiple samples using only one gene expression slide and can be performed on any slide sample described herein. For example, in some instances, the biological sample is a formalin-fixed, paraffin-embedded (FFPE) sample, a frozen sample, or a fresh sample. In some instances, the biological sample is contacted with one or more stains. In some instances, the one or more stains include hematoxylin and eosin. In some instances, cell markers are detected using methods known in the art (e.g., using one or more optical labels such as fluorescent labels, radioactive labels, chemiluminescent labels, calorimetric labels, or colorimetric labels. In some instances, the biological sample is imaged before generating a connected probe (e.g., a ligation product) and before transferring the connected probe (e.g., a ligation product) to the gene expression slide.

The multiplex sandwich methods, compositions, devices, and systems described herein allow for detection of different types of samples and different analytes. For example in some instances, the samples used in the multiplex sandwich methods are from different species. In some instances, the samples used in the multiplex sandwich methods are from the same species but different individuals in the same species. In some instances, the samples used in the multiplex sandwich methods are from the same individual organism. In some instances, the samples are from different tissues or cell types. In some instances, the samples are from the same tissues or cell types. In some instances, the samples are from the same subject taken at different time points (e.g., before and after treatment). It is appreciated that the samples can be from any source so long as ligated products having sample index sequences unique to each sample are generated.

Multiple samples can be used in the methods described herein. For example, in some instances, at least two samples are used. In some instances, more than two samples (e.g., at least 3, 4, 5, 6, 7, 8, 9, 10, or more) samples are used in the methods disclosed herein. It is appreciated that each sample can be from different sources (e.g., different species, different organisms). In some embodiments, from each sample, the same gene is detected and identified. In some embodiments, for each sample, different genes are detected and identified.

In order to differentiate one sample from another, probe for each sample in a multiplexed setting can include one or more unique sequences to identify the origin of the connected probe (e.g., a ligation product). In some instances, the unique sequence is a sample index sequence. In some instances, probes for each sample include one or more (e.g., at least 1, 2, 3, 4, 5, or more) unique sample index sequence to identify the origin of the connected probe (e.g., a ligation product).

In some instances, the sample index is about 5 nucleotides to about 50 nucleotides long (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides long. In some embodiments, the sample index is about 5-15 nucleotides long. In some embodiments, the sample index is about 10-12 nucleotides long. Both synthetic and/or naturally-occurring nucleotides can be used to generate a sample index sequence. It is appreciated that any sequence can be designed so long as it is unique among other sample index sequences and optionally that it can be distinguished from any sequence in the genome of the sample.

A sample index sequence can be located anywhere on the connected probe (e.g., a ligation product) so long as it does not affect (1) hybridization of the probes to the analyte, (2) ligation of the probes to generate the connected probe (e.g., a ligation product), and (3) hybridization of the capture probe binding domain to the capture probe on an array. For example, in some instances, the sample index sequence can be located on the first probe (e.g., the left hand probe). In some instances, the sample index is located on the flap of the first probe that does not hybridize to the analyte. In some instances, the sample index sequence can be located on the second probe (e.g., the right hand probe). In some instances, the sample index is located on the flap of the second probe that does not hybridize to the analyte.

(vi) Systems and Kits

Also disclosed herein are systems and kits used for any one of the methods disclosed herein. In some instances, the system or kit is used for analyzing an analyte in a biological sample. In some instances, the system or kit includes a support device configured to retain a first substrate and a second substrate, wherein the biological sample is placed on the first substrate, and wherein the second substrate comprises a plurality of capture probes, wherein a capture probe of the plurality of capture probes comprises: (i) a spatial barcode and (ii) a capture domain. In some instances, the system or kit includes a first probe and a second probe, wherein the first probe and the second probe each comprise a sequence that is substantially complementary to adjacent sequences of the analyte, wherein the second probe comprises a capture probe binding domain, and wherein the first probe and the second probe are capable of being ligated together to form a connected probe. In some instances, the system or kit includes a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and a capture handle sequence.

In some instances, the system or kit further includes a reagent medium comprising a monovalent salt or divalent salt. In some instances, the monovalent salt or divalent salt in the reagent medium is at a concentration of about 250 mM. In some instances, the monovalent salt or divalent salt in the reagent medium is at a concentration of about 500 mM. In some instances, the monovalent salt or divalent salt in the reagent medium is at a concentration between about 100 mM and 1000 mM (e.g., about 100, 200, 300, 400, 500, 600, 700, 800, 900, or 1000 mM). In some instances, the monovalent salt is sodium chloride. In some instances, the sodium chloride in the reagent medium is at a concentration of about 250 mM. In some instances, the sodium chloride in the reagent medium is at a concentration of about 500 mM. In some instances, the monovalent salt is potassium chloride. In some instances, the divalent salt is magnesium chloride. In some instances, the reagent medium comprises ethylene carbonate. In some instances, the ethylene carbonate in the reagent medium comprises about 2% of the reagent medium. In some instances, the reagent medium comprises glycerol. In some instances, the glycerol in the reagent medium comprises about 2.5% of the reagent medium.

In some instances, the amount of the plurality of analyte capture agents is about 0.1 μg to about 1.5 μg (about 0.1, 0.2, 0.3, 0.4, 0.5, 0.6, 0.7, 0.8, 0.9, 1.0, 1.1, 1.2, 1.3, 1.4. or 1.5 μg). In some instances, the amount of the plurality of analyte capture agents is about 0.6 μg to about 1.0 μg.

In some instances, the reagent medium also includes a permeabilization agent and optionally an agent for releasing the connected probe. In some instances, the system or kit includes instructions for performing any one of the methods described herein.

In some instances, the reagent medium may further include a detergent as disclosed herein, polyethylene glycol (PEG) as disclosed herein, or a nuclease as described herein.

In some instances, the permeabilization agent is pepsin or proteinase K. In some instances, the agent for releasing the connected probe is an RNAse, optionally wherein the RNAse is RNAse H.

In some instances, the system or kit further includes an alignment mechanism on the support device to align the first substrate and the second substrate. In some instances, the alignment mechanism comprises a linear actuator and the first substrate comprises a first member and the second substrate comprises a second member. The linear actuator can be configured to move the second member along an axis orthogonal to the plane or the first member and/or the second member. The linear actuator can be configured to move the first member along an axis orthogonal to the plane of the first member and/or the second member. The linear actuator can be configured to move the first member, the second member, or both the first member and the second member at a velocity of at least 0.1 mm/sec. Finally, in some instances, the linear actuator can be configured to move the first member, the second member, or both the first member and the second member with an amount of force of at least 0.1 lbs.

EXAMPLES

Example 1—Methods for Spatial Analysis of Protein and RNA with Sandwich Process In a non-limiting example, methods for spatial analysis of RNA and protein are performed. In brief, as outlined in FIG. 12, tissue sample sections on standard slides are deparaffinized if needed (e.g., FFPE samples), stained (e.g., H&E stained), and imaged. Next, the tissue samples are hematoxylin-destained e.g., 1× HCl solution washes for 15 minutes at 42 °C. The sections are then decrosslinked e.g., by incubating at 95 °C for 1 hour with a compatible buffer.

Individual probes (e.g., a first probe, a second probe) of probe pairs are hybridized to adjacent sequences of an analyte (e.g., an RNA molecule) in the tissue. The RTL probes are then ligated together, thereby creating a connected probe (e.g., a ligation product). The connected probe (e.g., a ligation product) includes a capture probe binding domain. The probes are designed to hybridize to part of the transcriptome (e.g., using 5,000 total probe pairs) or to hybridize to each transcript in the human transcriptome.

The sections are then incubated with either individual or a panel of oligo-tagged antibodies (e.g., totalseq B), followed by washing. The antibodies are tagged with oligonucleotides that have i) a sequence complementary to the capture domain of a capture probe on a slide having an array of capture probes, and ii) a barcode sequence that uniquely identifies the antibody. Then, the tissue-mounted slides are aligned with the slide having the array and the tissue is permeabilized in the sandwich configuration using a reagent medium as described herein (e.g., having a monovalent or divalent salt; ethylene carbonate and/or glycerol). The connected probes and antibody oligonucleotide tags are released from the tissue under such sandwich conditions, migrate, and hybridize to the capture probes. The reagent medium used for permeabilizing the tissue sample and releasing the connected probes and antibody oligonucleotide tags includes RNase and Proteinase K. The capture probes, connected probes, and/or antibody oligonucleotides are extended, sequencing libraries are prepared and sequenced, and the results are analyzed computationally.

Embodiments of the above methods were used in the following examples.

Example 2—Methods for Spatial Analysis of Protein and RNA with Sandwich Process in Reagent Medium with Variable Sodium Chloride Concentrations and with Ethylene Carbonate and Glycerol In the next experiment, the protocol was followed as described in Example 1. However, the reagent medium included variable sodium chloride (NaCl) concentrations. Samples were incubated with varying NaCl concentrations (e.g., 100 mM, 250 mM, and 500 mM) in a reagent medium also comprising 2% ethylene carbonate and 2.5% glycerol. As a negative control sample, a reagent medium lacking NaCl, lacking ethylene carbonate and lacking glycerol was used. This control reagent medium and sample was termed "SOP" throughout the experiment and is shown as such in the accompanying figures. In the present example, samples identified as "EXP" (i.e., experimental) included a reagent medium having 500 mM NaCl, 2% ethylene carbonate, and 2.5% glycerol.

Figure 14:
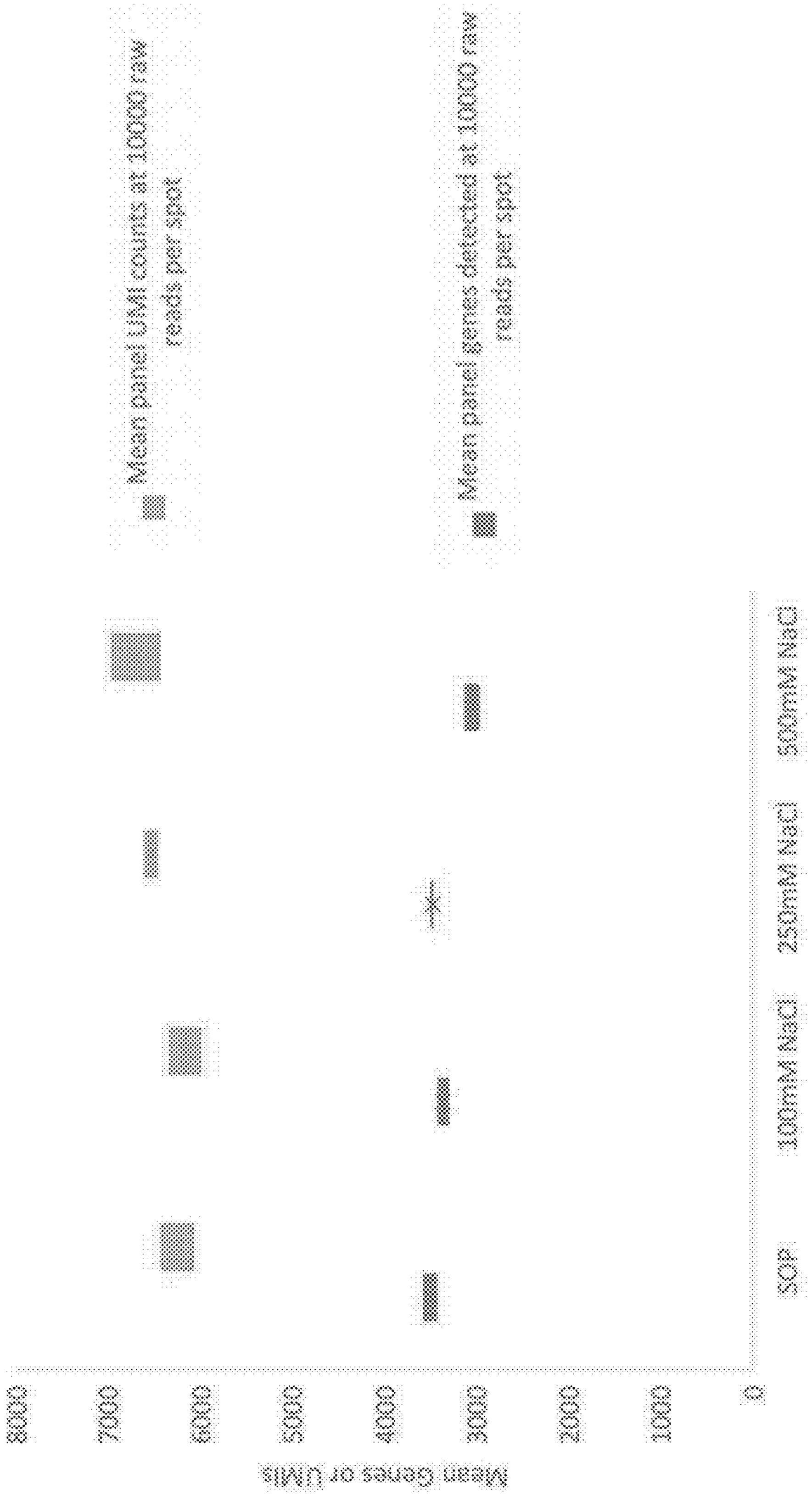
FIG. 14 shows the mean panel genes detected per spot as sodium chloride (NaCl) is increased.
Figure 15:
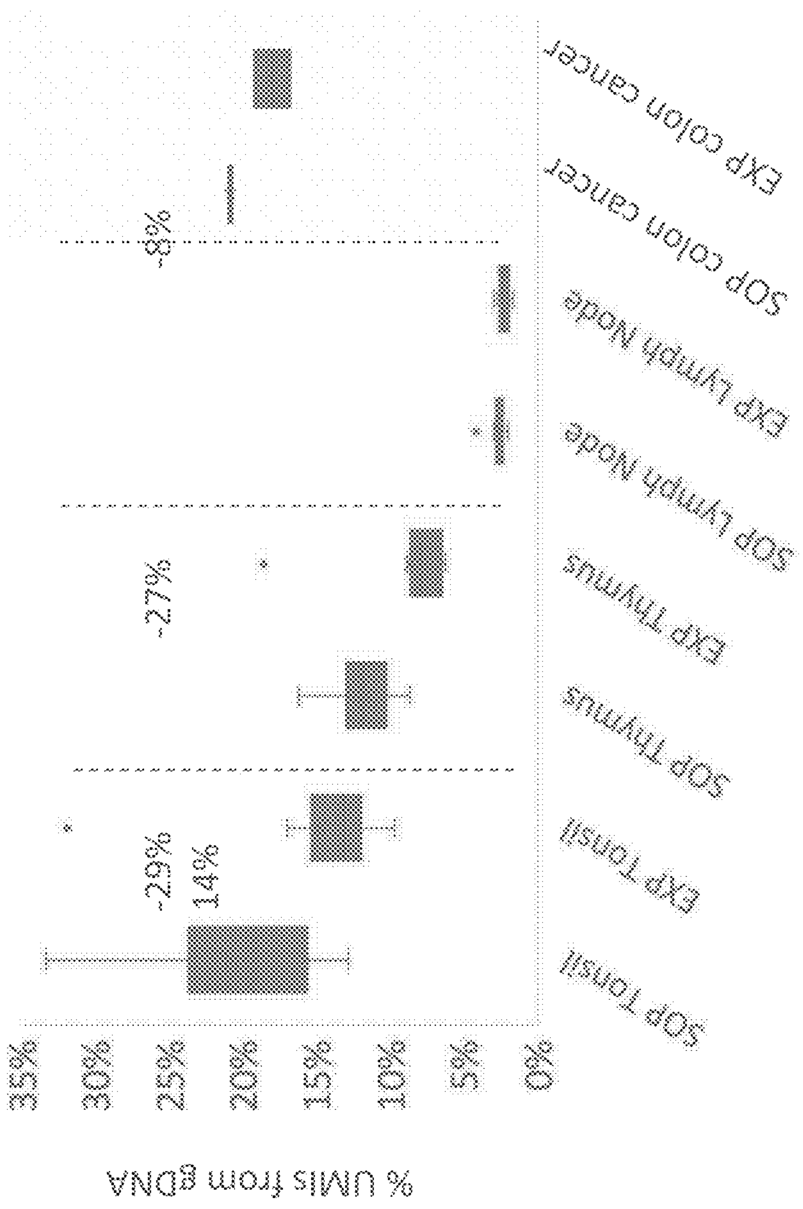
FIG. 15 shows the percent UMIs from genomic DNA (gDNA) as sodium chloride (NaCl) is increased. SOP: reagent medium comprising no NaCl, no ethylene carbonate, and no glycerol. EXP: reagent medium comprising 500 mM NaCl, 2% ethylene carbonate, and 2.5% glycerol.

As shown in FIG. 13, increases in NaCl led to a reduction of low UMIs while—at the same time—not affecting detection sensitivity (FIG. 14). Further, across four different tissue types (normal human tonsil, normal human thymus, normal human lymph node, and a human cancerous colon), there was a decrease in genomic DNA detection in samples treated with 500 mM NaCl compared to samples not treated with NaCl. See FIG. 15.

Figure 16:
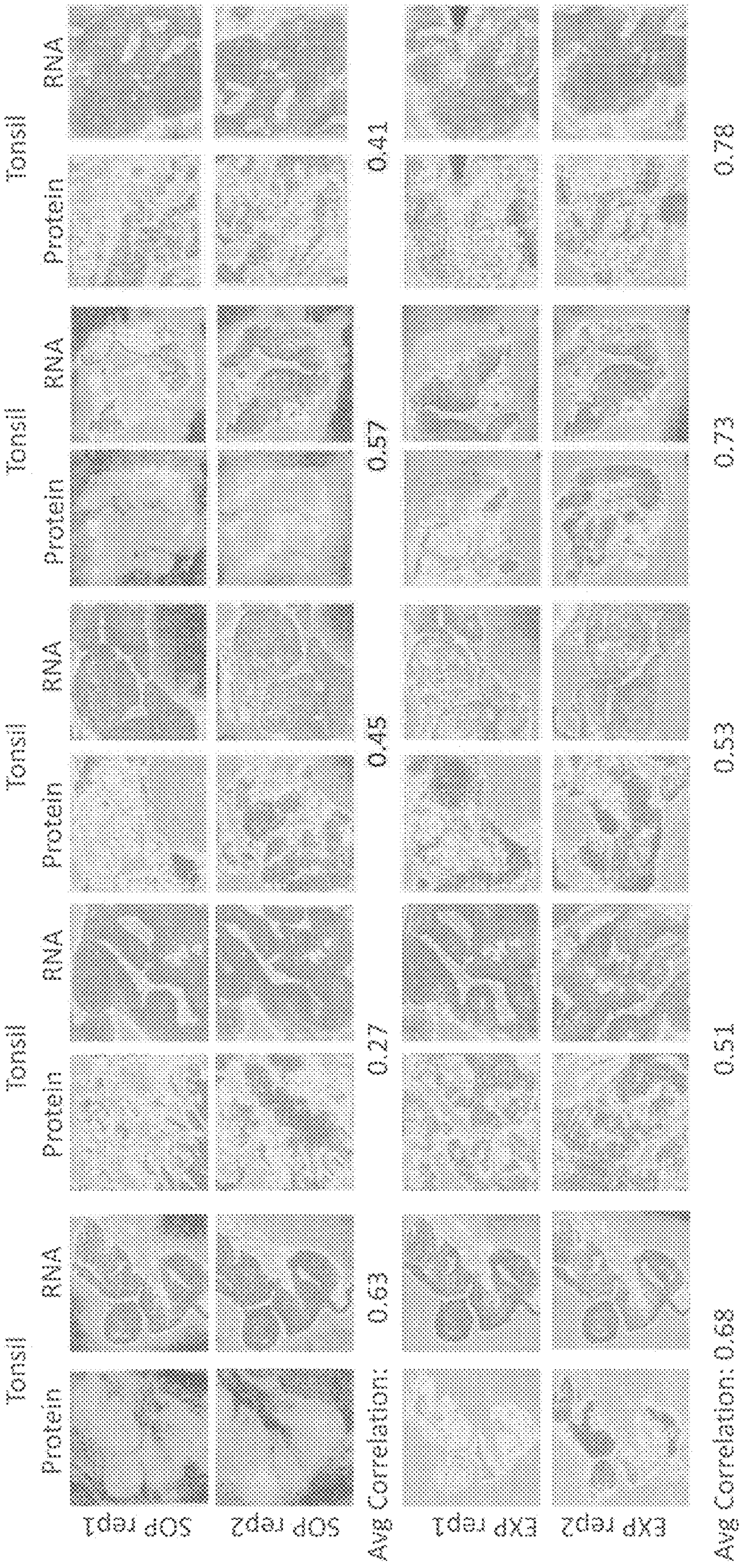
FIG. 16 shows representative images of protein and RNA detection in tonsil samples. Avg Correlation: ratio of RNA detected using RTL methods compared to protein detected using oligo-tagged antibodies.
Figure 17:
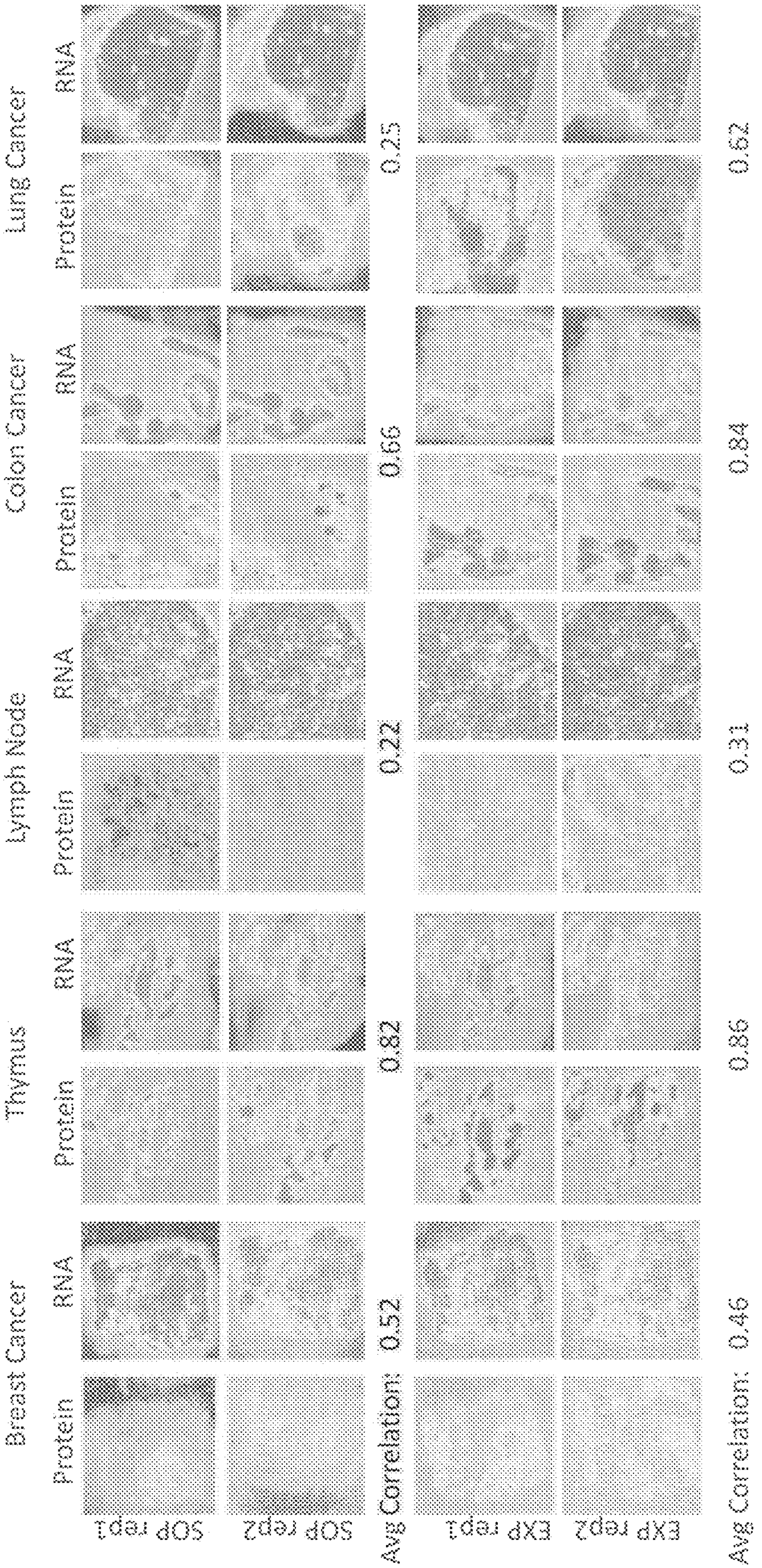
FIG. 17 shows representative images of protein and RNA detection in breast cancer, thymus, lymph node, colon cancer, and lung cancer samples.

Each of the experimental samples also showed more uniform UMI detection. For instance, compared to the negative control (SOP), samples treated with either NaCl, ethylene carbonate, and glycerol or only ethylene carbonate and glycerol (2% and 2.5%, respectively) resulted in increased uniformity of protein capture on the array using the oligo-tagged antibodies as shown by an increase in median UMIs per spot compared to negative control (SOP) samples. Further, while the combination of NaCl plus ethylene carbonate and glycerol improved uniformity of protein detection, NaCl appeared to be a major contributor. As concentration of NaCl increased to about 500 mM, so too did the correspondence between protein (using oligo-tagged antibodies) and RNA (via RTL) detection (e.g., using a metric of average % ΔCV, which is a ratio of RNA capture via RTL and antibody capture using oligo-tagged antibodies). Representative images for various tissues are shown in FIGS. 16 and 17, which show that total protein and RNA capture in five different tonsil samples (FIG. 16) and in breast cancer, thymus, lymph node, colon cancer, and lung cancer samples (FIG. 17). "Avg Correlation" refers to the ratio of RNA to protein. These data provide visual evidence that the methods disclosed herein (e.g., using 500 mM NaCl, and ethylene carbonate and glycerol (2% and 2.5%, respectively)) can be used to enhance detection of protein with or without RNA.

Figure 18:
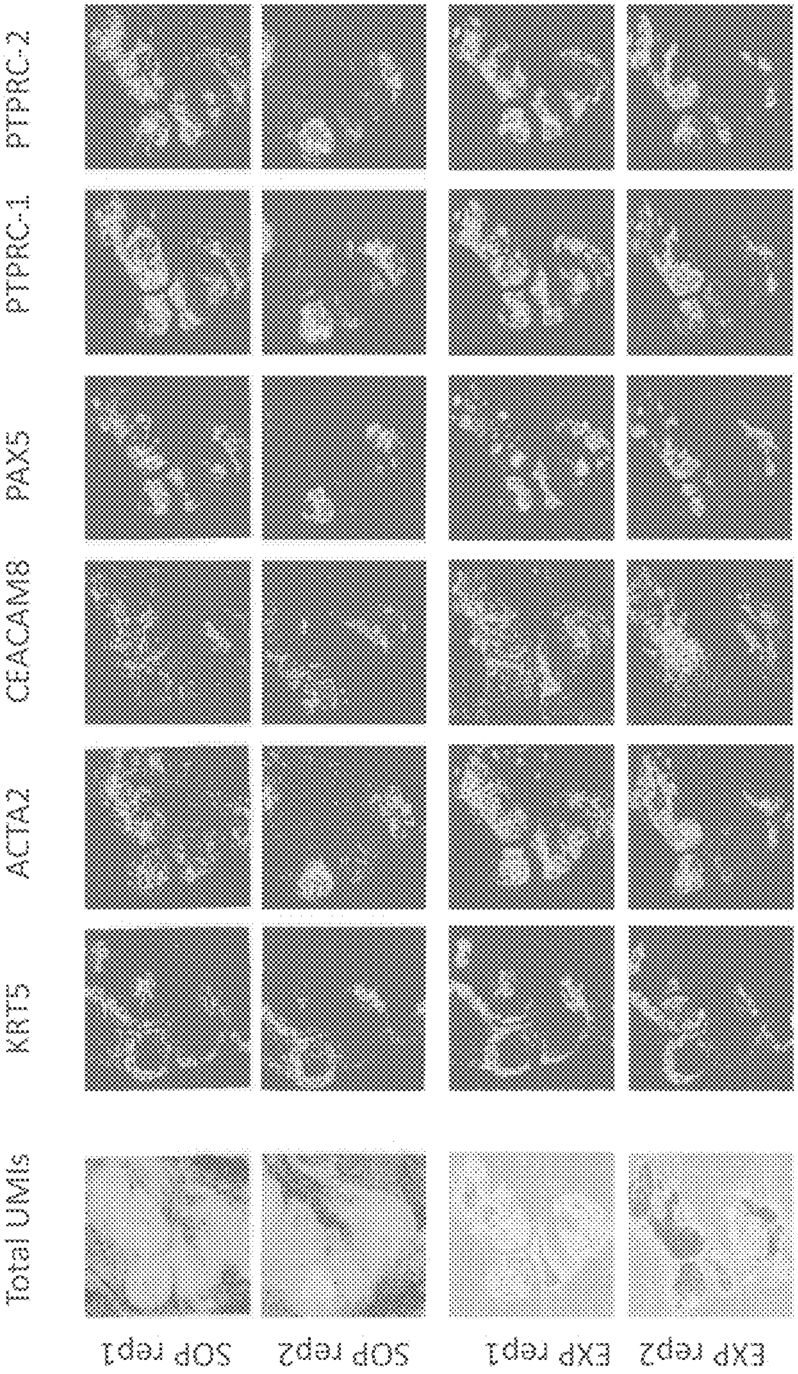
FIG. 18 shows representative images of protein detection in human samples to detect total protein and individual proteins.

While proteomic and transcriptomic coverage can be attained using the methods described herein, location and/or abundance of individual targets can be determined as well. As shown in FIG. 18, individual proteins, including KRT5, ACTA2, CEACAM8, PAX5, PTPRC-1, PTPRC-2, CD3E, CD8A, and EPCAM, can be detected using the reagent concentrations in the experimental group (e.g., 500 mM NaCl, 2% ethylene carbonate, and 2.5% glycerol).

TABLE 1

Individual Proteins Detected

| Protein | Protein Name/Function |
|---|---|
| KRT5 | Keratin 5 |
| ACTA2 | Smooth muscle actin |
| CEACAM8 | Cell adhesion, cell migration, and pathogen binding factor |
| PAX5 | Master regulator of B-cell development |
| PTPRC (1 or 2) | Blood-cell marker excluding RBCs and platelets |
| CD3E | T-cell receptor subunit |
| CD8A | T-lymphocyte surface glycoprotein |
| EPCAM | Epithelial cell adhesion molecule |

Figure 19:
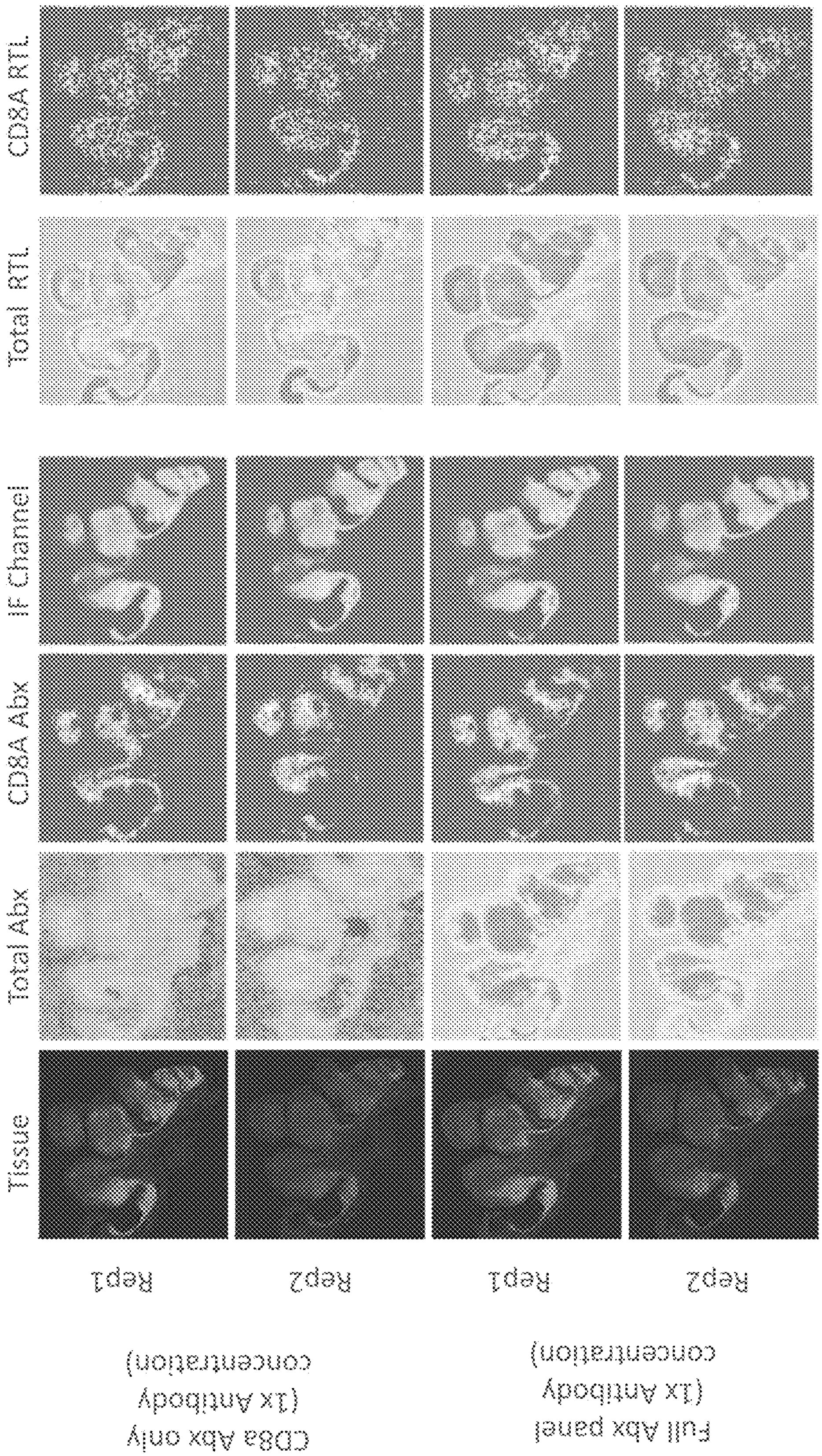
FIG. 19 shows representative images of protein and RNA detection of CD8A using methods disclosed herein.

Further, to determine whether both RNA and protein expression overlap in location, detection of CD8a protein and RNA was performed. As a positive control for location of CD8a, the samples also were counterstained with an antibody to CD8a and detected using immunofluorescence (IF channel column in FIG. 19). FIG. 19 shows results from two different samples where (1) only CD8a oligo-tagged antibodies (top) were used (2) and where a full proteome panel was used and CD8a expression was images (bottom). In both instances, protein (Total Abx and CD8 Abx) was readily detected. In addition, there was overlap of protein expression with RNA expression (Total RTL and CD8A RTL). In each instance, CD8A protein or RNA expression overlapped with CD8A immunofluorescent detection, demonstrating that the methods disclosed herein (e.g., using a reagent medium comprising 500 mM NaCl, 2% ethylene carbonate, and 2.5% glycerol) can be used to readily detect individual protein and RNA biomarkers.

Taken together, these data demonstrate the ability to increase detection of protein in a sample using these sandwich methods by varying reagent concentration, and in particular, by adding NaCl, ethylene carbonate, and glycerol.

Figure 20:
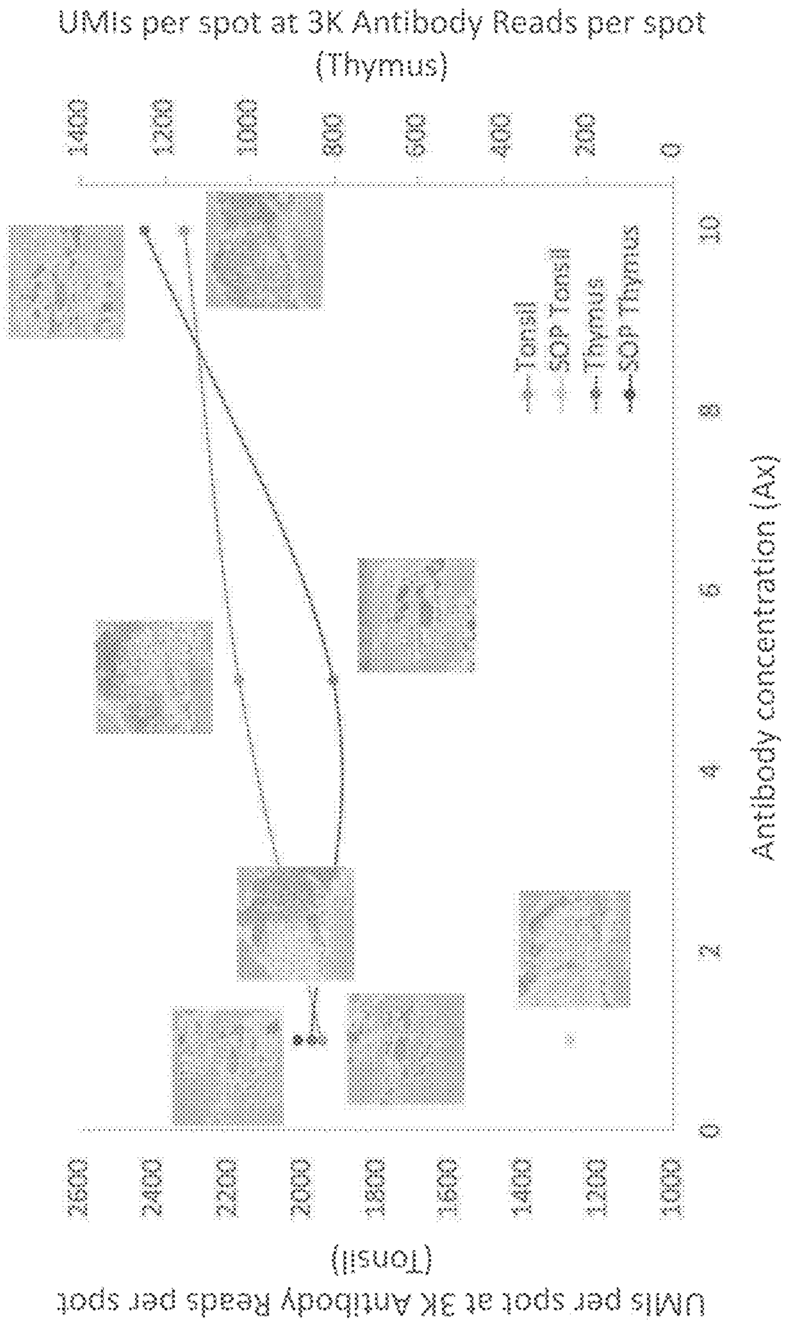
FIG. 20 shows a chart of UMIs per spot as oligo-tagged antibody concentration increased.

Example 3—Methods for Spatial Analysis of Protein and RNA with Sandwich Process in Reagent Medium with Increased Antibody Concentration In another experiment, the protocol was followed as described in Example 1 to detect proteins in tonsil and thymus mouse tissue samples. Here, the concentration of oligo-tagged antibodies was increased to see whether there was a correlation between increased antibody concentration and increased protein detection. As a baseline control, 0.1 μg/reaction total of a pool of oligo-tagged antibodies was used, and this was set as a 1× concentration. As shown in FIG. 20, increases in protein detection were generally observed at about 2× to at least 10× oligo-tagged antibody concentration for tonsil, and 6× to at least 10× increased oligo-tagged antibody concentration (i.e., 0.6 μg/reaction to 1.0 μg/reaction) for thymus, as measured by increased detection of UMIs per spot on the array in both tonsil samples (left axis) and thymus samples (right axis).

Taken together, these data demonstrate the ability to increase detection of protein in a sample using these sandwich methods by increasing antibody concentration during antibody incubation.

NUMBERED EMBODIMENTS

Embodiment 1 is a method for analyzing an analyte in a biological sample mounted on a first substrate, the method comprising: (a) contacting the biological sample with a plurality of analyte capture agents, wherein an analyte capture agent of the plurality of analyte capture agents comprises an analyte binding moiety and a capture agent barcode domain, wherein the contacting results in the analyte binding moiety specifically binding to the analyte, and wherein the capture agent barcode domain comprises an analyte binding moiety barcode and a capture handle sequence; (b) aligning the first substrate with a second substrate comprising an array, such that at least a portion of the biological sample is aligned with at least a portion of the array, wherein the array comprises a plurality of capture probes, wherein a first capture probe of the plurality of capture probes comprises: (i) a first spatial barcode and (ii) a first capture domain; (c) when the biological sample is aligned with at least a portion of the array, contacting the biological sample and/or the array with a reagent medium comprising a monovalent salt or divalent salt, and releasing the capture agent barcode domain from the analyte capture agent; and (d) hybridizing the capture handle sequence of the capture agent barcode domain to the capture domain.

Embodiment 2 is the method of embodiment 1, wherein the monovalent salt or divalent salt in the reagent medium is at a concentration of about 100-750 mM.

Embodiment 3 is the method of embodiment 1 or 2, wherein the monovalent salt or divalent salt in the reagent medium is at a concentration of about 250 mM or about 500 mM.

Embodiment 4 is the method of any one of embodiments 1-3, wherein the monovalent salt is sodium chloride.

Embodiment 5 is the method of embodiment 4, wherein the sodium chloride in the reagent medium is at a concentration of about 250 mM.

Embodiment 6 is the method of embodiment 4, wherein the sodium chloride in the reagent medium is at a concentration of about 500 mM.

Embodiment 7 is the method of any one of embodiments 1-3, wherein the monovalent salt is potassium chloride.

Embodiment 8 is the method of embodiment 7, wherein the bivalent salt is magnesium chloride.

Embodiment 9 is the method of any one of embodiments 1-8, wherein the reagent medium further comprises ethylene carbonate.

Embodiment 10 is the method of embodiment 9, wherein the ethylene carbonate in the reagent medium comprises about 2% of the reagent medium.

Embodiment 11 is the method of any one of embodiments 1-10, wherein the reagent medium further comprises glycerol.

Embodiment 12 is the method of embodiment 11, wherein the glycerol in the reagent medium comprises about 2.5% of the reagent medium.

Embodiment 13 is the method of any one of embodiments 1-12, wherein the plurality of analyte capture agents is in an amount of about 0.1 μg to about 1.5 μg.

Embodiment 14 is the method of any one of embodiments 1-13, wherein the plurality of analyte capture agents is in an amount of about 0.6 μg to about 1.0 μg.

Embodiment 15 is the method of any one of embodiments 1-14, wherein the reagent medium further comprises a permeabilization agent, wherein the contacting in step (c) permeabilizes the biological sample.

Embodiment 16 is the method of embodiment 15, wherein the permeabilization agent comprises a protease.

Embodiment 17 is the method of embodiment 16, wherein the protease is selected from trypsin, pepsin, elastase, or proteinase K.

Embodiment 18 is the method of any one of embodiments 1-17, wherein the aligning comprises: (i) mounting the first substrate on a first member of a support device, the first member configured to retain the first substrate; (ii) mounting the second substrate on a second member of the support device; (iii) applying the reagent medium to the first substrate and/or the second substrate; and (iv) operating an alignment mechanism of the support device to move the first member and/or the second member such that at least a portion of the biological sample is aligned with at least a portion of the array, and such that the portion of the biological sample and the portion of the array contact the reagent medium.

Embodiment 19 is the method of embodiment 18, wherein the alignment mechanism is coupled to the first member, the second member, or both the first member and the second member.

Embodiment 20 is the method of embodiment 18 or 19, wherein the alignment mechanism comprises a linear actuator, optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/sec, and/or the linear actuator is configured to move the first member, the second member, or both the first member and the second member with an amount of force of at least 0.1 lbs.

Embodiment 21 is the method of any one of embodiments 1-20, wherein during the hybridization step, a separation distance is maintained between the first substrate and the second substrate, optionally wherein the separation distance is less than 50 microns, optionally wherein the separation distance is between 2-25 microns, optionally wherein the separation distance is measured in a direction orthogonal to the surface of the first substrate to which the biological sample is mounted, and/or at least the portion of the biological sample is vertically aligned with the at least portion of the array.

Embodiment 22 is the method of any one of embodiments 18-21, wherein at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample.

Embodiment 23 is the method of embodiment 22, wherein: the chamber comprises a partially or fully sealed chamber, and/or the second substrate comprises the spacer, and/or the first substrate comprises the spacer, and/or the applying the reagent medium to the first substrate and/or the second substrate comprises applying the reagent medium to a region of the spacer, the region outside an enclosed area of the second substrate, or the enclosed area formed by the spacer.

Embodiment 24 is the method of any one of embodiments 18-23, wherein as the first substrate and/or the second substrate are moved via the alignment mechanism, the first substrate is at an angle relative to the second substrate such that a dropped slide of the first substrate and a portion of the second substrate contact the reagent medium, optionally wherein: the dropped side of the first substrate urges the reagent medium toward the opposite direction, and/or the alignment mechanism further moves the first substrate and/or the second substrate to maintain an approximately parallel arrangement of the first substrate and the second substrate and a separation distance between the first substrate and the second substrate, optionally when the approximately parallel arrangement and the separation distance are maintained, the spacer fully encloses and surrounds the at least portion of the biological sample and the at least portion of the array, and the spacer forms the sides of the chamber which hold a volume of the reagent medium.

Embodiment 25 is the method of any one of embodiments 1-24, wherein the reagent medium further comprises a detergent.

Embodiment 26 is the method of embodiment 25, wherein the detergent is selected from sodium dodecyl sulfate (SDS), sarkosyl, saponin, a nonionic surfactant, polysorbate 20, or a combination thereof.

Embodiment 27 is the method of embodiment 26, wherein the reagent medium comprises less than 5 w/v % of SDS and/or sarkosyl.

Embodiment 28 is the method embodiment 26, wherein the reagent medium comprises at least 5% w/v % of SDS and/or sarkosyl.

Embodiment 29 is the method of any one of embodiments 1-26, wherein the reagent medium does not comprise SDS or sarkosyl.

Embodiment 30 is the method of any one of embodiments 1-29, wherein the reagent medium further comprises polyethylene glycol (PEG).

Embodiment 31 is the method of any one of embodiments 1-30, wherein the first capture probe comprises a poly(T) sequence, preferably wherein the first capture domain of the first capture probe comprises the poly(T) sequence.

Embodiment 32 is the method of any one of embodiments 1-31, wherein the first capture domain of the first capture probe comprises a sequence substantially complementary to the capture handle sequence.

Embodiment 33 is the method of any one of embodiments 1-32, wherein the first capture probe further comprises one or more functional domains, a unique molecular identifier (UMI), a cleavage domain, and combinations thereof.

Embodiment 34 is the method of any one of embodiments 1-33, further comprising determining (i) all or a part of the capture agent barcode domain, or a complement thereof; and (ii) the first spatial barcode, or a complement thereof.

Embodiment 35 is the method of embodiment 34, further comprising using the determined sequence of (i) and (ii) to determine the location and/or abundance of the analyte in the biological sample.

Embodiment 36 is the method of embodiment 34 or 35, wherein the determining comprises sequencing (i) all or a part of the sequence of the capture agent barcode domain, or a complement thereof, and (ii) the first spatial barcode, or a complement thereof.

Embodiment 37 is the method of any one of embodiments 1-36, wherein the analyte binding moiety is an antibody or an antigen binding fragment thereof.

Embodiment 38 is the method of any one of embodiments 1-37, wherein the analyte capture agent comprises a linker.

Embodiment 39 is the method of embodiment 38, wherein the linker is a cleavable linker.

Embodiment 40 is the method of embodiment 39, wherein the cleavable linker is a photo-cleavable linker, a UV-cleavable linker, or an enzyme cleavable linker.

Embodiment 41 is the method of any one of embodiments 1-40, wherein the analyte is a protein.

Embodiment 42 is the method of any one of embodiments 1-41, wherein the analyte is an intracellular protein.

Embodiment 43 is the method of any one of embodiments 1-41, wherein the analyte is an extracellular protein.

Embodiment The method of any one of embodiments 1-43, further comprising analyzing a different analyte in the biological sample.

Embodiment 45 is the method of embodiment 44, wherein the analyzing the different analyte comprises: (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) coupling the first probe and the second probe, thereby generating a connected probe; (c) when the biological sample is aligned with at least a portion of the array, (i) releasing the connected probe from the different analyte and (ii) migrating the connected probe from the biological sample to the array; and (d) hybridizing the connected probe to a second capture domain of a second capture probe comprised in the plurality of capture probes, wherein the second capture probe comprises: (i) a second spatial barcode and (ii) the second capture domain.

Embodiment 46 is the method of embodiment 45, wherein the first probe and the second probe are on a contiguous nucleic acid sequence.

Embodiment 47 is the method of embodiment 46, wherein the first probe is on the 3' end of the contiguous nucleic acid sequence.

Embodiment 48 is the method of embodiments 46 or 47, wherein the second probe is on the 5' end of the contiguous nucleic acid sequence.

Embodiment 49 is the method of any one of embodiments 45-48, wherein the adjacent sequences abut one another.

Embodiment 50 is the method of any one of embodiments 45-48, wherein the adjacent sequences are at least 1, 2, 3, 4, 5, 6, 7, 8, 9, 10, or more nucleotides away from one another.

Embodiment 51 is the method of embodiment 50, further comprising generating an extended first probe using a polymerase, wherein the extended first probe comprises a sequence complementary to a sequence between the sequence hybridized to the first probe and the sequence hybridized to the second probe.

Embodiment 52 is the method of embodiment 50, further comprising generating an extended second probe using a polymerase, wherein the extended second probe comprises a sequence complementary to a sequence between the sequence hybridized to the first probe and the sequence hybridized to the second probe.

Embodiment 53 is the method of any one of embodiments 45-52, further comprising hybridizing a third probe to the first probe and the second probe.

Embodiment 54 is the method of embodiment 53, wherein the third probe comprises: (i) a sequence that is at least 80%, at least 85%, at least 90%, at least 95%, at least 96%, at least 97%, at least 98%, or at least 99%, or 100% complementary to a portion of the first probe that hybridizes to the third probe; and (ii) a sequence that is at least 80%, at least 85%, at least 90%, at least 95%, at least 96%, at least 97%, at least 98%, or at least 99%, or 100% complementary to a portion of the second probe that hybridizes to the third probe.

Embodiment 55 is the method of any one of embodiments 45-54, wherein the coupling the first probe and the second probe comprises ligating via a ligase the first probe and the second probe.

Embodiment 56 is the method of any one of embodiments 51-55, wherein the coupling the first probe and the second probe comprises ligating via a ligase: (i) the first probe and the extended second probe; or (ii) the extended first probe and the second probe.

Embodiment 57 is the method of embodiment 55 or 56, wherein the ligase is selected from a *Chlorella* virus DNA ligase, a single stranded DNA ligase, or a T4 DNA ligase.

Embodiment 58 is the method of any one of embodiments 45-57, further comprising amplifying the connected probe prior to the step of releasing the connected probe from the different analyte.

Embodiment 59 is the method of embodiment 58, wherein the amplifying comprises rolling circle amplification.

Embodiment 60 is the method of any one of embodiments 1-59, wherein the reagent medium further comprises a nuclease.

Embodiment 61 is the method of embodiment 60, wherein the nuclease comprises an RNase, optionally wherein the RNase is selected from RNase A, RNase C, RNase H, or RNase I.

Embodiment 62 is the method of any one of embodiments 45-61, further comprising determining (i) all or a part of the sequence of the connected probe, or a complement thereof, and (ii) the second spatial barcode, or a complement thereof, optionally wherein the method further comprises using the determined sequence of (i) and (ii) to determine the location and/or abundance of the different analyte in the biological sample.

Embodiment 63 is the method of embodiment 62, wherein the determining comprises sequencing (i) all or a part of the sequence of the connected probe, or a complement thereof, and (ii) the second spatial barcode, or a complement thereof.

Embodiment 64 is the method of any one of embodiments 45-63, wherein at least 50% of the connected probe released from the portion of the biological sample aligned with the portion of the array are captured by capture probes of the portion of the array.

Embodiment 65 is the method of any one of embodiments 45-64, wherein at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the connected probe are detected in spots directly under the biological sample.

Embodiment 66 is the method of any one of embodiments 45-65, wherein the different analyte is RNA.

Embodiment 67 is the method of embodiment 66, wherein the RNA is mRNA.

Embodiment 68 is the methods of any one of embodiments 1-67, wherein the biological sample is a tissue sample.

Embodiment 69 is the method of embodiment 68, wherein the tissue sample is a solid tissue sample.

Embodiment 70 is the method of embodiment 69, wherein the solid tissue sample is a tissue section.

Embodiment 71 is the method of any one of embodiments 1-70, wherein the biological sample is a fixed tissue sample.

Embodiment 72 is the method of embodiment 71, wherein the fixed tissue sample is a formalin fixed paraffin embedded (FFPE) tissue sample.

Embodiment 73 is the method embodiment 72, wherein the FFPE tissue sample is deparaffinized and decrosslinked prior to step (a).

Embodiment 74 is the method of embodiment 71, wherein the fixed tissue sample is a formalin fixed paraffin embedded cell pellet.

Embodiment 75 is the method of embodiment 68, wherein the tissue sample is a fresh frozen tissue sample.

Embodiment 76 is the method of any one of embodiments 1-75, wherein the biological sample is stained and/or destained.

Embodiment 77 is the method of embodiment 76, wherein the biological sample is stained using hematoxylin and/or eosin, immunohistochemistry, and/or immunofluorescence.

Embodiment 78 is the method of embodiment 68, wherein the tissue sample is a tissue microarray.

Embodiment 79 is the method of any one of embodiments 45-78, wherein the connected probe is extended using the second capture probe as template, thereby generating an extended connected probe.

Embodiment 80 is the method of embodiment 79, further comprising releasing the extended connected probe from the capture probe and/or from the array.

Embodiment 81 is the method of any one of embodiments 1-79, wherein the capture agent barcode domain is extended using the second capture probe as template, thereby generating an extended capture agent barcode domain.

Embodiment 82 is the method of embodiment 81, further comprising releasing the extended capture agent barcode domain from the capture probe and/or from the array.

Embodiment 83 is the method of any one of embodiments 45-82, wherein the first spatial barcode and the second spatial barcode are the same.

Embodiment 84 is the method of any one of embodiments 45-82, wherein the first spatial barcode and the second spatial barcode are different.

Embodiment 85 is the method of any one of embodiments 45-84, wherein the first capture domain and the second capture domain are the same.

Embodiment 86 is the method of any one of embodiments 45-84, wherein the first capture domain and the second capture domain are different.

Embodiment 87 is the method of any one of embodiments 1-86, further comprising imaging the biological sample.

Embodiment 88 is a method for analyzing an analyte in a biological sample mounted on a first substrate, the method comprising: (a) contacting the biological sample with a plurality of analyte capture agents, wherein an analyte capture agent of the plurality of analyte capture agents comprises an analyte binding moiety and a capture agent barcode domain, wherein the contacting results in the analyte binding moiety specifically binding to the analyte, and wherein the capture agent barcode domain comprises an analyte binding moiety barcode and a capture handle sequence; (b) contacting the biological sample with an array, wherein the array comprises a plurality of capture probes, wherein a first capture probe of the plurality of capture probes comprises: (i) a first spatial barcode and (ii) a first capture domain; (c) contacting the biological sample and/or the array with a reagent medium comprising a monovalent salt or divalent salt, and releasing the capture agent barcode domain from the analyte capture agent; and (d) hybridizing the capture handle sequence of the capture agent barcode domain to the capture domain.

Embodiment 89 is the method of embodiment 88, wherein the monovalent salt is sodium chloride.

Embodiment 90 is the method of embodiment 89, wherein the sodium chloride in the reagent medium is at a concentration of about 250 mM.

Embodiment 91 is the method of embodiment 89, wherein the sodium chloride in the reagent medium is at a concentration of about 500 mM.

Embodiment 92 is the method of any one of embodiments 88-91, wherein the reagent medium further comprises ethylene carbonate.

Embodiment 93 is the method of embodiment 92, wherein the ethylene carbonate in the reagent medium comprises about 2% of the reagent medium.

Embodiment 94 is the method of any one of embodiments 88-93, wherein the reagent medium further comprises glycerol.

Embodiment 95 is the method of embodiment 94, wherein the glycerol in the reagent medium comprises about 2.5% of the reagent medium.

Embodiment 96 is the method of any one of embodiments 88-95 wherein the plurality of analyte capture agents is in an amount of about 0.1 μg to about 1.5 μg.

Embodiment 97 is the method of any one of embodiments 88-96, wherein the plurality of analyte capture agents is in an amount of about 0.6 μg to about 1.0 μg.

Embodiment 98 is the method of any one of embodiments 88-97, further comprising determining (i) all or a part of the capture agent barcode domain, or a complement thereof; and (ii) the first spatial barcode, or a complement thereof.

Embodiment 99 is the method of embodiment 98, further comprising using the determined sequence of (i) and (ii) to determine the location and/or abundance of the analyte in the biological sample.

Embodiment 100 is the method of embodiment 98 or 99, wherein the determining comprises sequencing (i) all or a part of the sequence of the capture agent barcode domain, or a complement thereof, and (ii) the first spatial barcode, or a complement thereof.

Embodiment 101 is the method of any one of embodiments 88-100, further comprising analyzing a different analyte in the biological sample.

Embodiment 102 is the method of embodiment 101, wherein the analyzing the different analyte comprises: (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) coupling the first probe and the second probe, thereby generating a connected probe; (c) when the biological sample is aligned with at least a portion of the array, (i) releasing the connected probe from the different analyte and (ii) migrating the connected probe from the biological sample to the array; and (d) hybridizing the connected probe to a second capture domain of a second capture probe comprised in the plurality of capture probes, wherein the second capture probe comprises: (i) a second spatial barcode and (ii) the second capture domain.

Embodiment 103 is the method of any one of embodiments 88-102, further comprising determining (i) all or a part of the sequence of the connected probe, or a complement thereof, and (ii) the second spatial barcode, or a complement thereof, optionally wherein the method further comprises using the determined sequence of (i) and (ii) to determine the location and/or abundance of the different analyte in the biological sample.

Embodiment 104 is the method of embodiment 103, wherein the determining comprises sequencing (i) all or a part of the sequence of the connected probe, or a complement thereof, and (ii) the second spatial barcode, or a complement thereof.

Embodiment 105 is a system or kit for analyzing an analyte in a biological sample, the system or the kit comprising: (a) a support device configured to retain a first substrate and a second substrate, wherein the biological sample is placed on the first substrate, and wherein the second substrate comprises a plurality of capture probes, wherein a capture probe of the plurality of capture probes comprises: (i) a spatial barcode and (ii) a capture domain; (b) a plurality of analyte capture agents, wherein an analyte capture agent of the plurality of analyte capture agents comprises an analyte binding moiety and a capture agent barcode domain, wherein the analyte binding moiety specifically binds to the analyte, and wherein the capture agent barcode domain comprises an analyte binding moiety barcode and a capture handle sequence; (c) a reagent medium comprising a monovalent salt or divalent salt; and (d) instructions for performing the method of any one of embodiments 1-104.

Embodiment 106 is the system or kit of embodiment 105, further comprising a first probe and a second probe, wherein the first probe and the second probe each comprise a sequence that is substantially complementary to adjacent sequences of the analyte, wherein the second probe comprises a capture probe binding domain, and wherein the first probe and the second probe are capable of being ligated together to form a connected probe.

Embodiment 107 is the system or kit of embodiment 105 or 106, wherein the reagent medium further comprises a permeabilization agent.

Embodiment 108 is the system or kit of embodiment 107, wherein the permeabilization agent is pepsin or proteinase K.

Embodiment 109 is the system or kit of any one of embodiments 105-108, wherein the reagent medium further comprises an agent for releasing the connected probe from the analyte when hybridized thereto.

Embodiment 110 is the system or kit of embodiment 109, wherein the agent for releasing the connected probe is an RNAse, optionally wherein the RNAse is selected from RNase A, RNase C, RNase H, or RNase I.

Embodiment 111 is the system or kit of any one of embodiments 105-110, further comprising an alignment mechanism on the support device to align the first substrate and the second substrate.

Embodiment 112 is the system or kit of embodiment 111, wherein the alignment mechanism comprises a linear actuator, wherein the first substrate comprises a first member and the second substrate comprises a second member, and optionally wherein: the linear actuator is configured to move the second member along an axis orthogonal to the plane or the first member and/or the second member, and/or the linear actuator is configured to move the first member along an axis orthogonal to the plane of the first member and/or the second member, and/or the linear actuator is configured to move the first member, the second member, or both the first member and the second member at a velocity of at least 0.1 mm/see, and/or the linear actuator is configured to move the first member, the second member, or both the first member and the second member with an amount of force of at least 0.1 lbs.

What is claimed is:

1. A method for analyzing a protein analyte in a biological sample mounted on a first substrate, the method comprising:

(a) contacting the biological sample with a plurality of analyte capture agents, wherein an analyte capture agent of the plurality of analyte capture agents comprises an analyte binding moiety and a capture agent barcode domain,
   wherein the contacting results in the analyte binding moiety binding to the protein analyte, and wherein the capture agent barcode domain comprises an analyte binding moiety barcode and a capture handle sequence;

(b) aligning the first substrate with a second substrate comprising an array, such that at least a portion of the biological sample is aligned with at least a portion of the array, wherein the array comprises a plurality of capture probes, wherein a capture probe of the plurality of capture probes comprises (i) a spatial barcode and (ii) a capture domain;

(c) when the biological sample is aligned with at least a portion of the array, contacting the biological sample and/or the array with a reagent medium comprising a monovalent salt or divalent salt, and releasing the capture agent barcode domain from the analyte capture agent; and (d) hybridizing the capture handle sequence of the capture agent barcode domain to the capture domain.

2. The method of claim 1, wherein the monovalent salt or divalent salt in the reagent medium is at a concentration of about 100-750 mM.

3. The method of claim 1, wherein the monovalent salt or divalent salt in the reagent medium is at a concentration of about 250 mM or about 500 mM.

4. The method of claim 1, wherein the monovalent salt is sodium chloride or potassium chloride.

5. The method of claim 1, wherein the divalent salt is magnesium chloride.

6. The method of claim 1, wherein the reagent medium further comprises ethylene carbonate, glycerol, or a combination thereof.

7. The method of claim 6, wherein the reagent medium comprises ethylene carbonate present in an amount of about 2% of the reagent medium.

8. The method of claim 6, wherein the reagent medium comprises glycerol present in an amount of about 2.5% of the reagent medium.

9. The method of claim 1, wherein the reagent medium further comprises a detergent, polyethylene glycol (PEG), or a combination thereof.

10. The method of claim 1, wherein the plurality of analyte capture agents is in an amount of about 0.1 μg to about 1.5 μg.

11. The method of claim 1, wherein the reagent medium further comprises a permeabilization agent, wherein the contacting in step (c) permeabilizes the biological sample.

12. The method of claim 1, wherein the aligning comprises:

(i) mounting the first substrate on a first member of a support device, the first member configured to retain the first substrate;

(ii) mounting the second substrate on a second member of the support device;

(iii) applying the reagent medium to the first substrate and/or the second substrate; and (iv) operating an alignment mechanism of the support device to move the first member and/or the second member such that at least a portion of the biological sample is aligned with at least a portion of the array, and such that the portion of the biological sample and the portion of the array contact the reagent medium.

13. The method of claim 12, wherein at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample.

14. The method of claim 1, wherein the biological sample is a tissue section, optionally wherein the tissue section is a fresh frozen tissue section or a fixed tissue section.

15. The method of claim 1, further comprising extending the capture agent barcode domain using the capture probe as template, thereby generating an extended capture agent barcode domain and/or extending the capture probe using the capture agent barcode domain as a template, thereby generating an extended capture probe; using the extended capture agent barcode domain or the extended capture probe to determine a sequence of (i) all or a part of the capture agent barcode domain, or a complement thereof; and (ii) the spatial barcode, or a complement thereof, and using the determined sequences of (i) and (ii) to determine the location of the protein analyte in the biological sample.

16. The method of claim 15, wherein the determining comprises sequencing (i) all or a part of the extended capture agent barcode domain or the extended capture probe, and (ii) the spatial barcode, or the complement thereof.

17. The method of claim 1, wherein the capture domain of the capture probe comprises a poly (T) sequence, and/or wherein the capture probe further comprises one or more functional domains, a unique molecular identifier (UMI), a cleavage domain, or a combination thereof.

18. The method of claim 1, further comprising analyzing a nucleic acid analyte, the method comprising:

hybridizing a first probe and a second probe to the nucleic acid analyte, wherein the first probe and the second probe each comprise a sequence that is substantially complementary to adjacent sequences of the nucleic acid analyte, and wherein the second probe comprises a capture probe binding domain;

coupling the first probe and the second probe, thereby generating a connected probe;

when the biological sample is aligned with at least a portion of the array, releasing the connected probe from the nucleic acid analyte; and hybridizing the connected probe to a second capture domain of a second capture probe comprised in the plurality of capture probes, wherein the second capture probe comprises (i) a second spatial barcode and (ii) the second capture domain.

19. The method of claim 18, further comprising generating an extended connected probe using the second capture probe as a template and/or generating an extended second capture probe using the connected probe as a template; and using the extended connected probe or the extended second capture probe to determine (i) all or a part of the sequence of the connected probe, or a complement thereof, and (ii) the second spatial barcode, or a complement thereof, and using the determined sequence of (i) and (ii) to determine location of the nucleic acid analyte in the biological sample.

20. The method of claim 1, wherein the analyte binding moiety is an antibody or an antigen binding fragment thereof, and wherein the protein analyte is an intracellular or extracellular protein.

* * * * *